United States Patent
Kim et al.

(10) Patent No.: US 9,994,632 B2
(45) Date of Patent: *Jun. 12, 2018

(54) HUMANIZED OR AFFINITY-MATURED ANTI ANG-2 ANTIBODY AND USES THEREOF

(71) Applicant: Samsung Electronics Co., Ltd., Suwon-si, Gyeonggi-do (KR)

(72) Inventors: Seok Kyun Kim, Seoul (KR); Sunghyun Kim, Hwaseong-si (KR); Sang Yeul Han, Yongin-si (KR); Seung Hyun Lee, Suwon-si (KR); Su Jin Kim, Yongin-si (KR); Yong In Kim, Seongnam-si (KR); Hyung-Chan Kim, Yongin-si (KR); Kwang Hoon Lee, Osan-si (KR); Hyo Seon Lee, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 201 days.

This patent is subject to a terminal disclaimer.

(21) Appl. No.: 14/721,591

(22) Filed: May 26, 2015

(65) Prior Publication Data
US 2015/0337033 A1 Nov. 26, 2015

(30) Foreign Application Priority Data
May 26, 2014 (KR) ........................ 10-2014-0063251

(51) Int. Cl.
| | | |
|---|---|---|
| C07K 16/00 | (2006.01) | |
| C07K 16/28 | (2006.01) | |
| C07K 16/22 | (2006.01) | |
| A61K 39/395 | (2006.01) | |
| G01N 33/68 | (2006.01) | |
| C07K 14/705 | (2006.01) | |
| C07K 14/515 | (2006.01) | |
| A61K 39/00 | (2006.01) | |
| A61K 38/00 | (2006.01) | |

(52) U.S. Cl.
CPC .......... *C07K 16/22* (2013.01); *A61K 39/3955* (2013.01); *G01N 33/6887* (2013.01); *G01N 33/6893* (2013.01); *A61K 38/00* (2013.01); *A61K 2039/505* (2013.01); *C07K 14/515* (2013.01); *C07K 14/705* (2013.01); *C07K 2317/24* (2013.01); *C07K 2317/567* (2013.01); *C07K 2317/622* (2013.01); *C07K 2317/74* (2013.01); *C07K 2317/75* (2013.01); *C07K 2317/76* (2013.01); *C07K 2317/92* (2013.01); *G01N 2333/515* (2013.01)

(58) Field of Classification Search
None
See application file for complete search history.

(56) References Cited

U.S. PATENT DOCUMENTS

| | | | |
|---|---|---|---|
| 5,859,205 A * | 1/1999 | Adair .................... | C07K 16/18 530/387.1 |
| 7,977,461 B2 | 7/2011 | Takayama et al. | |
| 8,486,404 B2 | 7/2013 | Ryu et al. | |
| 2011/0027286 A1 | 2/2011 | Thurston et al. | |
| 2011/0311546 A1 | 12/2011 | Oliner et al. | |
| 2012/0034237 A1 | 2/2012 | Boone et al. | |
| 2013/0156789 A1 | 6/2013 | Brinkmann et al. | |
| 2013/0186797 A1 | 7/2013 | Walsh et al. | |
| 2014/0302039 A1 * | 10/2014 | Jeong .................... | C07K 16/22 424/138.1 |
| 2015/0030603 A1 * | 1/2015 | Kim .................... | A61K 38/1891 424/139.1 |

FOREIGN PATENT DOCUMENTS

| | | |
|---|---|---|
| EP | 1876240 A1 | 1/2008 |
| KR | 20110068184 A | 6/2011 |
| KR | 20110084536 A | 7/2011 |

OTHER PUBLICATIONS

Klimka et al.,Human anti-CD30 recombinant antibodies by guided phage antibody selection using cell panning. British Journal of Cancer (2000) 83:252- 260.*
Beiboer et al., Guided selection of a pan carcinoma specific antibody reveals similar binding characteristics yet structural divergence between the original murine antibody and its human equivalent. J. Mol. Biol. 296: 833-849 (2000).*
MacCallum et al. Antibody-antigen interactions: contact analysis and binding site topography. J. Mol. Biol., 262, 732-745, 1996.*
Casset et al. A peptide mimetic of an anti-CD4 monoclonal antibody by rational design. Biochemical and Biophysical Research Communications, 307:198-205, 2003.*
Eduardo Padlan, Anatomy of the antibody molecule. Mol Immunol. Feb. 1994;31(3):169-217.*
Rudikoff et al Single amino acid substitution altering antigen-binding specificity. Proc Natl Acad Sci U S A. Mar. 1982;79(6):1979-83.*
Paul, Fundamental Immunology, 3rd Edition, 1993, pp. 292-295.*
Barton et al., "Crystal structures of the Tie2 receptor ectodomain and the angiopoietin-2-Tie2 complex", *Nature Structural & Molecular Biology*, 13(6): 524-532 (2006).

* cited by examiner

*Primary Examiner* — Maher M Haddad
(74) *Attorney, Agent, or Firm* — Leydig, Voit & Mayer, Ltd.

(57) ABSTRACT

An anti-Ang2 antibody or an antigen-binding fragment thereof that specifically binds to an angiogenesis-inducing factor Angiopoietin-2 (Ang2) and complexes with a Tie2 receptor through Ang2, and methods of using the same.

8 Claims, 7 Drawing Sheets

SEQUENCE LISTING

```
<160> NUMBER OF SEQ ID NOS: 92

<210> SEQ ID NO 1
<211> LENGTH: 6
<212> TYPE: PRT
<213> ORGANISM: Artificial Sequence
<220> FEATURE:
<223> OTHER INFORMATION: Synthetic CDR-H1 of anti-Ang2 antibody

<400> SEQUENCE: 1
```

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody

<400> SEQUENCE: 2

Tyr Ile Asn Tyr Ser Gly Asn Thr Asp Tyr Asn Pro Ser Leu Lys Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic CDR-H3 of anti-Ang2 antibody

<400> SEQUENCE: 3

Gly Asn Phe Glu Gly Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody

<400> SEQUENCE: 4

Lys Ala Ser Gln Ser Val Ser Asn Asp Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody

<400> SEQUENCE: 5

Tyr Ala Ser Asn Arg Tyr Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody

<400> SEQUENCE: 6

Gln Gln Asp Tyr Ser Ser Pro Trp Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic Amino acid sequence of heavy chain
      variable region

<400> SEQUENCE: 7

```
Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Asn Thr Asp Tyr Asn Pro Ser Leu
    50                  55                  60

Lys Ser Arg Ser Ser Ile Thr Arg Asp Thr Ser Lys Asn Gln Phe Phe
 65                  70                  75                  80

Leu Gln Leu Asn Ser Val Thr Thr Gly Asp Thr Ala Thr Tyr Tyr Cys
                85                  90                  95

Ala Arg Gly Asn Phe Glu Gly Ala Met Asp Tyr Trp Gly Gln Gly Thr
            100                 105                 110

Ser Val Thr Val Ser Ser
        115
```

```
<210> SEQ ID NO 8
<211> LENGTH: 354
<212> TYPE: DNA
<213> ORGANISM: Artificial Sequence
<220> FEATURE:
<223> OTHER INFORMATION: Synthetic Nucleotide sequence encoding heavy
      chain variable region

<400> SEQUENCE: 8
gatgtgcagc ttcaggagtc gggacctgac ctggtgaaac cttctcagtc tctgtccctc     60
acctgcactg tcactggcta ctcaatcacc agtgattatg cctggaactg gatccggcag    120
tttccaggaa acaaactgga gtggatgggc tacataaact acagtggtaa cactgactac    180
aacccatctc tcaaaagtcg aagctctatc actcgagaca catccaagaa ccagttcttc    240
ctgcagttga attctgtgac tactggggac acagccacat attactgtgc aagaggtaac    300
ttcgaaggtg ctatggacta ctggggtcaa ggaacctcag tcaccgtctc ctca          354
```

```
<210> SEQ ID NO 9
<211> LENGTH: 107
<212> TYPE: PRT
<213> ORGANISM: Artificial Sequence
<220> FEATURE:
<223> OTHER INFORMATION: Synthetic Amino acid sequence of light chain
      variable region

<400> SEQUENCE: 9

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Pro Gly Val Pro Asp Arg Phe Thr Gly
    50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105
```

<210> SEQ ID NO 10
<211> LENGTH: 321
<212> TYPE: DNA
<213> ORGANISM: Artificial Sequence
<220> FEATURE:
<223> OTHER INFORMATION: Synthetic Nucleotide sequence emcoding light
      chain variable region

<400> SEQUENCE: 10

```
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatactat gcatccaatc gctacctgg agtccctgat      180 cgcttcactg gcagtggata tgggacggat ttcactttca ccatcagcac tgtgcaggct     240
gaagacctgg cagtttattt ctgtcagcag gattatagct ctccgtggac gttcggtgga    300
ggcaccaagc tggaaatcaa a                                               321
```

<210> SEQ ID NO 11
<211> LENGTH: 496
<212> TYPE: PRT
<213> ORGANISM: Artificial Sequence
<220> FEATURE:
<223> OTHER INFORMATION: Synthetic Human Ang2

<400> SEQUENCE: 11

| Met | Trp | Gln | Ile | Val | Phe | Phe | Thr | Leu | Ser | Cys | Asp | Leu | Val | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Ala | Tyr | Asn | Asn | Phe | Arg | Lys | Ser | Met | Asp | Ser | Ile | Gly | Lys | Lys |
|     |     |     | 20  |     |     |     |     | 25  |     |     |     |     | 30  |     |     |

| Gln | Tyr | Gln | Val | Gln | His | Gly | Ser | Cys | Ser | Tyr | Thr | Phe | Leu | Leu | Pro |
|     |     | 35  |     |     |     |     | 40  |     |     |     |     | 45  |     |     |     |

| Glu | Met | Asp | Asn | Cys | Arg | Ser | Ser | Ser | Pro | Tyr | Val | Ser | Asn | Ala |
|     | 50  |     |     |     |     | 55  |     |     |     |     | 60  |     |     |     |

| Val | Gln | Arg | Asp | Ala | Pro | Leu | Glu | Tyr | Asp | Asp | Ser | Val | Gln | Arg | Leu |
| 65  |     |     |     |     | 70  |     |     |     |     | 75  |     |     |     |     | 80  |

| Gln | Val | Leu | Glu | Asn | Ile | Met | Glu | Asn | Asn | Thr | Gln | Trp | Leu | Met | Lys |
|     |     |     |     | 85  |     |     |     |     | 90  |     |     |     |     | 95  |     |

| Leu | Glu | Asn | Tyr | Ile | Gln | Asp | Asn | Met | Lys | Lys | Glu | Met | Val | Glu | Ile |
|     |     |     |     | 100 |     |     |     |     | 105 |     |     |     |     | 110 |     |

| Gln | Gln | Asn | Ala | Val | Gln | Asn | Gln | Thr | Ala | Val | Met | Ile | Glu | Ile | Gly |
|     |     |     | 115 |     |     |     |     | 120 |     |     |     |     | 125 |     |     |

| Thr | Asn | Leu | Leu | Asn | Gln | Thr | Ala | Glu | Gln | Thr | Arg | Lys | Leu | Thr | Asp |
|     |     |     | 130 |     |     |     |     | 135 |     |     |     |     | 140 |     |     |

| Val | Glu | Ala | Gln | Val | Leu | Asn | Gln | Thr | Thr | Arg | Leu | Glu | Leu | Gln | Leu |
| 145 |     |     |     |     | 150 |     |     |     |     | 155 |     |     |     |     | 160 |

| Leu | Glu | His | Ser | Leu | Ser | Thr | Asn | Lys | Leu | Glu | Lys | Gln | Ile | Leu | Asp |
|     |     |     |     | 165 |     |     |     |     | 170 |     |     |     |     | 175 |     |

| Gln | Thr | Ser | Glu | Ile | Asn | Lys | Leu | Gln | Asp | Lys | Asn | Ser | Phe | Leu | Glu |
|     |     |     |     | 180 |     |     |     |     | 185 |     |     |     |     | 190 |     |

| Lys | Lys | Val | Leu | Ala | Met | Glu | Asp | Lys | His | Ile | Ile | Gln | Leu | Gln | Ser |
|     |     |     | 195 |     |     |     |     | 200 |     |     |     |     | 205 |     |     |

| Ile | Lys | Glu | Glu | Lys | Asp | Gln | Leu | Gln | Val | Leu | Val | Ser | Lys | Gln | Asn |
|     | 210 |     |     |     |     | 215 |     |     |     |     | 220 |     |     |     |     |

| Ser | Ile | Ile | Glu | Glu | Leu | Glu | Lys | Lys | Ile | Val | Thr | Ala | Thr | Val | Asn |
| 225 |     |     |     |     | 230 |     |     |     |     | 235 |     |     |     |     | 240 |

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 12
<211> LENGTH: 121
<212> TYPE: PRT
<213> ORGANISM: Artificial Sequence
<220> FEATURE:
<223> OTHER INFORMATION: Synthetic Amino acid sequence of heavy chain
      variable region (4H10)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Pro Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Gly Phe Asp Tyr Trp Gly
            100                 105                 110

```
Gln Gly Thr Leu Val Thr Val Ser Ser
        115                 120

<210> SEQ ID NO 13
<211> LENGTH: 111
<212> TYPE: PRT
<213> ORGANISM: Artificial Sequence
<220> FEATURE:
<223> OTHER INFORMATION: Synthetic Amino acid sequence of light chain
      variable region (4H10)

<400> SEQUENCE: 13

Gln Ser Val Leu Thr Gln Pro Pro Ser Ala Ser Gly Thr Pro Gly Gln
 1               5                   10                  15

Arg Val Thr Ile Ser Cys Ser Gly Ser Ser Asn Ile Gly Ser Asn
             20                  25                  30

Tyr Val Asn Trp Tyr Gln Gln Leu Pro Gly Thr Ala Pro Lys Leu Leu
             35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
                100                 105                 110

<210> SEQ ID NO 14
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody

<400> SEQUENCE: 14

Lys Ile Ser Tyr Ser Gly Lys Thr Asp Tyr Asn Pro Ser Leu Lys Ser
 1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody

<400> SEQUENCE: 15

Lys Ile Asn Tyr Ala Gly Asn Thr Asp Tyr Asn Pro Ser Leu Lys Ser
 1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody

<400> SEQUENCE: 16

Lys Ala Ser Gln Ser Val Ser Asn Asp Val His
 1               5                   10

<210> SEQ ID NO 17
<211> LENGTH: 11
<212> TYPE: PRT
```

```
<213> ORGANISM: Artificial Sequence
<220> FEATURE:
<223> OTHER INFORMATION: Synthetic CDR-L1 of anti-Ang2 antibody

<400> SEQUENCE: 17

Lys Ala Ser Gln Phe Val Ser Thr Asp Val His
  1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody

<400> SEQUENCE: 18

Tyr Ala Ser Ile Pro Tyr Pro
  1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody

<400> SEQUENCE: 19

Gln His Asp Tyr Ser Ser Pro Phe Thr
  1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic CDR-H2 of anti-Ang2 antibody
<220> FEATURE:
<221> NAME/KEY: MOD_RES
<222> LOCATION: (1)
<223> OTHER INFORMATION: Xaa is Tyr (Y) or Lys (K)
<220> FEATURE:
<221> NAME/KEY: MOD_RES
<222> LOCATION: (3)
<223> OTHER INFORMATION: Xaa is Asn (N) or Ser (S)
<220> FEATURE:
<221> NAME/KEY: MOD_RES
<222> LOCATION: (5)
<223> OTHER INFORMATION: Xaa is Ser (S) or Ala (A)
<220> FEATURE:
<221> NAME/KEY: MOD_RES
<222> LOCATION: (7)
<223> OTHER INFORMATION: Xaa is Asn (N) or Lys (K)

<400> SEQUENCE: 20

Xaa Ile Xaa Tyr Xaa Gly Xaa Thr Asp Tyr Asn Pro Ser Leu Lys Ser
  1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Synthetic CDR-L1 of anti-Ang2 antibody
<220> FEATURE:
<221> NAME/KEY: MOD_RES
<222> LOCATION: (5)
<223> OTHER INFORMATION: Xaa is Ser (S) or Phe (F)
<220> FEATURE:
<221> NAME/KEY: MOD_RES
<222> LOCATION: (8)
<223> OTHER INFORMATION: Xaa is Asn (N) or Thr (T)
```

```
<220> FEATURE:
<221> NAME/KEY: MOD_RES
<222> LOCATION: (11)
<223> OTHER INFORMATION: Xaa is Ala (A) or His (H)

<400> SEQUENCE: 21

Lys Ala Ser Gln Xaa Val Ser Xaa Asp Val Xaa
 1               5                  10

<210> SEQ ID NO 22
<211> LENGTH: 7
<212> TYPE: PRT
<213> ORGANISM: Artificial Sequence
<220> FEATURE:
<223> OTHER INFORMATION: Synthetic CDR-L2 of anti-Ang2 antibody
<220> FEATURE:
<221> NAME/KEY: MOD_RES
<222> LOCATION: (4)
<223> OTHER INFORMATION: Xaa is Asn (N) or Ile (I)
<220> FEATURE:
<221> NAME/KEY: MOD_RES
<222> LOCATION: (5)
<223> OTHER INFORMATION: Xaa is Arg (R) or Pro (P)

<400> SEQUENCE: 22

Tyr Ala Ser Xaa Xaa Tyr Pro
 1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic CDR-L3 of anti-Ang2 antibody
<220> FEATURE:
<221> NAME/KEY: MOD_RES
<222> LOCATION: (2)
<223> OTHER INFORMATION: Xaa is Gln (Q) or His (H)
<220> FEATURE:
<221> NAME/KEY: MOD_RES
<222> LOCATION: (8)
<223> OTHER INFORMATION: Xaa is Trp (W) or Phe (F)

<400> SEQUENCE: 23

Gln Xaa Asp Tyr Ser Ser Pro Xaa Thr
 1               5

<210> SEQ ID NO 24
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of 10D6)

<400> SEQUENCE: 24

Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of VH-hu1)

<400> SEQUENCE: 25
```

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser
            20                  25                  30
```

<210> SEQ ID NO 26
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of VH-hu2)

<400> SEQUENCE: 26

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr
            20                  25                  30
```

<210> SEQ ID NO 27
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of VH-hu5)

<400> SEQUENCE: 27

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr
            20                  25                  30
```

<210> SEQ ID NO 28
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of VH-hu3)

<400> SEQUENCE: 28

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr
            20                  25                  30
```

<210> SEQ ID NO 29
<211> LENGTH: 14
<212> TYPE: PRT
<213> ORGANISM: Artificial Sequence
<220> FEATURE:
<223> OTHER INFORMATION: Synthetic FR2 (frame region between CDR-H1
      and CDR-H2 of 10D6)

<400> SEQUENCE: 29

```
Trp Ile Arg Gln Phe Pro Gly Asn Lys Leu Glu Trp Met Gly
 1               5                  10
```

<210> SEQ ID NO 30
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and CDR-H2 of VH-hu1)

<400> SEQUENCE: 30

Trp Ile Arg Gln Pro Pro Gly Lys Gly Leu Glu Trp Ile Gly
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu2)

<400> SEQUENCE: 31

Trp Ile Arg Gln Pro Pro Gly Lys Gly Leu Glu Trp Met Gly
 1               5                  10

<210> SEQ ID NO 32
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu5)

<400> SEQUENCE: 32

Trp Ile Arg Gln Pro Pro Gly Lys Gly Leu Glu Trp Ile Gly
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Synthetic FR2 (frame region between CDR-H1 and
      CDR-H2 of VH-hu3)

<400> SEQUENCE: 33

Trp Val Arg Gln Ala Pro Gly Lys Gly Leu Glu Trp Met Gly
 1               5                  10

<210> SEQ ID NO 34
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of 10D6)

<400> SEQUENCE: 34

Arg Ser Ser Ile Thr Arg Asp Thr Ser Lys Asn Gln Phe Phe Leu Gln
 1               5                  10                  15

Leu Asn Ser Val Thr Thr Gly Asp Thr Ala Thr Tyr Tyr Cys Ala Arg
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu1)

<400> SEQUENCE: 35

Arg Val Thr Ile Ser Val Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu2)

<400> SEQUENCE: 36

Arg Ser Thr Ile Ser Arg Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Synthetic FR3 (frame region between CDR-H2
      and CDR-H3 of VH-hu5)

<400> SEQUENCE: 37

Arg Val Thr Ile Ser Val Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Synthetic FR3 (frame region between CDR-H2 and
      CDR-H3 of VH-hu3)

<400> SEQUENCE: 38

Arg Ser Thr Ile Ser Arg Asp Thr Ser Lys Asn Thr Phe Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: Synthetic FR4 (C-terminal frame region of
      CDR-H3 of 10D6)

<400> SEQUENCE: 39

Trp Gly Gln Gly Thr Ser Val Thr Val Ser Ser
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Synthetic FR4 (C-terminal frame region of
      CDR-H3 of VH-hu1)

<400> SEQUENCE: 40

Trp Gly Gln Gly Thr Leu Val Thr Val Ser Ser
 1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic FR4 (C-terminal frame region of
      CDR-H3 of VH-hu2)

<400> SEQUENCE: 41

Trp Gly Gln Gly Thr Leu Val Thr Val Ser Ser
 1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic FR4 (C-terminal frame region of
      CDR-H3 of VH-hu5)

<400> SEQUENCE: 42

Trp Gly Gln Gly Thr Leu Val Thr Val Ser Ser
 1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic FR4 (C-terminal frame region of
      CDR-H3 of VH-hu3)

<400> SEQUENCE: 43

Trp Gly Gln Gly Thr Leu Val Thr Val Ser Ser
 1               5                   10

<210> SEQ ID NO 44
<211> LENGTH: 23
<212> TYPE: PRT
<213> ORGANISM: Artificial Sequence
<220> FEATURE:
<223> OTHER INFORMATION: Synthetic FR1 (N-terminal frame region of
      CDR-L1 of 10D6)

<400> SEQUENCE: 44

Ser Ile Val Met Thr Gln Thr Pro Lys Phe Leu Leu Val Ser Ala Gly
 1               5                   10                  15

Asp Arg Val Thr Ile Thr Cys
                20

<210> SEQ ID NO 45
<211> LENGTH: 23
<212> TYPE: PRT
<213> ORGANISM: Artificial Sequence
<220> FEATURE:
<223> OTHER INFORMATION: Synthetic FR1 (N-terminal frame region of
      CDR-L1 of VL-hu1)

<400> SEQUENCE: 45

Asp Ile Gln Met Thr Gln Ser Pro Ser Ser Leu Ser Ala Ser Val Gly
 1               5                   10                  15

Asp Arg Val Thr Ile Thr Cys
                20

```
<210> SEQ ID NO 46
<211> LENGTH: 15
<212> TYPE: PRT
<213> ORGANISM: Artificial Sequence
<220> FEATURE:
<223> OTHER INFORMATION: Synthetic FR2 (frame region between CDR-L1 and
      CDR-L2 of 10D6)

<400> SEQUENCE: 46

Trp Tyr Gln Gln Lys Pro Gly Gln Ser Pro Lys Leu Leu Ile Tyr
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic FR2 (frame region between CDR-L1 and
      CDR-L2 of VL-hu1)

<400> SEQUENCE: 47

Trp Tyr Gln Gln Lys Pro Gly Lys Ala Pro Lys Leu Leu Ile Tyr
 1               5                  10                  15

<210> SEQ ID NO 48
<211> LENGTH: 32
<212> TYPE: PRT
<213> ORGANISM: Artificial Sequence
<220> FEATURE:
<223> OTHER INFORMATION: Synthetic FR3 (frame region between CDR-L2 and
      CDR-L3 of 10D6)

<400> SEQUENCE: 48

Gly Val Pro Asp Arg Phe Thr Gly Ser Gly Tyr Gly Thr Asp Phe Thr
 1               5                  10                  15

Phe Thr Ile Ser Thr Val Gln Ala Glu Asp Leu Ala Val Tyr Phe Cys
                20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic FR3 (frame region between CDR-L2 and
      CDR-L3 of VL-hu1)

<400> SEQUENCE: 49

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
                20                  25                  30

<210> SEQ ID NO 50
<211> LENGTH: 10
<212> TYPE: PRT
<213> ORGANISM: Artificial Sequence
<220> FEATURE:
<223> OTHER INFORMATION: Synthetic FR4 (C-terminal frame region of
      CDR-L3 of 10D6)

<400> SEQUENCE: 50

Phe Gly Gly Gly Thr Lys Leu Glu Ile Lys
 1               5                  10

<210> SEQ ID NO 51
```

-continued

```
<211> LENGTH: 10
<212> TYPE: PRT
<213> ORGANISM: Artificial Sequence
<220> FEATURE:
<223> OTHER INFORMATION: Synthetic FR4 (C-terminal frame region of
      CDR-L3 of VL-hu1)

<400> SEQUENCE: 51

Phe Gly Gln Gly Thr Lys Val Glu Ile Lys
 1               5                  10

<210> SEQ ID NO 52
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 52

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 53

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Lys Ile Asn Tyr Ala Gly Asn Thr Asp Tyr Asn Pro Ser Leu
    50                  55                  60

Lys Ser Arg Ser Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115
```

```
<210> SEQ ID NO 54
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 54
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115

```
<210> SEQ ID NO 55
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 55
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Met Gly Lys Ile Asn Tyr Ala Gly Asn Thr Asp Tyr Asn Pro Ser Leu
    50                  55                  60

Lys Ser Arg Ser Thr Ile Ser Arg Asp Thr Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115

```
<210> SEQ ID NO 56
<211> LENGTH: 118
<212> TYPE: PRT
<213> ORGANISM: Artificial Sequence
<220> FEATURE:
<223> OTHER INFORMATION: Synthetic Heavy chain variable region

<400> SEQUENCE: 56
```

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Asn Tyr Ser Gly Asn Thr Asp Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Asn Phe Glu Gly Ala Met Asp Tyr Trp Gly Gln Gly Thr
        100                 105                 110

Leu Val Thr Val Ser Ser
            115

<210> SEQ ID NO 57
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
            85                  90                  95

Thr Phe Gly Gln Gly Thr Lys Leu Glu Ile Lys
        100                 105

<210> SEQ ID NO 58
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val His Trp Tyr Gln Gln Lys Pro Gly Lys Ala Pro Lys Leu Leu Ile
        35                  40                  45

Tyr Tyr Ala Ser Asn Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 59

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
                20                  25                  30

Val His Trp Tyr Gln Gln Lys Pro Gly Lys Ala Pro Lys Leu Leu Ile
            35                  40                  45

Tyr Tyr Ala Ser Asn Arg Tyr Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Asp Tyr Ser Ser Pro Phe
                85                  90                  95

Thr Phe Gly Gln Gly Thr Lys Leu Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 60

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Phe Val Ser Thr Asp
                20                  25                  30

Val His Trp Tyr Gln Gln Lys Pro Gly Lys Ala Pro Lys Leu Leu Ile
            35                  40                  45

Tyr Tyr Ala Ser Asn Arg Tyr Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 61

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
             20                  25                  30

Val Ala Trp Tyr Gln Gln Lys Pro Gly Lys Ala Pro Lys Leu Leu Ile
         35                  40                  45

Tyr Tyr Ala Ser Ile Pro Tyr Pro Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Leu Glu Ile Lys
                100                 105
```

<210> SEQ ID NO 62
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 62

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Ser Asn Asp
             20                  25                  30

Val His Trp Tyr Gln Gln Lys Pro Gly Lys Ala Pro Lys Leu Leu Ile
         35                  40                  45

Tyr Tyr Ala Ser Ile Pro Tyr Pro Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Leu Glu Ile Lys
                100                 105
```

<210> SEQ ID NO 63
<211> LENGTH: 107
<212> TYPE: PRT
<213> ORGANISM: Artificial Sequence
<220> FEATURE:
<223> OTHER INFORMATION: Synthetic Light chain variable resion

<400> SEQUENCE: 63

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Phe Val Ser Thr Asp
             20                  25                  30

Val His Trp Tyr Gln Gln Lys Pro Gly Lys Ala Pro Lys Leu Leu Ile
         35                  40                  45

Tyr Tyr Ala Ser Ile Pro Tyr Pro Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95
```

Thr Phe Gly Gln Gly Thr Lys Leu Glu Ile Lys
            100                 105

<210> SEQ ID NO 64
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 52)

<400> SEQUENCE: 64
caggtgcaac tgcaggagtc aggccccggc ctggtaaaac cttctgaaac gctctcactt      60
acctgtgccg ttagtggata ctctatcact tccgactacg cttggaattg gattcggcag     120
cctccaggca aagggctgga atggatggga aagatttcct attccggtaa gactgactac     180
aatcccagtc tgaagagcag gtcaacaatc tccagagaca ccagcaagaa tcagttttcc     240
ctgaaattgt cctcggtgac agcagcggat accgcagtgt attattgcgc ccgcggtaac     300
ttcgagggag ctatggatta ctgggggcag ggtactctcg tcactgtgag cagc            354

<210> SEQ ID NO 65
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 53)

<400> SEQUENCE: 65
caggtgcaac tgcaggagtc aggccccggc ctggtaaaac cttctgaaac gctctcactt      60
acctgtgccg ttagtggata ctctatcact tccgactacg cttggaattg gattcggcag     120
cctccaggca aagggctgga atggatggga aagattaact atgccggtaa cactgactac     180
aatcccagtc tgaagagcag gtcaacaatc tccagagaca ccagcaagaa tcagttttcc     240
ctgaaattgt cctcggtgac agcagcggat accgcagtgt attattgcgc ccgcggtaac     300
ttcgagggag ctatggatta ctgggggcag ggtactctcg tcactgtgag cagc            354

<210> SEQ ID NO 66
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 54)

<400> SEQUENCE: 66
gaggttcagc tggtcgaaag cggtggggga ctcgtgcagc caggcggttc tcttagatta      60
tcatgtgccg catccgggta ctccatcacc tctgattatg catggaactg ggtcagacaa     120
gcccccggaa agggcctgga gtggatgggg aagatctcct attcagggaa gacagattat     180
aatccttcgc tgaaaagcag atcaacaatt agtagagaca cttctaaaaa tacttttttac    240 ctccagatga acagtctgcg cgccgaagac accgccgtgt actactgcgc taggggaaat     300
ttcgagggag ctatggacta ttggggccag ggcacgttgg taaccgtgag cagc            354

<210> SEQ ID NO 67
<211> LENGTH: 354
<212> TYPE: DNA
<213> ORGANISM: Artificial Sequence
<220> FEATURE:

<223> OTHER INFORMATION: Synthetic Coding sequence of heavy chain
      variable region(SEQ ID NO: 55)

<400> SEQUENCE: 67
gaggttcaac tggtagagtc cggggcggc ctggtccagc caggaggaag cctgcggctc      60
tcttgtgccg ccagcgggta tagtatcact tcagattatg cctggaattg ggtccgccag     120
gcccccggga agggcttaga gtggatgggt aaaattaatt acgcaggcaa caccgactat     180
aatccttcac tgaaatctag atccaccatc tctagagata caagtaagaa cacctttttac    240 ttgcagatga atagcctcag ggctgaagac actgctgtgt actactgcgc aagaggaaac     300
ttcgaaggag cgatggatta ttggggccag ggtacgcttg tgacagtgtc ctct           354

<210> SEQ ID NO 68
<211> LENGTH: 354
<212> TYPE: DNA
<213> ORGANISM: Artificial Sequence
<220> FEATURE:
<223> OTHER INFORMATION: Synthetic Coding sequence of heavy chain
      variable region(SEQ ID NO: 56)

<400> SEQUENCE: 68
caggtgcagc tgcaggagtc gggcccagga ctggtgaagc cttcggagac cctgtccctc      60
acctgcgctg tctctggtta ctccatcacc agtgattatg cctggaactg gatccggcag     120
ccccagggga aggggctgga gtggattggg tacataaact acagtggtaa cactgactac     180
aacccatctc tcaaaagtcg agtcaccata tcagtagaca cgtccaagaa ccagttctcc     240
ctgaagctga gctctgtgac cgccgcagac acggccgtgt attactgtgc gagaggtaac     300
ttcgaaggtg ctatggacta ctggggtcaa ggaacgcttg tgacagtgtc ctct            354

<210> SEQ ID NO 69
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 57)

<400> SEQUENCE: 69
gacatccaga tgacccagtc tccatcctcc ctgtctgcat ctgtaggaga cagagtcacc      60
atcacttgca aggccagtca gagtgtgagt aatgatgtag cttggtatca gcagaaacca     120
gggaaagccc ctaagctcct gatctattat gcatccaatc gctaccctgg ggtcccatca     180
aggttcagtg gcagtggatc tgggacagat ttcactctca ccatcagcag tctgcaacct    240
gaagattttg caacttacta ctgtcagcag gattatagct ctccgtggac gttcggtgga     300
ggcaccaagg tggaaatcaa a                                               321

<210> SEQ ID NO 70
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 58)

<400> SEQUENCE: 70
gacatccaga tgacccagtc tccatcctcc ctgtctgcat ctgtaggaga cagagtcacc      60
atcacttgca aggccagtca gagtgtgagt aatgatgtac attggtatca gcagaaacca     120
gggaaagccc ctaagctcct gatctattat gcatccaatc gctaccctgg ggtcccatca     180

```
aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                              321
```

```
<210> SEQ ID NO 71
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 59)

<400> SEQUENCE: 71
```

```
gacatccaga tgacccagtc tccatcctcc ctgtctgcat ctgtaggaga cagagtcacc     60
atcacttgca aggccagtca gagtgtgagt aatgatgtac attggtatca gcagaaacca    120
gggaaagccc ctaagctcct gatctattat gcatccaatc gctaccctgg ggtcccatca    180
aggttcagtg gcagtggatc tgggacagat ttcactctca ccatcagcag tctgcaacct    240
gaagattttg caacttacta ctgtcagcat gattatagct ctccgttcac gttcggtgga    300
ggcaccaagg tggaaatcaa a                                              321
```

```
<210> SEQ ID NO 72
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 60)

<400> SEQUENCE: 72
```

```
gacatccaga tgacccagtc tccatcctcc ctgtctgcat ctgtaggaga cagagtcacc     60
atcacttgca aggccagtca gttcgtgagt actgatgtac attggtatca gcagaaacca    120
gggaaagccc ctaagctcct gatctattat gcatccaatc gctaccctgg ggtcccatca    180
aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                              321
```

```
<210> SEQ ID NO 73
<211> LENGTH: 321
<212> TYPE: DNA
<213> ORGANISM: Artificial Sequence
<220> FEATURE:
<223> OTHER INFORMATION: Synthetic Coding sequence of light chain
      variable region(SEQ ID NO: 61)

<400> SEQUENCE: 73
```

```
gacatccaga tgacccagtc tccatcctcc ctgtctgcat ctgtaggaga cagagtcacc     60
atcacttgca aggccagtca gagtgtgagt aatgatgtag cttggtatca gcagaaacca    120
gggaaagccc ctaagctcct gatctattat gcatccatcc cataccctgg ggtcccatca    180
aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                              321
```

```
<210> SEQ ID NO 74
<211> LENGTH: 321
```

<212> TYPE: DNA
<213> ORGANISM: Artificial Sequence
<220> FEATURE:
<223> OTHER INFORMATION: Synthetic Coding sequence of light chain variable region(SEQ ID NO: 62)

<400> SEQUENCE: 74

```
gacatccaga tgacccagtc tccatcctcc ctgtctgcat ctgtaggaga cagagtcacc      60
atcacttgca aggccagtca gagtgtgagt aatgatgtac attggtatca gcagaaacca    120
gggaaagccc ctaagctcct gatctattat gcatccatcc ataccctgg ggtcccatca    180
aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                              321
```

<210> SEQ ID NO 75
<211> LENGTH: 321
<212> TYPE: DNA
<213> ORGANISM: Artificial Sequence
<220> FEATURE:
<223> OTHER INFORMATION: Synthetic Coding sequence of light chain variable region(SEQ ID NO: 63)

<400> SEQUENCE: 75

```
gacatccaga tgacccagtc tccatcctcc ctgtctgcat ctgtaggaga cagagtcacc      60
atcacttgca aggccagtca gttcgtgagt actgatgtac attggtatca gcagaaacca    120
gggaaagccc ctaagctcct gatctattat gcatccatcc ataccctgg ggtcccatca    180
aggttcagtg gcagtggatc tgggacagat ttcactctca ccatcagcag tctgcaacct    240
gaagattttg caacttacta ctgtcagcag gattatagct ctccgtggac gttcggtgga    300
ggcaccaagg tggaaatcaa a                                              321
```

<210> SEQ ID NO 76
<211> LENGTH: 15
<212> TYPE: PRT
<213> ORGANISM: Artificial Sequence
<220> FEATURE:
<223> OTHER INFORMATION: Synthetic Linker

<400> SEQUENCE: 76

Gly Gly Gly Gly Ser Gly Gly Gly Gly Ser Gly Gly Gly Gly Ser
1               5                   10                  15

<210> SEQ ID NO 77
<211> LENGTH: 118
<212> TYPE: PRT
<213> ORGANISM: Artificial Sequence
<220> FEATURE:
<223> OTHER INFORMATION: Synthetic 10D6-HU1

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Asp
                20                  25                  30

Tyr Ala Trp Asn Trp Ile Arg Gln Pro Pro Gly Lys Gly Leu Glu Trp
            35                  40                  45

Ile Gly Tyr Ile Asn Tyr Ser Gly Asn Thr Asp Tyr Asn Pro Ser Leu
        50                  55                  60

Lys Ser Arg Val Thr Ile Ser Val Asp Thr Ser Lys Asn Gln Phe Ser

```
                65                  70                  75                  80
Leu Lys Leu Ser Ser Val Thr Ala Ala Asp Thr Ala Val Tyr Tyr Cys
                    85                  90                  95

Ala Arg Gly Asn Phe Glu Gly Ala Met Asp Tyr Trp Gly Gln Gly Thr
                100                 105                 110

Leu Val Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: Synthetic 10D6-HU2

<400> SEQUENCE: 78

Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Thr Ser Asp
             20                  25                  30

Tyr Ala Trp Asn Trp Ile Arg Gln Pro Pro Gly Lys Gly Leu Glu Trp
         35                  40                  45

Met Gly Tyr Ile Asn Tyr Ser Gly Asn Thr Asp Tyr Asn Pro Ser Leu
 50                  55                  60

Lys Ser Arg Ser Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Asn Phe Glu Gly Ala Met Asp Tyr Trp Gly Gln Gly Thr
                100                 105                 110

Leu Val Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Synthetic 10D6-HU3

<400> SEQUENCE: 79

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Ile Thr Ser Asp
             20                  25                  30

Tyr Ala Trp Asn Trp Val Arg Gln Ala Pro Gly Lys Gly Leu Glu Trp
         35                  40                  45

Met Gly Tyr Ile Asn Tyr Ser Gly Asn Thr Asp Tyr Asn Pro Ser Leu
 50                  55                  60

Lys Ser Arg Ser Thr Ile Ser Arg Asp Thr Ser Lys Asn Thr Phe Tyr
 65                  70                  75                  80

Leu Gln Met Asn Ser Leu Arg Ala Glu Asp Thr Ala Val Tyr Tyr Cys
                 85                  90                  95

Ala Arg Gly Asn Phe Glu Gly Ala Met Asp Tyr Trp Gly Gln Gly Thr
                100                 105                 110

Leu Val Thr Val Ser Ser
        115
```

<210> SEQ ID NO 80
<211> LENGTH: 240
<212> TYPE: PRT
<213> ORGANISM: Artificial Sequence
<220> FEATURE:
<223> OTHER INFORMATION: Synthetic VH-linker-VL (scFv) of 10D6

<400> SEQUENCE: 80

```
Asp Val Gln Leu Gln Glu Ser Gly Pro Asp Leu Val Lys Pro Ser Gln
  1               5                  10                  15

Ser Leu Ser Leu Thr Cys Thr Val Thr Gly Tyr Ser Ile Thr Ser Asp
             20                  25                  30

Tyr Ala Trp Asn Trp Ile Arg Gln Phe Pro Gly Asn Lys Leu Glu Trp
         35                  40                  45

Met Gly Tyr Ile Asn Tyr Ser Gly Asn Thr Asp Tyr Asn Pro Ser Leu
 50                  55                  60

Lys Ser Arg Ser Ser Ile Thr Arg Asp Thr Ser Lys Asn Gln Phe Phe
 65                  70                  75                  80

Leu Gln Leu Asn Ser Val Thr Thr Gly Asp Thr Ala Thr Tyr Tyr Cys
                 85                  90                  95

Ala Arg Gly Asn Phe Glu Gly Ala Met Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Ser Ile Val Met Thr Gln Thr Pro Lys Phe Leu
130                 135                 140

Leu Val Ser Ala Gly Asp Arg Val Thr Ile Thr Cys Lys Ala Ser Gln
145                 150                 155                 160

Ser Val Ser Asn Asp Val Ala Trp Tyr Gln Gln Lys Pro Gly Gln Ser
                165                 170                 175

Pro Lys Leu Leu Ile Tyr Tyr Ala Ser Asn Arg Tyr Pro Gly Val Pro
            180                 185                 190

Asp Arg Phe Thr Gly Ser Gly Tyr Gly Thr Asp Phe Thr Phe Thr Ile
        195                 200                 205

Ser Thr Val Gln Ala Glu Asp Leu Ala Val Tyr Phe Cys Gln Gln Asp
    210                 215                 220

Tyr Ser Ser Pro Trp Thr Phe Gly Gly Gly Thr Lys Leu Glu Ile Lys
225                 230                 235                 240
```

<210> SEQ ID NO 81
<211> LENGTH: 720
<212> TYPE: DNA
<213> ORGANISM: Artificial Sequence
<220> FEATURE:
<223> OTHER INFORMATION: Synthetic Coding sequence of VH-linker-VL (scFv) of 10D6

<400> SEQUENCE: 81

```
gatgtgcagc ttcaggagtc gggacctgac ctggtgaaac cttctcagtc tctgtccctc      60
acctgcactg tcactggcta ctcaatcacc agtgattatg cctggaactg gatccggcag     120
tttccaggaa acaaactgga gtggatgggc tacataaact acagtggtaa cactgactac     180
aacccatctc tcaaaagtcg aagctctatc actcgagaca catccaagaa ccagttcttc     240
ctgcagttga attctgtgac tactggggac acagccacat attactgtgc aagaggtaac     300
ttcgaaggtg ctatggacta ctggggtcaa ggaacctcag tcaccgtctc ctcaggcggc     360
ggcggcagcg gcggcggcgg cagcggcggc ggcggcagca gtattgtgat gacccagact     420
```

```
cccaaattcc tgcttgtatc agcaggagac agggttacca taacctgcaa ggccagtcag    480
agtgtgagta atgatgtagc ttggtaccaa cagaagccag ggcagtctcc taaactgctg    540
atatactatg catccaatcg ctaccctgga gtccctgatc gcttcactgg cagtggatat    600
gggacggatt tcactttcac catcagcact gtgcaggctg aagacctggc agtttatttc    660
tgtcagcagg attatagctc tccgtggacg ttcggtggag gcaccaagct ggaaatcaaa    720
```

<210> SEQ ID NO 82
<211> LENGTH: 240
<212> TYPE: PRT
<213> ORGANISM: Artificial Sequence
<220> FEATURE:
<223> OTHER INFORMATION: Synthetic VH-linker-VL (scFv) of10D6 opti-1

<400> SEQUENCE: 82

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Thr Ser Asp
             20                  25                  30

Tyr Ala Trp Asn Trp Ile Arg Gln Pro Pro Gly Lys Gly Leu Glu Trp
         35                  40                  45

Met Gly Lys Ile Ser Tyr Ser Gly Lys Thr Asp Tyr Asn Pro Ser Leu
 50                  55                  60

Lys Ser Arg Ser Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Asn Phe Glu Gly Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Ser Val Ser Asn Asp Val Ala Trp Tyr Gln Gln Lys Pro Gly Lys Ala
                165                 170                 175

Pro Lys Leu Leu Ile Tyr Tyr Ala Ser Asn Arg Tyr Pro Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Asp
    210                 215                 220

Tyr Ser Ser Pro Trp Thr Phe Gly Gln Gly Thr Lys Leu Glu Ile Lys
225                 230                 235                 240
```

<210> SEQ ID NO 83
<211> LENGTH: 720
<212> TYPE: DNA
<213> ORGANISM: Artificial Sequence
<220> FEATURE:
<223> OTHER INFORMATION: Synthetic Coding sequence of VH-linker-VL
      (scFv) of10D6 opti-1

<400> SEQUENCE: 83

```
caggtgcaac tgcaggagtc aggccccggc ctggtaaaac cttctgaaac gctctcactt    60
```

```
acctgtgccg ttagtggata ctctatcact tccgactacg cttggaattg gattcggcag    120
cctccaggca aagggctgga atggatggga aagatttcct attccggtaa gactgactac    180
aatcccagtc tgaagagcag gtcaacaatc tccagagaca ccagcaagaa tcagttttcc    240
ctgaaattgt cctcggtgac agcagcggat accgcagtgt attattgcgc cgcggtaac     300 ttcgagggag ctatggatta ctgggggcag ggtactctcg tcactgtgag cagcggcggc    360
ggcggcagcg gcggcggcgg cagcggcggc ggcggcagcg acatccagat gacccagtct    420
ccatcctccc tgtctgcatc tgtaggagac agagtcacca tcacttgcaa ggccagtcag    480
agtgtgagta atgatgtagc ttggtatcag cagaaaccag ggaaagcccc taagctcctg    540
atctattatg catccaatcg ctaccctggg gtcccatcaa ggttcagtgg cagtggatct    600
gggacagatt tcactctcac catcagcagt ctgcaacctg aagattttgc aacttactac    660
tgtcagcagg attatagctc tccgtggacg ttcggtggag gcaccaaggt ggaaatcaaa    720
```

<210> SEQ ID NO 84
<211> LENGTH: 118
<212> TYPE: PRT
<213> ORGANISM: Artificial Sequence
<220> FEATURE:
<223> OTHER INFORMATION: Synthetic Amino acid sequence of heavy chain
      variable region

<400> SEQUENCE: 84

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Asn Thr Asp Tyr Asn Pro Ser Leu
    50                  55                  60

Lys Ser Arg Ser Ser Ile Thr Arg Asp Thr Ser Lys Asn Gln Phe Phe
65                  70                  75                  80

Leu Gln Leu Asn Ser Val Thr Thr Gly Asp Thr Ala Thr Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115

<210> SEQ ID NO 85
<211> LENGTH: 30
<212> TYPE: PRT
<213> ORGANISM: Artificial Sequence
<220> FEATURE:
<223> OTHER INFORMATION: Synthetic FR1 (N-terminal frame region of
      CDR-H1 of 10D6)

<400> SEQUENCE: 85

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr
            20                  25                  30

<210> SEQ ID NO 86
<211> LENGTH: 11
<212> TYPE: PRT
<213> ORGANISM: Artificial Sequence

```
<220> FEATURE:
<223> OTHER INFORMATION: Synthetic FR4 (C-terminal frame region of
      CDR-H3 of 10D6)

<400> SEQUENCE: 86

Trp Gly Gln Gly Thr Leu Val Thr Val Ser Ser
 1               5                  10

<210> SEQ ID NO 87
<211> LENGTH: 107
<212> TYPE: PRT
<213> ORGANISM: Artificial Sequence
<220> FEATURE:
<223> OTHER INFORMATION: Synthetic Light chain variable region

<400> SEQUENCE: 87

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gly Gln Asp Tyr Ala Ser Pro Trp
                85                  90                  95

Thr Phe Gly Gln Gly Thr Lys Leu Glu Ile Lys
            100                 105

<210> SEQ ID NO 88
<211> LENGTH: 321
<212> TYPE: DNA
<213> ORGANISM: Artificial Sequence
<220> FEATURE:
<223> OTHER INFORMATION: Synthetic Nucleotide sequence coding VL
      (h10D6-OPTI-64)

<400> SEQUENCE: 88
gacatccaga tgacccagtc tccatcctcc ctgtctgcat ctgtaggaga cagagtcacc      60
atcacttgca aggccagtca gagtgtgagt aatgatgtag cttggtatca gcagaaacca     120
gggaaagccc ctaagctcct gatctattat gcatccaacc gatacccggg gtcccatca     180 aggttcagtg gcagtggatc tgggacagat ttcactctca ccatcagcag tctgcaacct     240
gaagattttg caacttacta ctgtggacag gattatgcct ctccgtggac gttcggtgga     300
ggcaccaagg tggaaatcaa a                                              321

<210> SEQ ID NO 89
<211> LENGTH: 107
<212> TYPE: PRT
<213> ORGANISM: Artificial Sequence
<220> FEATURE:
<223> OTHER INFORMATION: Synthetic Light chain variable region

<400> SEQUENCE: 89

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
            20                  25                  30
```

```
Val His Trp Tyr Gln Gln Lys Pro Gly Lys Ala Pro Lys Leu Leu Ile
            35                  40                  45

Tyr Tyr Ala Ser Asn Arg Tyr Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Asp Tyr Ser Ala Pro Trp
                85                  90                  95

Thr Phe Gly Gln Gly Thr Lys Leu Glu Ile Lys
            100                 105

<210> SEQ ID NO 90
<211> LENGTH: 321
<212> TYPE: DNA
<213> ORGANISM: Artificial Sequence
<220> FEATURE:
<223> OTHER INFORMATION: Synthetic Nucleotide sequence coding VL
      (h10D6-OPTI-66)

<400> SEQUENCE: 90
gacatccaga tgacccagtc tccatcctcc ctgtctgcat ctgtaggaga cagagtcacc    60
atcacttgca aggccagtca gagtgtgagt aatgatgtac actggtatca gcagaaacca   120
gggaaagccc ctaagctcct gatctattat gcatccaacc gatacctgg ggtcccatca    180 aggttcagtg gcagtggatc tgggacagat ttcactctca ccatcagcag tctgcaacct   240
gaagattttg caacttacta ctgtggacag gattattctg ccccgtggac gttcggtgga   300
ggcaccaagg tggaaatcaa a                                              321

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Gly Gln Asp Tyr Ala Ser Pro Trp Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Gly Gln Asp Tyr Ser Ala Pro Trp Thr
1               5
```

HUMANIZED OR AFFINITY-MATURED ANTI ANG-2 ANTIBODY AND USES THEREOF

CROSS-REFERENCE TO RELATED APPLICATIONS

This application claims the benefit of Korean Patent Application No. 10-2014-0063251 filed on May 26, 2014 in the Korean Intellectual Property Office, the entire disclosure of which is herein incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 59,982 byte ASCII (Text) file named "720430_ST25-Revised," created Sep. 7, 2017.

BACKGROUND OF THE INVENTION

1. Field

An anti-Ang2 antibody or an antigen-binding fragment thereof that specifically binds to an angiogenesis-inducing factor Angiopoietin-2 (Ang2) and complexes with a Tie2 receptor through Ang2, and methods of using the same, are provided.

2. Description of the Related Art

Angiogenesis refers to a mechanism through which a new blood vessel is formed from a pre-existing blood vessel, and has been known to play an important role in, e.g., the formation of organs, promoting normal physiological growth, promoting wound healing and the like. Abnormal angiogenesis has been known to play a crucial role in diseases such as tumor growth and metastasis, age-related macular degeneration, diabetic retinopathy, psoriasis, rheumatoid arthritis, and chronic inflammation.

Angiogenesis has been known to play an important role in tumor growth and metastasis, and various intensive researches on angiogenesis mechanism for developing a new cancer drug have been going on by developed countries and multinational pharmaceutical companies. One of the proteins that have been the target of research is Angiopoietin which has been known to be involved in blood vessel development and angiogenesis after birth. Known members of the angiopoietin family include Ang-1, 2, 3 and 4.

Angiogenesis related to Angiopoietin-2 (Ang2) in a cancer tissue is believed to occur as follows. First, for angiogenesis in the cancer tissue, cooption wherein cancer cells select pre-existing blood vessels to form new blood vessels in a cancer tissue occurs. Thereafter, blood vessel regression during which the functions of the pre-existing blood vessels are destroyed by Ang2 pathway occurs. The regression of the pre-existing vessels causes hypoxic environment within the cancer tissue, which is an environment where the formation of new blood vessels is possible. Under such conditions, the expression of vascular endothelial cell growth factor (VEGF) is increased, and new blood vessels are thus formed.

Thus, Ang2 is of increasing importance as a target for developing an angiogenesis inhibitor, and there is a need of developing an effective and strong Ang2 targeting substance.

BRIEF SUMMARY OF THE INVENTION

Provided is an anti-Ang2 antibody or an antigen-binding fragment thereof that specifically binds to an angiogenesis-inducing factor Ang2 (Angiopoietin-2) and forms a complex with a Tie2 receptor via Ang2 to induce the activation of the Tie2 receptor. The anti-Ang2 antibody can be humanized and/or affinity-matured.

In one embodiment, the anti-Ang2 antibody or an antigen-binding fragment thereof may comprise or consist essentially of:

a heavy chain variable region comprising a polypeptide (CDR-H1) comprising SEQ ID NO: 1, a polypeptide (CDR-H2) comprising SEQ ID NO: 20, and a polypeptide (CDR-H3) comprising SEQ ID NO: 3;

a light chain variable region comprising a polypeptide (CDR-L1) comprising SEQ ID NO: 21, a polypeptide (CDR-L2) comprising SEQ ID NO: 22, and a polypeptide (CDR-L3) comprising SEQ ID NO: 23; or a combination of the heavy chain variable region and the light chain variable region, with the proviso that the anti-Ang2 antibody or an antigen-binding fragment thereof does not comprise all of a polypeptide (CDR-H1) comprising SEQ ID NO: 1, a polypeptide (CDR-H2) comprising SEQ ID NO: 2, a polypeptide (CDR-H3) comprising SEQ ID NO: 3, a polypeptide (CDR-L1) comprising SEQ ID NO: 4, a polypeptide (CDR-L2) comprising SEQ ID NO: 5, and a polypeptide (CDR-L3) comprising SEQ ID NO: 6.

Another embodiment provides a pharmaceutical composition including the anti-Ang2 antibody or an antigen-binding fragment thereof and a carrier.

Another embodiment provides a method for inhibiting angiogenesis, including administering the anti-Ang2 antibody or an antigen-binding fragment thereof to a subject in need of inhibiting angiogenesis.

Another embodiment provides a method for decreasing vascular permeability, including administering the anti-Ang2 antibody or an antigen-binding fragment thereof to a subject in need of decreasing vascular permeability.

Another embodiment provides a method for inducing normal blood vessel formation, including administering the anti-Ang2 antibody or an antigen-binding fragment thereof to a subject in need of inducing normal blood vessel formation.

Another embodiment provides a method for preventing and/or treating a disease associated with angiogenesis, an increase in vascular permeability, and/or a decrease in normal blood vessel formation, including administering the anti-Ang2 antibody or an antigen-binding fragment thereof to a subject in need of preventing and/or treating a disease associated with angiogenesis, an increase in vascular permeability.

Another embodiment provides a method for inhibiting Ang2 and/or activating Tie2 receptor, including administering the anti-Ang2 antibody or an antigen-binding fragment thereof to a subject in need of inhibiting Ang2 and/or activating Tie2 receptor.

Another embodiment provides a method for detecting Ang2 and/or diagnosing a disease associated with overexpression of Ang2, using the anti-Ang2 antibody or an antigen-binding fragment thereof.

Another embodiment provides a complex including the anti-Ang2 antibody or an antigen-binding fragment thereof and Ang2, wherein the anti-Ang2 antibody or an antigen-binding fragment thereof binds to Ang2.

Another embodiment provides a pharmaceutical composition including the complex including the anti-Ang2 antibody or an antigen-binding fragment thereof and Ang2 and a carrier.

Another embodiment provides a method for activating Tie2 receptor, including administering the complex including the anti-Ang2 antibody or an antigen-binding fragment and Ang2 to a subject in need of activating Tie2 receptor.

Another embodiment provides a complex including the anti-Ang2 antibody or an antigen-binding fragment thereof, Ang2, and Tie2 receptor, wherein the anti-Ang2 antibody or an antigen-binding fragment thereof is bound to Ang2, and Ang2 is bound to Tie2 receptor, to form a complex.

Another embodiment provides a hybridoma cell line that produces an anti-Ang2 antibody or antigen-binding fragment thereof.

Another embodiment provides a polynucleotide encoding an anti-Ang2 antibody or antigen binding fragment thereof, optionally in a vector.

Another embodiment provides a method of preparing the anti-Ang2 antibody or antigen-binding fragment thereof by expressing a polynucleotide encoding the antibody or antigen-binding fragment in a cell.

BRIEF DESCRIPTION OF THE DRAWINGS

In FIG. 2, the upper graph shows the results of cells treated 6 nM of anti-Ang2 antibody and 4 nM of Ang2 protein; and the lower graph shows the results of cells treated with 1.2 nM of anti-Ang2 antibody and 4 nM of Ang2 protein.

DETAILED DESCRIPTION OF THE INVENTION

Figure 1:
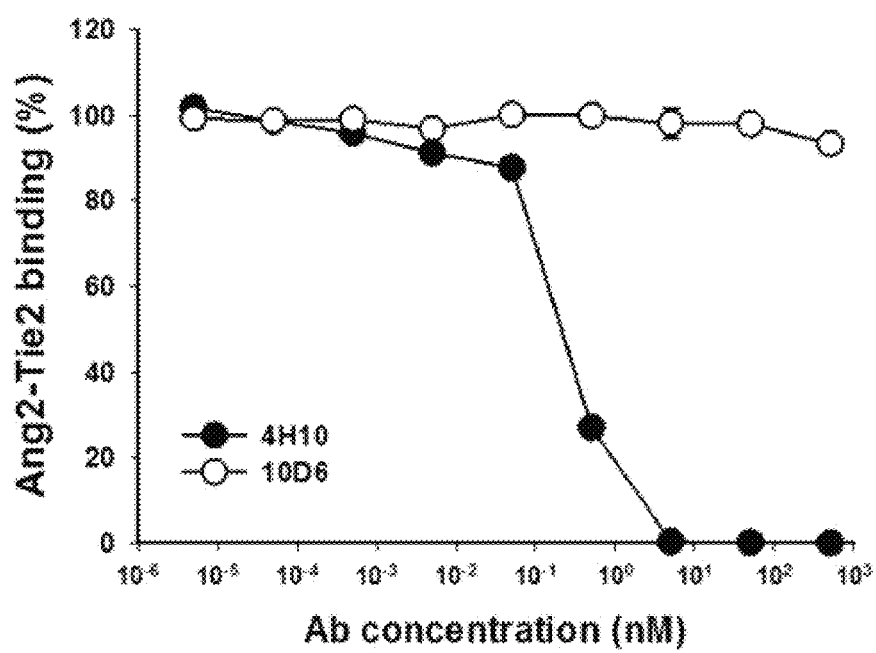
FIG. 1 is a graph showing the binding level between Tie2 receptor and Ang2 according to the concentration of anti-Ang2 antibody 10D6 measured by Ang2-Tie2 competition ELISA, indicating that the anti-Ang2 antibody 10D6 does not inhibit the binding between Tie2 receptor and Ang2.

It is found that an antibody which specifically binds to Ang2 but does not inhibit binding between Ang2 and a Tie2 receptor and forms a complex (antibody/Ang2/Tie2) together with Ang2 and the Tie2 receptor has a characteristic of inducing the dimerization of the antibody. Through this, it can induce the activation of the Tie2 receptor and its downstream signaling by effectively clustering the Tie2 receptor in the antibody/Ang2/Tie2 complex. The anti-Ang2 antibody inhibits Ang2 and has a dual function of Ang2 neutralization (inhibition of angiogenesis) and the normalization of blood vessels; that is, the antibody binds to Ang2 to induce the intracellular internalization and degradation thereof, thereby lowering the level of circulating Ang2, and at the same time, it induces Tie2 downstream signaling by binding to a Tie2 receptor via (i.e., indirectly to) Ang2 to activate the Tie2 receptor, similarly to Ang1, and induces the normalization of blood vessels. The normalization of blood vessels refers to the process by which abnormally formed blood vessels in cancer cells are converted into a structurally and functionally normal status; that is, the blood vessels in cancer cells regain normal structure and have decreased vascular permeability, and thus recover their normal function performance abilities.

Provided is an antibody targeting an angiogenesis-inducing factor Ang2 and particularly, an anti-Ang2 antibody or its humanized and/or affinity-matured form, which not only inhibits the functions of Ang2 by specifically binding to Ang2 thereby inhibiting angiogenesis and decreasing density of blood vessels in tumor tissue but also induces the activation of Tie2 by allowing anti-Ang2 antibody-bound Ang2 to bind Tie2, thereby structurally and/or functionally normalizing the blood vessels. The anti-Ang2 antibody or its humanized and/or affinity-matured form may bind Ang2 in such a way that Ang2 may still bind with Tie2. The anti-Ang2 antibody or its humanized and/or affinity-matured form may not directly bind to Tie2 receptor, but it can form a complex with Tie2 by binding Ang2 which, in turn, binds Tie2 receptor. The anti-Ang2 antibody or its humanized and/or affinity-matured form has the effects of treating diseases by binding to a Tie2 receptor together with Ang2 to activate the Tie2 receptor and thus induce the structural/functional normalization of blood vessels, along with the down-regulation of Ang2 in diseases related to the dysfunction and the abnormal activation of blood vessels such as cancer, sepsis, eye disorders, etc.

One embodiment provides an anti-Ang2 antibody or an antigen-binding fragment thereof, specifically recognizing and/or binding to an angiogenesis-inducing factor Ang2 (Angiopoietin-2) and binding to a Tie2 receptor via Ang2. Also, the anti-Ang2 antibody or an antigen-binding fragment thereof may induce the activation of the Tie2 receptor. Such activation of Tie2 receptor may be induced by an increase in the phosphorylation of Tie2 receptor and/or the phosphorylation of proteins related to the downstream signal pathway thereof, for example, at least one selected from the group consisting of Akt (NM_005163), eNOS (NM_000603), 42/44 (NM_002745), etc. Also, the anti-Ang2 antibody or an antigen-binding fragment thereof may induce the intracellular internalization of a Tie2 receptor. In other words, the anti-Ang2 antibody or an antigen-binding fragment thereof may bind to Ang2 and the Tie2 receptor via Ang2 to form a complex and induce the activation of the Tie2 receptor, by not inhibiting binding between Ang2 and the Tie2 receptor while specifically binding to Ang2, unlike other types of anti-Ang2 antibodies. Therefore, the anti-Ang2 antibody or an antigen-binding fragment thereof may increase the phosphorylation of a protein related to the downstream signal pathway of Tie2 receptor, such as at least one selected from the group consisting of Akt, eNOS, and 42/44, compared to the case using other anti-Ang2 antibodies that inhibit the binding between Ang2 and Tie2 receptor, such as antibody 4H10 (SEQ ID NOs: 12 & 13), etc.

The anti-Ang2 antibody may be humanized and/or affinity-matured, thereby having more increased binding affinity to Ang2 and more effective functions.

The Ang2 protein which functions as an antigen against the antibody is closely related to angiogenesis, and as a soluble ligand present in blood, it is widely involved in angiogenesis, metastasis, cancer cell invasion, etc. The Ang2 may be derived from mammals including primates such as humans and monkeys and rodents such as rats and mice and for example, it may be human Ang2 (e.g., NCBI Accession No. O15123, etc.), monkey Ang2 (e.g., NCBI Accession No. Q8MIK6, etc.), mouse Ang2 (e.g., NCBI Accession No. O35608, etc.), and rat Ang2 (e.g., NCBI Accession No. O35462, etc.), but is not limited thereto.

The Tie2 receptor (TEK tyrosine kinase), which is an Angiopoietin-1 receptor, is expressed in vascular endothelial cells in various mammals such as mouse (NM_013690; NP_038718), rat, and human (NM_000459; NP_000450), and is involved in various downstream signaling.

As explained above, the anti-Ang2 antibody or an antigen-binding fragment thereof is characterized in that the antibody which specifically binds to Ang2 but does not inhibit binding between Ang2 and Tie2 receptor and forms a complex (antibody/Ang2/Tie2) together with Ang2 and the Tie2 receptor, has a characteristic of inducing the dimerization of the antibody, and through this, it can induce the activation of the Tie2 receptor and its downstream signaling by effectively clustering the Tie2 receptor which constitutes the complex. By virtue of such an action mechanism, the anti-Ang2 antibody and the antigen-binding fragment thereof inhibits Ang2 functions by binding to Ang2 to induce the intracellular internalization and degradation thereof and thus lowers the level of circulating Ang2 and at the same time, it induces Tie2 downstream signaling by binding to the Tie2 receptor together with Ang2 to activate the Tie2 receptor, like Ang1 and induces the stabilization of vascular endothelial cells. By having such dual functions, the antibody and the antigen-binding fragment thereof can be usefully employed to treat not only symptoms (disorders) due to the overexpression of Ang2 but also symptoms (disorders) due to the decrease in the stabilization of vascular endothelial cells, that is, the increase of vascular penetration.

The anti-Ang2 antibody or an antigen-binding fragment thereof may recognize all or part (for example, at least one amino acid selected from the group consisting of the amino acid residues exposed to the outside) of loop 1 (of SEQ ID NO: 11, a site from 417$^{th}$ amino acid to 434$^{th}$ amino acid) of human Ang2 (hAng2; SEQ ID NO: 11; Accession #O15123) or an amino acid sequence site including about 2 to about 20, about 2 to about 15, 2 to about 10, or about 2 to about 5 contiguous amino acids including at least one exposed amino acid residue of loop 1 of SEQ ID NO: 11 as an epitope. As used herein, the term "exposed" amino acid is an amino acid that is exposed to solution (e.g., a biological medium or other solution) and available for binding when a protein (e.g., Ang2) is in its native conformation in a biological medium or other solution under physiological conditions (e.g., physiological pH, isotonicity, temperature, etc.)

```
Ang2
                                       (SEQ ID NO: 11)
MWQIVFFTLS CDLVLAAAYN NFRKSMDSIG KKQYQVQHGS

CSYTFLLPEM DNCRSSSSPY VSNAVQRDAP LEYDDSVQRL

QVLENIMENN TQWLMKLENY IQDNMKKEMV EIQQNAVQNQ

TAVMIEIGTN LLNQTAEQTR KLTDVEAQVL NQTTRLELQL

LEHSLSTNKL EKQILDQTSE INKLQDKNSF LEKKVLAMED

KHIIQLQSIK EEKDQLQVLV SKQNSIIEEL EKKIVTATVN
```

-continued
```
NSVLQKQQHD LMETVNNLLT MMSTSNSAKD PTVAKEEQIS

FRDCAEVFKS GHTTNGIYTL TFPNSTEEIK AYCDMEAGGG

GWTIIQRRED GSVDFQRTWK EYKVGFGNPS GEYWLGNEFV

SQLTNQQRYV LKIHLKDWEG NEAYSLYEHF YLSSEELNYR

IHLKGLTGTA GKISSISQPG NDFSTKDGDN DKCICKCSQM

LTGGWWFDAC GPSNLNGMYY PQRQNTNKFN GIKWYYWKGS

GYSLKATTMM IRPADF
```

For example, the anti-Ang2 antibody may recognize Q418, P419, a combination of Q418 and P419 positioned at loop 1 of SEQ ID NO: 11, or an amino acid sequence site including about 2 to about 20, about 2 to about 15, about 2 to about 10, or about 2 to about 5 contiguous amino acids including the amino acid residue of Q418, P419, or combination of Q418 and P419 of SEQ ID NO: 11, as an epitope, or specifically bind to this site. In one embodiment, the anti-Ang2 antibody may recognize the amino acid residues of Q418 and P419 of SEQ ID NO: 11 as an epitope, or specifically bind to this portion.

Q418, P419, or an amino acid sequence (epitope) including them, to which the anti-Ang2 antibody specifically binds, are exposed amino acid residues positioned in loop 1 of the three dimensional structure of Ang2, and they do not participate in binding between Ang2 and Tie2 receptor.

In Q418, P419, or an amino acid sequence (epitope) including them, to which the anti-Ang2 antibody specifically binds, the term "contiguous amino acids" may refer to not only amino acids which are consecutive on primary structure, but also amino acids which are adjacent to one another on the secondary, or tertiary structure of a protein.

Therefore, the anti-Ang2 antibody or an antigen-binding fragment thereof may be (1) an anti-Ang2 antibody or an antigen-binding fragment that specifically recognizes and/or binds to the above described site as an epitope, or (2) a humanized and/or affinity-matured anti-Ang2 antibody or an antigen-binding fragment of the anti-Ang2 antibody or an antigen-binding fragment of (1).

In a particular embodiment, the anti-Ang2 antibody or an antigen-binding fragment thereof may comprise or consist essentially of:

at least one heavy chain complementarity determining region (CDR) selected from the group consisting of a polypeptide (CDR-H1) including the amino acid sequence of SEQ ID NO: 1, a polypeptide (CDR-H2) including the amino acid sequence of SEQ ID NO: 2, and a polypeptide (CDR-H3) including the amino acid sequence of SEQ ID NO: 3, or a heavy chain variable region including the at least one heavy chain complementarity determining region;

at least one light chain complementarity determining region selected from the group consisting of a polypeptide (CDR-L1) including the amino acid sequence of SEQ ID NO: 4, a polypeptide (CDR-L2) including the amino acid sequence of SEQ ID NO: 5, and a polypeptide (CDR-L3) including the amino acid sequence of SEQ ID NO: 6, or a light chain variable region including the at least one light chain complementarity determining region;

a combination of said at least one heavy chain complementarity determining region and said at least one light chain complementarity determining region; or a combination of the heavy chain variable region and the light chain variable region.

More particularly, the anti-Ang2 antibody or an antigen-binding fragment thereof may comprise or consist essentially of:

a heavy chain variable region including a polypeptide (CDR-H1) including the amino acid sequence of SEQ ID NO: 1, a polypeptide (CDR-H2) including the amino acid sequence of SEQ ID NO: 2, and a polypeptide (CDR-H3) including the amino acid sequence of SEQ ID NO: 3;

a light chain variable region including a polypeptide (CDR-L1) including the amino acid sequence of SEQ ID NO: 4, a polypeptide (CDR-L2) including the amino acid sequence of SEQ ID NO: 5, and a polypeptide (CDR-L3) including the amino acid sequence of SEQ ID NO: 6;

a combination of the heavy chain variable region and the light chain variable region.

In one embodiment, the heavy chain variable region of the antibody or the antigen-binding fragment thereof may include the amino acid sequence of SEQ ID NO: 7 or 84:

```
                                              (SEQ ID NO: 7)
DVQLQESGPDLVKPSQSLSLTCTVTGYSITSDYAWNWIRQFPGNKLEWMG

YINYSGNTDYNPSLKSRSSITRDTSKNQFFLQLNSVTTGDTATYYCARGN

FEGAMDYWGQGTSVTVSS;

(SEQ ID NO: 84)
DVQLQESGPGLVKPSQSLSLTCTVTGYSITSDYAWNWIRQFPGNKLEWMG

YINYSGNTDYNPSLKSRSSITRDTSKNQFFLQLNSVTTGDTATYYCARGN

FEGAMDYWGQGTLVTVSS
```

(In SEQ ID NO: 7 or 84 above, the underlined bold letters are CDRH1, CDRH2, and CDRH3 in sequence)

The light chain of the antibody according to one embodiment may include the amino acid sequence of SEQ ID NO: 9:

```
                                              (SEQ ID NO: 9)
SIVMTQTPKFLLVSAGDRVTITCKASQSVSNDVAWYQQKPGQSPKLLIYY

ASNRYPGVPDRFTGSGYGTDFTFTISTVQAEDLAVYFCQQDYSSPWTFGG

GTKLEIK
```

(In SEQ ID NO: 9 above, the underlined bold letters are CDRL1, CDRL2, and CDRL3 in sequence)

The anti-Ang2 antibody or an antigen-binding fragment thereof may include a heavy chain variable region including the amino acid sequence of SEQ ID NO: 7 or 84, a light chain variable region including the amino acid sequence of SEQ ID NO: 9, or a combination of the heavy chain variable region and the light chain variable region.

For example, the anti-Ang2 antibody or an antigen-binding fragment thereof may include a heavy chain variable region including the amino acid sequence of SEQ ID NO: 7 or 84 and a light chain variable region including the amino acid sequence of SEQ ID NO: 9.

The anti-Ang2 antibody or an antigen-binding fragment thereof may be affinity-matured by substituting at least one amino acid residue of at least one CDR, for example, at least one selected from the group consisting of CDR-H2, CDR-L1, CDR-L2 and CDR-L3, with other amino acids (i.e., with an amino acid that is different from the original one, while maintaining the inherent activity of the anti-Ang2 antibody).

For example, the affinity maturation of an anti-Ang2 antibody or an antigen-binding fragment may include at least one of the following substitutions:

(1) a substitution of the $1^{st}$ amino acid residue Tyr (Y) of the amino acid sequence of SEQ ID NO: 2 (YINYSGNTDYNPSLKS) of CDR-H2, with Lys (K);

(2) a substitution of the $3^{rd}$ amino acid residue Asn (N) of the amino acid sequence of SEQ ID NO: 2 (YINYSGNTDYNPSLKS) of CDR-H2, with Ser (S);

(3) a substitution of the $5^{th}$ amino acid residue Ser (S) of the amino acid sequence of SEQ ID NO: 2 (YINYSGNTDYNPSLKS) of CDR-H2, with Ala (A);

(4) a substitution of the $7^{th}$ amino acid residue Asn (N) of the amino acid sequence of SEQ ID NO: 2 (YINYSGNTDYNPSLKS) of CDR-H2, with Lys (K);

(5) a substitution of the $11^{th}$ amino acid residue Ala (A) of the amino acid sequence of SEQ ID NO: 4 (KASQSVSNDVA) of CDR-L1, with His (H);

(6) a substitution of the $5^{th}$ amino acid residue Ser (S) of the amino acid sequence of SEQ ID NO: 4 (KASQSVSNDVA) of CDR-L1, with Phe (F);

(7) a substitution of the $8^{th}$ amino acid residue Asn (N) of the amino acid sequence of SEQ ID NO: 4 (KASQSVSNDVA) of CDR-L1, with Thr (T);

(8) a substitution of the $4^{th}$ amino acid residue Asn (N) of the amino acid sequence of SEQ ID NO: 5 (YASNRYP) of CDR-L2, with Ile (I);

(9) a substitution of the $5^{th}$ amino acid residue Arg (R) of the amino acid sequence of SEQ ID NO: 5 (YASNRYP) of CDR-L2, with Pro (P);

(10) a substitution of the $2^{nd}$ amino acid residue Gln (Q) of the amino acid sequence of SEQ ID NO: 6 (QQDYSSPWT) of CDR-L3, with His (H); and

(11) a substitution of the $8^{th}$ amino acid residue Trp (W) of the amino acid sequence of SEQ ID NO: 6 (QQDYSSPWT) of CDR-L3, with Phe (F), or any combination thereof.

In an embodiment, the affinity-matured anti-Ang2 antibody or an antigen-binding fragment thereof may comprise or consist essentially of a polypeptide comprising an amino acid sequence of represented by following general formula 1 (SEQ ID NO: 20) as a CDR-H2:

```
            (General Formula 1)
                                (SEQ ID NO: 20)
        X1-I-X2-Y-X3-G-X4-T-D-Y-N-P-S-L-K-S
``` wherein, X1 is Tyr (Y) or Lys (K), X2 is Asn (N) or Ser (S), X3 is Ser (S) or Ala (A), and X4 is Asn (N) or Lys (K).

For example, the amino acid sequence of SEQ ID NO: 20 may be provided by the amino acid sequence of SEQ ID NO: 14 or SEQ ID NO: 15.

In another embodiment, the affinity-matured anti-Ang2 antibody or an antigen-binding fragment thereof may comprise or consist essentially of a polypeptide comprising an amino acid sequence of represented by following general formula 2 (SEQ ID NO: 21) as a CDR-L1:

```
            (General Formula 2)
                                (SEQ ID NO: 21)
              K-A-S-Q-X5-V-S-X6-D-V-X7
``` wherein, X5 is Ser (S) or Phe (F), X6 is Asn (N) or Thr (T), and X7 is Ala (A) or His (H).

For example, the amino acid sequence of SEQ ID NO: 21 may be provided by the amino acid sequence of SEQ ID NO: 16 or SEQ ID NO: 17.

In another embodiment, the affinity-matured anti-Ang2 antibody or an antigen-binding fragment thereof may comprise or consist essentially of a polypeptide comprising an amino acid sequence of represented by following general formula 3 (SEQ ID NO: 22) as a CDR-L2:

(General Formula 3)
(SEQ ID NO: 22)
Y-A-S-X8-X9-Y-P wherein, X8 is Asn (N) or Ile (I) and X9 is Arg (R) or Pro (P).

For example, the amino acid sequence of SEQ ID NO: 22 may be provide by the amino acid sequence of SEQ ID NO: 18.

In another embodiment, the affinity-matured anti-Ang2 antibody or an antigen-binding fragment thereof may comprise or consist essentially of a polypeptide comprising an amino acid sequence of represented by following general formula 4 (SEQ ID NO: 23) as a CDR-L3:

(General Formula 4)
(SEQ ID NO: 23)
Q-X10-D-Y-S-S-P-X11-T wherein, X10 is Gln (Q) or His (H) and X11 is Trp (W) or Phe (F).

For example, the amino acid sequence of SEQ ID NO: 23 may be provided by the amino acid sequence of SEQ ID NO: 19.

In an embodiment, the affinity-matured anti-Ang2 antibody or an antigen-binding fragment thereof may comprise or consist essentially of:

a heavy chain variable region including a polypeptide (CDR-H1) including the amino acid sequence of SEQ ID NO: 1, a polypeptide (CDR-H2) including the amino acid sequence of SEQ ID NO: 20, and a polypeptide (CDR-H3) including the amino acid sequence of SEQ ID NO: 3;

a light chain variable region including a polypeptide (CDR-L1) including the amino acid sequence of SEQ ID NO: 21, a polypeptide (CDR-L2) including the amino acid sequence of SEQ ID NO: 22, and a polypeptide (CDR-L3) including the amino acid sequence of SEQ ID NO: 23;

or a combination of the heavy chain variable region and the light chain variable region.

For example, the affinity-matured anti-Ang2 antibody or an antigen-binding fragment thereof may comprise or consist essentially of:

a heavy chain variable region including a polypeptide (CDR-H1) including the amino acid sequence of SEQ ID NO: 1, a polypeptide (CDR-H2) including an amino acid sequence selected from the group consisting of SEQ ID NOs: 2, 14, and 15, and a polypeptide (CDR-H3) including the amino acid sequence of SEQ ID NO: 3;

a light chain variable region including a polypeptide (CDR-L1) including an amino acid sequence selected from the group consisting of SEQ ID NOs: 4, 16, and 17, a polypeptide (CDR-L2) including the amino acid sequence of SEQ ID NO: 5 or 18, and a polypeptide (CDR-L3) including the amino acid sequence of SEQ ID NO: 6 or 19;

or a combination of the heavy chain variable region and the light chain variable region.

In one embodiment, the affinity matured and/or humanized anti-Ang2 antibody or an antigen-binding fragment thereof of the present description does not include all of a polypeptide (CDR-H1) comprising the amino acid sequence of SEQ ID NO: 1, a polypeptide (CDR-H2) comprising the amino acid sequence of SEQ ID NO: 2, a polypeptide (CDR-H3 comprising the amino acid sequence of SEQ ID NO: 3, a polypeptide (CDR-L1) comprising the amino acid sequence of SEQ ID NO: 4, a polypeptide (CDR-L2) comprising the amino acid sequence of SEQ ID NO: 5, and a polypeptide (CDR-L3) comprising the amino acid sequence of SEQ ID NO: 6 together.

The complementarity determining regions of the anti-Ang2 antibody that may serve as a parent antibody or an antigen-binding fragment thereof and the affinity-matured anti-Ang2 antibody or an antigen-binding fragment thereof are summarized in Table 1, as follows:

TABLE 1

|  | CDRH1-KABAT | CDRH2-KABAT | CDRH3-KABAT |
|---|---|---|---|
| Amino acid sequence of heavy chain CDR | | | |
| Parent antibody | SDYAWN (SEQ ID NO: 1) | YINYSGNTDYNPSLKS (SEQ ID NO: 2) | GNFEGAMDY (SEQ ID NO: 3) |
| Affinity-matured antibody | | KISYSG<u>K</u>TDYNPSLKS (SEQ ID NO: 14) KINY<u>A</u>GNTDYNPSLKS (SEQ ID NO: 15) | |
| Amino acid sequence of light chain CDR | | | |
| Parent antibody | KASQSVSNDVA (SEQ ID NO: 4) | YASNRYP (SEQ ID NO: 5) | QQDYSSPWT (SEQ ID NO: 6) |
| Affinity-matured antibody | KASQSVSNDV<u>H</u> (SEQ ID NO: 16) KAS<u>Q</u>FVS<u>T</u>DV<u>H</u> (SEQ ID NO: 17) | YAS<u>IP</u>YP (SEQ ID NO: 18) | <u>QH</u>DYSSP<u>F</u>T (SEQ ID NO: 19) |

For example, the affinity-matured anti-Ang2 antibody or an antigen-binding fragment thereof may be selected from the group consisting of:

(a) an anti-Ang2 antibody or an antigen-binding fragment thereof comprising a heavy chain variable region comprising a CDR-H1 of SEQ ID NO: 1, a CDR-H2 of SEQ ID NO: 14, and a CDR-H3 of SEQ ID NO: 3; and a light chain variable region comprising CDR-L1 of SEQ ID NO: 4, CDR-L2 of SEQ ID NO: 5, and CDR-L3 of SEQ ID NO: 6;

(b) an anti-Ang2 antibody or an antigen-binding fragment thereof comprising a heavy chain variable region comprising a CDR-H1 of SEQ ID NO: 1, a CDR-H2 of SEQ ID NO: 14, and a CDR-H3 of SEQ ID NO: 3; and a light chain variable region comprising CDR-L1 of SEQ ID NO: 16, CDR-L2 of SEQ ID NO: 5, and CDR-L3 of SEQ ID NO: 6;

(c) an anti-Ang2 antibody or an antigen-binding fragment thereof comprising a heavy chain variable region comprising a CDR-H1 of SEQ ID NO: 1, a CDR-H2 of SEQ ID NO: 15, and a CDR-H3 of SEQ ID NO: 3; and a light chain variable region comprising CDR-L1 of SEQ ID NO: 4, CDR-L2 of SEQ ID NO: 5, and CDR-L3 of SEQ ID NO: 6;

(d) an anti-Ang2 antibody or an antigen-binding fragment thereof comprising a heavy chain variable region comprising a CDR-H1 of SEQ ID NO: 1, a CDR-H2 of SEQ ID NO: 15, and a CDR-H3 of SEQ ID NO: 3; and a light chain variable region comprising CDR-L1 of SEQ ID NO: 16, CDR-L2 of SEQ ID NO: 5, and CDR-L3 of SEQ ID NO: 6;

(e) an anti-Ang2 antibody or an antigen-binding fragment thereof comprising a heavy chain variable region comprising a CDR-H1 of SEQ ID NO: 1, a CDR-H2 of SEQ ID NO: 2, and a CDR-H3 of SEQ ID NO: 3; and a light chain variable region comprising CDR-L1 of SEQ ID NO: 16, CDR-L2 of SEQ ID NO: 5, and CDR-L3 of SEQ ID NO: 19;

(f) an anti-Ang2 antibody or an antigen-binding fragment thereof comprising a heavy chain variable region comprising a CDR-H1 of SEQ ID NO: 1, a CDR-H2 of SEQ ID NO: 14, and a CDR-H3 of SEQ ID NO: 3; and a light chain variable region comprising CDR-L1 of SEQ ID NO: 17, CDR-L2 of SEQ ID NO: 5, and CDR-L3 of SEQ ID NO: 6;

(g) an anti-Ang2 antibody or an antigen-binding fragment thereof comprising a heavy chain variable region comprising a CDR-H1 of SEQ ID NO: 1, a CDR-H2 of SEQ ID NO: 14, and a CDR-H3 of SEQ ID NO: 3; and a light chain variable region comprising CDR-L1 of SEQ ID NO: 4, CDR-L2 of SEQ ID NO: 18, and CDR-L3 of SEQ ID NO: 6;

(h) an anti-Ang2 antibody or an antigen-binding fragment thereof comprising a heavy chain complementarity determining region comprising a CDR-H1 of SEQ ID NO: 1, a CDR-H2 of SEQ ID NO: 14, and a CDR-H3 of SEQ ID NO: 3, or a heavy chain variable region comprising the heavy chain complementarity determining region; and a light chain complementarity determining region comprising CDR-L1 of SEQ ID NO: 16, CDR-L2 of SEQ ID NO: 18, and CDR-L3 of SEQ ID NO: 6, or a light chain variable region comprising the light chain complementarity determining region; and (i) an anti-Ang2 antibody or an antigen-binding fragment thereof comprising a heavy chain variable region comprising a CDR-H1 of SEQ ID NO: 1, a CDR-H2 of SEQ ID NO: 14, and a CDR-H3 of SEQ ID NO: 3; and a light chain variable region comprising CDR-L1 of SEQ ID NO: 17, CDR-L2 of SEQ ID NO: 18, and CDR-L3 of SEQ ID NO: 6n.

The affinity-matured anti-Ang2 antibody or an antigen-binding fragment may have an binding affinity (KD) to Ang2 of about 10 nM or less, about 5 nM or less, about 2 nM or less, or about 1 nM or less, for example, about 0.01 to about 10 nM, about 0.01 to about 5 nM, about 0.01 to about 2 nM, or about 0.01 to about 1 nM. The affinity-matured anti-Ang2 antibody or an antigen-binding fragment shows a considerable improvement in the binding affinity (KD) to Ang2, because the binding affinity (KD) to Ang2 of its parent antibody anti-Ang2 antibody is about 8 nM.

In another embodiment, a humanized anti-Ang2 antibody or an antigen-binding fragment thereof is provided. The humanized anti-Ang2 antibody or an antigen-binding fragment thereof may be obtained by substituting at least one amino acid residue of framework region (i.e., the region other than the heavy chain complementarity determining region) of a heavy chain variable region (e.g., SEQ ID NO: 7 or 84). The amino acid sequences of the framework region of a heavy chain variable region, which can be used in producing a humanized anti-Ang2 antibody or an antigen-binding fragment thereof, are summarized in Table 2:

TABLE 2

(Humanization of a heavy chain)

| | FR1 (framework region of N-terminus of CDR-H1) | FR2 (framework region between CDR-H1 and CDR-H2) | FR3 (framework region between CDR-H2 and CDR-H3) | FR4 (framework region of C-terminus of CDR-H3) |
|---|---|---|---|---|
| Parent antibody (SEQ ID NO: 7 or 84) | DVQLQESGPDLVK PSQSLSLTCTVTG YSIT (SEQ ID NO: 24) or DVQLQESGPGLVK PSQSLSLTCTVTG YSIT (SEQ ID NO: 85) | WIRQFPGNKLEW MG (SEQ ID NO: 29) | RSSITRDTSKNQFF LQLNSVTTGDTAT YYCAR (SEQ ID NO: 34) | WGQGTSVTVSS (SEQ ID NO: 39) or WGQGTLVTVSS (SEQ ID NO: 86) |
| Humanized antibody (VH-hu1) | QVQLQESGPGLVK PSETLSLTCAVSG YSIS (SEQ ID NO: 25) | WIRQPPGKGLEWI G (SEQ ID NO: 30) | RVTISVDTSKNQF SLKLSSVTAADTA VYYCAR (SEQ ID NO: 35) | WGQGTLVTVSS (SEQ ID NO: 40) |
| Humanized antibody (VH-hu2) | QVQLQESGPGLVK PSETLSLTCAVSG YSIT (SEQ ID NO: 26) | WIRQPPGKGLEW MG (SEQ ID NO: 31) | RSTISRDTSKNQFS LKLSSVTAADTAV YYCAR (SEQ ID NO: 36) | WGQGTLVTVSS (SEQ ID NO: 41) |
| Humanized antibody (VH-hu5) | QVQLQESGPGLVK PSETLSLTCAVSG YSIT (SEQ ID NO: 27) | WIRQPPGKGLEWI G (SEQ ID NO: 32) | RVTISVDTSKNQF SLKLSSVTAADTA VYYCAR (SEQ ID NO: 37) | WGQGTLVTVSS (SEQ ID NO: 42) |

TABLE 2-continued (Humanization of a heavy chain)

| | FR1 (framework region of N-terminus of CDR-H1) | FR2 (framework region between CDR-H1 and CDR-H2) | FR3 (framework region between CDR-H2 and CDR-H3) | FR4 (framework region of C-terminus of CDR-H3) |
|---|---|---|---|---|
| Humanized antibody (VH-hu3) | EVQLVESGGGLV QPGGSLRLSCAAS GYSIT(SEQ ID NO: 28) | WVRQAPGKGLEW MG(SEQ ID NO: 33) | RSTISRDTSKNTFY LQMNSLRAEDTA VYYCAR(SEQ ID NO: 38) | WGQGTLVTVSS(SEQ ID NO: 43) |

In addition, the humanized anti-Ang2 antibody or an antigen-binding fragment thereof may be obtained by substituting at least one amino acid residue of framework region (i.e., the region other than the heavy chain complementarity determining region) of a light chain variable region (e.g., SEQ ID NO: 9). The amino acid sequences of the framework region of a light chain variable region, which can be used in producing a humanized anti-Ang2 antibody or an antigen-binding fragment thereof, are summarized in Table 3:

TABLE 3

(Humanization of a light chain)

| | FR1 (framework region adjacent to N-terminus of CDR-L1) | FR2 (framework region between CDR-L1 and CDR-L2) | FR3 (framework region between CDR-L2 and CDR-L3) | FR4 (framework region adjacent to C-terminus of CDR-L3) |
|---|---|---|---|---|
| Parent antibody(SEQ ID NO: 9) | SIVMTQTPKFLLVS AGDRVTITC(SEQ ID NO: 44) | WYQQKPGQSPKLL IY(SEQ ID NO: 46) | GVPDRFTGSGYGT DFTFTISTVQAEDL AVYFC(SEQ ID NO: 48) | FGGGTKLEIK(SEQ ID NO: 50) |
| Humanized antibody (VL-hu1) | DIQMTQSPSSLSAS VGDRVTITC(SEQ ID NO: 45) | WYQQKPGKAPKLL IY(SEQ ID NO: 47) | GVPSRFSGSGSGTD FTLTISSLQPEDFAT YYC(SEQ ID NO: 49) | FGQGTKVEIK(SEQ ID NO: 51) |

In an embodiment, a heavy chain variable region of the humanized anti-Ang2 antibody or an antigen-binding fragment thereof may comprise or consist essentially of:

a polypeptide comprising an amino acid sequence selected from the group consisting of SEQ ID NOs: 24 to 28, for example, an amino acid sequence selected from the group consisting of SEQ ID NOs: 25 to 28, as a framework region adjacent to N-terminus of CDR-H1, a polypeptide comprising an amino acid sequence selected from the group consisting of SEQ ID NOs: 29 to 33, for example, an amino acid sequence selected from the group consisting of SEQ ID NOs: 30 to 33, as a framework region between CDR-H1 and CDR-H2, a polypeptide comprising an amino acid sequence selected from the group consisting of SEQ ID NOs: 34 to 38, for example, an amino acid sequence selected from the group consisting of SEQ ID NOs: 35 to 38, as a framework region between CDR-H2 and CDR-H3, and a polypeptide comprising an amino acid sequence selected from the group consisting of SEQ ID NOs: 39 to 43, for example, an amino acid sequence selected from the group consisting of SEQ ID NOs: 40 to 43, as a framework region adjacent to C-terminus of CDR-H3.

A light chain variable region of the humanized anti-Ang2 antibody or an antigen-binding fragment thereof may comprise or consist essentially of:

a polypeptide comprising an amino acid sequence selected from the group consisting of SEQ ID NO: 44 or 45, for example, SEQ ID NO: 45, as a framework region adjacent to N-terminus of CDR-L1, a polypeptide comprising an amino acid sequence selected from the group consisting of SEQ ID NO: 46 or 47, for example, SEQ ID NO: 47, as a framework region between CDR-L1 and CDR-L2, a polypeptide comprising an amino acid sequence selected from the group consisting of SEQ ID NO: 48 or 49, for example, SEQ ID NO: 49, as a framework region between CDR-L2 and CDR-L3, and a polypeptide comprising an amino acid sequence selected from the group consisting of SEQ ID NO: 50 or 51, for example, SEQ ID NO: 51, as a framework region adjacent to C-terminus of CDR-L3.

In certain embodiments, one or more of the heavy chain variable region comprising the amino acid sequence of SEQ ID NO: 24 as a framework region adjacent to N-terminus of CDR-H1, the amino acid sequence of SEQ ID NO: 29 as a framework region between CDR-H1 and CDR-H2, the amino acid sequence of SEQ ID NO: 34 as a framework region between CDR-H2 and CDR-H3, and the amino acid sequence of SEQ ID NO: 39 as a framework region adjacent to C-terminus of CDR-H3; and the light chain variable region comprising the amino acid sequence of SEQ ID NO: 44 as a framework region adjacent to N-terminus of CDR-L1, the amino acid sequence of SEQ ID NO: 46 as a framework region between CDR-L1 and CDR-L2, the amino acid sequence of SEQ ID NO: 48 as a framework region between CDR-L2 and CDR-L3, and the amino acid sequence of SEQ ID NO: 50 as a framework region adjacent to C-terminus of CDR-L3, can be excluded from the humanized anti-Ang2 antibody or an antigen-binding fragment thereof according to the present description.

In an embodiment, the humanized anti-Ang2 antibody or an antigen-binding fragment thereof may comprises a heavy chain variable region comprising an amino acid sequence selected from the group consisting of SEQ ID NOs: 52 to 56, a light chain variable region comprising an amino acid sequence selected from the group consisting of SEQ ID NOs: 57 to 63, or any combination thereof.

The antibody includes any animal-derived antibodies, chimeric antibodies, humanized antibodies and human antibodies. An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

An important consideration in CDR grafting technology for manufacturing a humanized antibody is to select an optimized human antibody which can receive best the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be essential to apply an additional antibody engineering technology for restoring antigen binding affinity.

According to one embodiment, the antibody may be an animal antibody such as a mouse-derived antibody, a chimeric antibody such as a mouse-human chimeric antibody, a humanized antibody, or a human antibody. The antibody or an antigen-binding fragment thereof may be isolated from a living body or non-naturally occurring. The antibody or an antigen-binding fragment thereof may be recombinant or synthetic. The antibody or an antigen-binding fragment thereof may be monoclonal.

Antibodies have been widely used for treating diseases. As antibodies are very stable in vivo as well as in vitro and have a long half-life, they are favorable for mass expression and production. Additionally, since an antibody has intrinsically a dimer structure, it has a fairly high avidity.

An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma ($\gamma$), mu ($\mu$), alpha ($\alpha$), delta ($\delta$) and epsilon ($\epsilon$) types, and has gamma1 ($\gamma1$), gamma2 ($\gamma2$), gamma3 ($\gamma3$), gamma4 ($\gamma4$), alpha1 ($\alpha1$) and alpha2 ($\alpha2$) as its subclass. The light chain constant region has kappa ($\kappa$) and lambda ($\lambda$) types.

The term "heavy chain" is understood to include a full-length heavy chain and fragments thereof, the full-length heavy chain including a variable region domain $V_H$ including an amino acid sequence having sufficient variable region sequences that contribute the specificity for antigen binding and three constant region domains $C_{H1}$, $C_{H2}$ and $C_{H3}$ domains and a hinge. The term "light chain" is understood to include a full-length light chain and fragments thereof, the full-length light chain including a variable region domain $V_L$ including an amino acid sequence having sufficient variable region sequences that contribute to the specificity for antigen binding and a constant region domain $C_L$.

The term "CDR (complementarity determining region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope. Throughout the specification, the terms "specifically binding" or "specifically recognizing" have the same meaning as generally known to an ordinary person in the art, indicating that an antigen and an antibody specifically interact with each other to lead to an immunological response.

The antigen-binding site of an antibody may be a fragment including at least one complementarity determining region.

The term "antigen-binding fragment," which is a fragment of the full structure of an immunoglobulin, refers to some of a polypeptide including a portion to which an antigen can bind. For example, it may be an scFv, an (scFv)$_2$, an scFv-Fc, an Fab, an Fab' or an F(ab')$_2$, but is not limited thereto.

Among the above antigen-binding fragments, an Fab, which is a structure having the light chain and heavy chain variable regions, the light chain constant region, and the heavy chain first constant region ($C_{H1}$), has one antigen binding site. An Fab' differs from the Fab in that the Fab' has a hinge region including at least one cysteine residue at the C-terminal of the heavy chain $C_{H1}$ domain. An F(ab')$_2$ is produced when cysteine residues at the hinge region of Fab' are joined by a disulfide bond. An Fv is a minimal antibody fragment, having only heavy chain variable regions and light chain variable regions, and a recombinant technique for producing the Fv fragment is well known in the art. In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other via a covalent bond or directly at the C-terminus, so that it can form a dimer as in a two-chain Fv fragment. In this context, the heavy chain variable region and the light chain variable region may be connected with each other through a linker, e. g., a peptide linker, or directly. The peptide linker may be composed of about 1 to about 100 amino acid residues, or about 2 to about 50 amino acid residues. For example, the peptide linker may include Gly, Asn and/or Ser, and may also include neutral amino acids such as Thr and/or Ala. Amino acid sequences suitable for use in the peptide linker may be those well known in the art. So long as it has no negative influence on the function of the antigen-binding fragment, the length of the peptide linker may be appropriately adjusted. For example, the peptide linker may be an amino sequence composed of about 1 to about 100, about 2 to about 50, or about 5 to about 25 amino acid residues selected from among Gly, Asn, Ser, Thr, Ala, and a combination thereof. By way of example, the peptide linker may be (GGGGS)n (wherein n represents the repeating number of (GGGGS) and may be an integer of 1 to 10, e.g., 2 to 5).

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region included in the heavy chains of an antibody, which is present between the CH1 and CH2 regions, and provides flexibility to the antigen binding site in the antibody. For example, the hinge may be derived from a human antibody and particularly, it may be derived from IgA, IgE, IgD, IgM, or IgG, for example, IgG1, IgG2, IgG 3, or IgG4.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects. Therefore, modification of a hinge region can increase an antigen binding efficiency of a humanized antibody. Methods of deleting, inserting, or substituting an amino acid for modifying amino acid sequences of the hinge region are well known in the art.

Portions (e.g., constant regions) except the CDRs or variable regions of the anti-Ang2 antibody may be derived from an immunoglobulin such as IgA, IgD, IgE, IgD, IgM, or IgG, for example, IgG1, IgG2, IgG 3, or IgG4, and for example, they may be from a human the immunoglobulin (antibody).

The anti-Ang2 antibody may be a monoclonal antibody. The monoclonal antibody may be prepared by methods well known in the art. For example, it may be prepared using a phage display technique. Alternately, the Ang2 antibody may be prepared into a mouse-derived monoclonal antibody by methods set forth in the paper written by Schwaber, et al (Schwaber, J and Cohen, E. P., "Human×Mouse Somatic Cell Hybrid Clones Secreting Immunoglobulins of Both Parental Types," Nature, 244 (1973), 444-447).

Individual monoclonal antibodies may be screened using a typical ELISA (Enzyme-Linked ImmunoSorbent Assay) format, based on the binding potential with Ang2. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 may be each verified.

The remaining portions of the anti-Ang2 antibody not including the antigen binding portions of the finally selected antibodies may be prepared as not only human immunoglobulin antibodies but also humanized antibodies. Preparation of humanized antibodies is well known in the art (Almagro, J. C. and Fransson, J., "Humanization of antibodies," Frontiers in Bioscience, 13(2008), 1619-1633).

Another embodiment provides a hybridoma cell line which produces a monoclonal antibody of the anti-Ang2 antibody. The hybridoma cell line may be a cell line having accession number (KCLRF-BP-00295).

A polypeptide comprising an amino acid sequence represented by SEQ ID NO: 20, for example, an amino acid sequence of SEQ ID NO: 14 or SEQ ID NO: 15, may be useful as a CDR-H2 of an affinity-matured anti-Ang2 antibody or antigen-binding fragment thereof. In addition, a polypeptide comprising an amino acid sequence represented by SEQ ID NO: 21, for example, an amino acid sequence of SEQ ID NO: 16 or SEQ ID NO: 17, may be useful as a CDR-L1 of an affinity-matured anti-Ang2 antibody or antigen-binding fragment thereof. In addition, a polypeptide comprising an amino acid sequence represented by SEQ ID NO: 22, for example, an amino acid sequence of SEQ ID NO: 18, may be useful as a CDR-L2 of an affinity-matured anti-Ang2 antibody or antigen-binding fragment thereof. In addition, a polypeptide comprising an amino acid sequence represented by SEQ ID NO: 23, for example, an amino acid sequence of SEQ ID NO: 19, may be useful as a CDR-L3 of an affinity-matured anti-Ang2 antibody or antigen-binding fragment thereof.

Therefore, an embodiment provides a polypeptide comprising an amino acid sequence selected from the group consisting of SEQ ID NO: 20 (e.g., SEQ ID NO: 14 or SEQ ID NO: 15), SEQ ID NO: 21 (e.g., SEQ ID NO: 16 or SEQ ID NO: 17), SEQ ID NO: 22 (e.g., SEQ ID NO: 18), and SEQ ID NO: 23 (e.g., SEQ ID NO: 19). As described above, the polypeptide may be useful as a complementarity determining region of an affinity-matured anti-Ang2 antibody or antigen-binding fragment thereof.

Another embodiment provides a polynucleotide encoding the polypeptide. Another embodiment provides a recombinant vector comprising (or carrying) the polynucleotide. Another embodiment provides a recombinant cell comprising (or transfected with) the recombinant vector.

Another embodiment provides a complex of Ang2 and a humanized and/or affinity-matured anti-Ang2 antibody in which the humanized and/or affinity-matured anti-Ang2 antibody or an antigen-binding fragment thereof and Ang2 are bound to each other.

Another embodiment provides a composition for inducing binding of Ang2 with a Tie2 receptor, including the complex of Ang2 and an anti-Ang2 antibody as an active ingredient. Another embodiment provides a method for inducing binding of Ang2 with a Tie2 receptor, including administering the complex of Ang2 and a humanized and/or affinity-matured anti-Ang2 antibody to a subject. The subject may be in need of binding between Ang2 and Tie2 receptor. The method for inducing binding of Ang2 with Tie2 receptor may further include a step of identifying a subject who is in need of binding between Ang2 and Tie2 receptor, prior to the administration step. Another embodiment provides a composition for activating a Tie2 receptor including the complex of Ang2 and a humanized and/or affinity-matured anti-Ang2 antibody as an active ingredient.

Another embodiment provides a method for activating a Tie2 receptor including administering the complex of Ang2 and a humanized and/or affinity-matured anti-Ang2 antibody to a subject. The subject may be in need of activating the Tie2 receptor. The Tie2 receptor activation method may further include a step of identifying a subject who is in need of activating the Tie2 receptor, prior to the administration step. The subject may be selected from mammals including primates such as humans and monkeys or rodents such as rats and mice, or cells, tissues, or body fluids (e.g., blood, serum, etc.) isolated therefrom or artificially cultured. Another embodiment provides a use of the complex of Ang2 and a humanized and/or affinity-matured anti-Ang2 antibody in inducing binding of Ang2 with a Tie2 receptor and/or activating a Tie2 receptor.

As described above, since the humanized and/or affinity-matured anti-Ang2 antibody or an antigen-binding fragment thereof has a function of inhibiting abnormal angiogenesis by inhibiting the functions of Ang2, it is applicable to prevent, alleviate, improve, and/or treat various diseases (e.g., cancer) related to abnormal angiogenesis. Moreover, since the humanized and/or affinity-matured anti-Ang2 antibody or an antigen-binding fragment thereof does not inhibit binding between Ang2 and Tie2, it can activate a Tie2 signaling by activating Tie2, and it accelerates the formation of vascular endothelium or lymphatic endothelium and increases mobility, to suppress vascular permeability increase, whereby it is applicable to prevent, alleviate, improve, and/or treat various diseases related to vascular permeability (for example, sepsis, eye disorders, etc.). Also, as described above, since the humanized and/or affinity-matured anti-Ang2 antibody or an antigen-binding fragment thereof accelerates the formation of vascular endothelium or lymphatic endothelium to increase the formation of healthy blood vessels and normalize the blood vessels, it is also applicable to prevent, alleviate, improve, and/or treat various diseases or symptoms requiring the formation of healthy blood vessels such as wound healing or ischemic disorders, and it reduces cancer growth and metastasis possibility by changing the abnormally formed cancer blood vessels into structurally and functionally normal forms. Moreover, the anti-Ang2 antibody or an antigen-binding fragment thereof has an effect of suppressing inflammatory response, whereby it is applicable to prevent, alleviate, improve, and/or treat various inflammatory disorders. In addition, the anti-Ang2 antibody or an antigen-binding fragment thereof has the effect of normalization of blood vessels in cancer cells, thereby increasing the transporting efficiency of an anticancer agent through the normalized blood vessels into Ang2 expressing cells. Therefore, when co-administered with an anticancer agent to a subject, the anti-Ang2 antibody or an antigen-binding fragment thereof can be used as an adjuvant for enhancing sensitiveness to the anticancer agent and efficacy of the anticancer agent in the subject.

The anticancer agent may be at least one agent selected from all chemical drugs, antibodies, genes (e.g., antisense oligonucleotide, siRNA, shRNA, microRNA, etc.), aptamer, cells for therapeutic use, agents for radiotherapy, and the like, for the use of growth inhibition, apoptosis promotion and metastasis inhibition of cancer cells or cancer tissues. For example, the anticancer agent may be at least one selected from the group consisting of cisplatin, carboplatin, oxalliplatin, paclitaxel, doxetaxel, vincristine, doxorubicin, daunorubicin, bleomycin, prednisone, methotrexate (MTX), 5-fluorouracil (5-FU), 6-mercaptopurine (6-MP), 6-thioguanine (6-TG), and the like, but not be limited thereto:

1) alkylating agents including i) platinum-based compounds including cisplatin, carboplatin, oxaliplatin (oxlipatin), and the like, ii) nitrogen mustard-based compounds including mechlorethamine (nitrogen mustard), cyclophosphamide, ifosfamide, melphalan, chlorambucil, and the like, iii) ethylenimine- and methylmelamine-based drugs including thiotepa, altretamine, and the like, iv) methylhydrazine derivatives including procarbazine, and the like, v) alkyl sulfonate-based drug including busulfan, and the like, vi) nitrosourea-based drugs including carmustine, lomustine, and the like, and vii) triazine-based drugs including dacarbazine, and the like;

2) antimetabolites including i) pyrimidine derivatives including fluorouracil (5-FU), capecitabine, cytarabine, gemcitabine, and the like, ii) folic acid derivatives including methotrexate (MTX), and the like, and iii) purine derivatives including mercaptopurine (6-MP), and the like;

3) natural materials including i) *vinca* alkaloid including vinblastine, vincristine, vinorelvine, and the like, ii) taxane including paclitaxel, docetaxel, and the like, iii) epipodophyllotoxin including etoposide and the like, and iii) camptothecin including topotecan, irinotecan, and the like;

4) antibiotic materials including dactinomycin, doxorubicin, daunorubicin, mitomycin, bleomycin, and the like;

5) Targeted drugs including i) tyrosine kinase inhibitors including imatinib, trastuzumab, cetuximab, gefitinib, erlotinib, and the like, and ii) angiogenesis inhibitors including bevacizumab, sunitinib, sorafenib, cabozantinib, pazopanib, regorafenib, vandetanib, ziv-afilibercept, and the like; and 6) prednisone, 6-thioguanine (6-TG), and the like.

Another embodiment provides a pharmaceutical composition including the humanized and/or affinity-matured anti-Ang2 antibody or an antigen-binding fragment thereof as an active ingredient and a carrier.

Another embodiment provides a pharmaceutical composition for inhibiting angiogenesis including the humanized and/or affinity-matured anti-Ang2 antibody or an antigen-binding fragment thereof as an active ingredient. Another embodiment provides a method for inhibiting angiogenesis including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of inhibiting angiogenesis. The angiogenesis inhibition method may further include a step of identifying a subject who is in need of the inhibition of angiogenesis (e.g., a subject with overexpression of Ang2), prior to the administration step. The step of identifying a subject may further comprise comparing a level of Ang2 in a biological sample (e.g., cell, tissue, fluid, etc.) from a subject to that of a control (a normal biological sample; e.g., with no overexpression of Ang2) and determining the subject as a suitable candidate for treatment with an anti-Ang2 antibody, when the level of Ang2 in a biological sample from the subject is higher than that of control.

Another embodiment provides a pharmaceutical composition for reducing vascular permeability including the humanized and/or affinity-matured anti-Ang2 antibody or an antigen-binding fragment thereof as an active ingredient. Another embodiment provides a method for reducing vascular permeability including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of the reduction of vascular permeability. The vascular permeability reduction method may further include a step of identifying a subject who is in need of the reduction of vascular permeability, prior to the administration step.

Another embodiment provides a pharmaceutical composition for preventing and/or treating a disease related to Ang2 overexpression, angiogenesis, and/or an increase in vascular permeability including the humanized and/or affinity-matured anti-Ang2 antibody or an antigen-binding fragment thereof as an active ingredient. Another embodiment provides a method for preventing and/or treating a disease related to Ang2 overexpression, angiogenesis, and/or an increase in vascular permeability including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of preventing and/or treating the disease related to Ang2 overexpression, angiogenesis, and/or vascular permeability increase. The prevention and/or treatment method may further include a step of identifying a subject who is in need of preventing and/or treating a disease related to Ang2 overexpression, angiogenesis, and/or vascular permeability increase, prior to the administration step. The subject may be one suffering from a disease related to Ang2 overexpression, angiogenesis, and/or vascular permeability increase.

Another embodiment provides a pharmaceutical composition for inducing normal blood vessel formation including the humanized and/or affinity-matured anti-Ang2 antibody or an antigen-binding fragment thereof as an active ingredient. Another embodiment provides a method of inducing normal blood vessel formation, including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of inducing normal blood vessel formation. The method of inducing normal blood vessel formation may further include a step of identifying a subject who is in need of inducing normal blood vessel formation, prior to the administration step.

Another embodiment provides a pharmaceutical composition for preventing and/or treating a disease related to a decrease in normal blood vessel formation including the humanized and/or affinity-matured anti-Ang2 antibody or an antigen-binding fragment thereof as an active ingredient. Another embodiment provides a method for preventing and/or treating a disease related to a decrease in normal blood vessel formation including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of preventing and/or treating the disease related to a decrease in normal blood vessel formation. The prevention and/or treatment method may further include a step of identifying a subject who is in need of preventing and/or treating a disease related to normal blood vessel formation decrease, prior to the administration step. The subject may be one suffering from a disease related to normal blood vessel formation decrease.

Another embodiment provides a pharmaceutical composition for tissue regeneration and/or wound healing including the humanized and/or affinity-matured anti-Ang2 antibody or an antigen-binding fragment thereof as an active ingredient. Another embodiment provides a method for tissue regeneration and/or wound healing including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of tissue regeneration and/or wound healing. The method may further include a step of identifying a subject who is in need of tissue regeneration and/or wound healing, prior to the administration step. A subject to whom the active ingredient is administered may be a subject who has a skin tissue or organ tissue damage or has received a skin transplant.

Another embodiment provides a pharmaceutical composition for inhibiting Ang2 and/or activating a Tie2 receptor including the humanized and/or affinity-matured anti-Ang2 antibody or an antigen-binding fragment thereof as an active ingredient. Another embodiment provides a method for inhibiting Ang2 and/or activating a Tie2 receptor including administering the humanized and/or affinity-matured anti-Ang2 antibody or an antigen-binding fragment thereof to a subject. The humanized and/or affinity-matured anti-Ang2 antibody or an antigen-binding fragment thereof may be administered in amount that is pharmaceutically effective, which amount may be determined by the skilled medical practitioner or medical researcher. The subject may be in need of Ang2 inhibition and/or Tie2 receptor activation. The Ang2 inhibition and/or Tie2 receptor activation method may further include a step of identifying a subject who is in need of Ang2 inhibition and/or Tie2 receptor activation, prior to the administration step. The anti-Ang2 antibody or an antigen-binding fragment thereof may be in a form of being bound to an antigen Ang2.

Another embodiment provides a pharmaceutical composition (an adjuvant) for enhancing the efficacy of an anticancer agent including the humanized and/or affinity-matured anti-Ang2 antibody or an antigen-binding fragment thereof. Another embodiment provides a method of enhancing the efficacy of an anticancer agent. The method includes administering the humanized and/or affinity-matured anti-Ang2 antibody or an antigen-binding fragment thereof to a subject in need of administration of the anticancer agent. The humanized and/or affinity-matured anti-Ang2 antibody or an antigen-binding fragment thereof may be administered in amount that is pharmaceutically effective, which amount may be determined by the skilled medical practitioner or medical researcher. The method may further include, prior to the administration step, a step of identifying a subject in need of administration of the anticancer agent. The enhancement of an anticancer agent may refer to making the anticancer agent exhibit more excellent anticancer effect at relatively low dosage, which is due to vascular normalization thereby increasing transporting efficiency of the anticancer agent into cancer tissues and increasing sensitiveness to the anticancer agent. The adjuvant may refer to a supplementary pharmaceutical composition used for enhancing the efficacy of an anticancer agent.

Since the function of the humanized and/or affinity-matured anti-Ang2 antibody or an antigen-binding fragment thereof, which is an active ingredient of the above pharmaceutical compositions, is activated by the binding with Ang2, the pharmaceutical compositions may further include Ang2 to enhance the function of the antibody or the antigen-binding fragment thereof. The above methods may further include a step of administering Ang2 to a subject. The Ang2 may be administered in amount that is pharmaceutically effective, which amount may be determined by the skilled medical practitioner or medical researcher. The Ang2 may be administered together with the anti-Ang2 antibody or an antigen-binding fragment thereof simultaneously or sequentially in any order.

The pharmaceutical compositions described herein may further include a pharmaceutically acceptable carrier, and the carrier may be those commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical compositions may further include one or more selected from the group consisting of a diluent, an excipient, a lubricant, a wetting agent, a sweetener, a flavor enhancer, an emulsifying agent, a suspension agent, and a preservative.

Pharmaceutically effective amounts of the pharmaceutical compositions, or the antibody or the antigen-binding fragment thereof may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The content of the anti-Ang2 antibody or an antigen-binding fragment thereof in the pharmaceutical compositions may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the anti-Ang2 antibody or an antigen-binding fragment thereof may be within the range of 0.001 to 1000 mg/kg, particularly 0.01 to 100 mg/kg, and more particularly 0.1 to 50 mg/kg, but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical compositions may be formulated into a form of a solution in oil or an aqueous medium, a suspension, syrup, an emulsifying solution, an extract, powder, granules, a tablet, or a capsule, and may further include a dispersing or a stabilizing agent for the formulation.

In particular, the pharmaceutical compositions including the anti-Ang2 antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the humanized and/or affinity-matured anti-Ang2 antibody or an antigen-binding fragment thereof specifically binds to Ang2, this can be used to detect Ang2, and the presence of the overexpression of Ang2 can be verified through it. Accordingly, another embodiment provides a composition for detecting Ang2 and a composition for diagnosing a disease related to Ang2 overexpression, angiogenesis, an increase in vascular permeability, and/or a decrease in normal blood vessel formation, including the humanized and/or affinity-matured anti-Ang2 antibody or an antigen-binding fragment thereof.

In another embodiment, provided is a method for detecting Ang2 including treating (or contacting) a biological specimen obtained (or isolated) from a subject with the humanized and/or affinity-matured anti-Ang2 antibody or an antigen-binding fragment thereof; and identifying the presence of an antigen-antibody reaction between Ang2 and the anti-Ang2 antibody or fragment thereof. Also, there is provided a method of diagnosing a disease related to Ang2 overexpression, angiogenesis, an increase in vascular permeability, and/or a decrease in normal blood vessel formation, including treating (or contacting) a biological specimen obtained from a subject with the humanized and/or affinity-matured anti-Ang2 antibody or an antigen-binding fragment thereof; and identifying the presence of an antigen-antibody reaction between Ang2 and the anti-Ang2 antibody or fragment thereof, wherein a subject is determined to have the disease related to Ang2 overexpression, angiogenesis, and/or an increase in vascular permeability, when the antigen-antibody reaction is present, or is increased compared to the antigen antibody reaction of a control sample that represents known "normal" levels of antigen-antibody reaction (e.g., the control sample may be an animal such as human, or cells or tissues obtained therefrom, who has no disease related to Ang2 overexpression, angiogenesis, and/or an increase in vascular permeability).

In the method of the diagnosing, a subject may be determined to have Ang2 overexpression symptoms, or have the diseases when an antigen-antibody reaction is detected in the step of identifying the presence of an antigen-antibody reaction. Therefore, method may further comprise determining a subject to have Ang2 overexpression symptoms, or have Ang2 overexpression related diseases when an antigen-antibody reaction is detected in the step of identifying, after the step of identifying the presence of an antigen-antibody reaction, and wherein a subject is determined to have the disease related to Ang2 overexpression, when the antigen-antibody reaction is present, or is increased compared to the antigen antibody reaction of a control sample that represents known "normal" levels of antigen-antibody reaction (e.g., the control sample may be an animal such as human, or cells or tissues obtained therefrom, who has no disease related to Ang2 overexpression).

The biological specimen may be selected from the group consisting of cells, tissues and body fluids obtained (isolated) from a subject.

The step of identifying the presence of the antigen-antibody reaction may be performed using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The subjects which the pharmaceutical composition or the antibody or the antigen-binding fragment thereof is administered to or is aimed to diagnose may be mammals including primates such as humans and monkeys, or rodents such as rats and mice, or cells, tissues and body fluids isolated therefrom or artificially cultured.

The diseases related to angiogenesis and/or an increase in vascular permeability and/or Ang2 overexpression may be cancer; cancer metastasis; ocular blood vessel disorders such as retinopathy of prematurity, macular degeneration (e.g., age-related macular degeneration), diabetic retinopathy, neovascular glaucoma, etc.; inflammatory disorders such as psoriasis, asthma, rheumatoid arthritis, pneumonia, chronic inflammation, etc.; infectious disorders (infection); cardiovascular disorders such as hypertension, arteriosclerosis, etc.; renal disease; sepsis; asthma; edema; hereditary hemorrhagic telangiectasia (HHT), etc. The cancer may be those overexpressing Ang2, it may be a solid cancer or a blood cancer, and it may be, but not limited to, selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, etc. The cancer may be a primary cancer or a metastatic cancer.

The diseases related to a decrease in normal blood vessel formation are diseases that require the induction of normal blood vessel formation and may be selected from the group consisting of ischemic disorders such as myocardial infarction, angina, cerebral infarction, stroke (ischemic stroke), etc., Buerger' disease (thromboangiitis obliterans), avascular necrosis, foot ulcer (e.g., diabetic foot ulcer), erectile dysfunction and so on.

Another embodiment provides a complex in which the humanized and/or affinity-matured anti-Ang2 antibody or an antigen-binding fragment thereof, Ang2, and Tie2 receptor are bound (i.e., the anti-Ang2 antibody or an antigen-binding fragment thereof binds to Ang2, Ang2 binds to Tie2 receptor, and the anti-Ang2 antibody or an antigen-binding fragment thereof and Tie2 receptor are bound via Ang2). The complex may be present inside the body or present in a cell isolated from the body. Also, the antibody in the complex may form a dimer with another antibody in an adjacent complex, thereby clustering two or more complexes, to form a cluster including two or more complexes. Such action is related to the Tie2 receptor activation function of the anti-Ang2 antibody. The complex can be used to monitor the action of the anti-Ang2 antibody, i.e., the presence of Ang2 inhibition and/or Tie2 receptor activation, or simply used to inhibit Ang2 and/or to activate Tie2 receptor.

Previously, there were attempts to inhibit angiogenesis by Ang2 by inhibiting binding between Ang2 and its receptor Tie2, but an antibody which specifically binds to Ang2 to induce the intracellular internalization and degradation of Ang2 and at the same time, maintains a binding ability with Ang2 and Tie2 receptor to form an antibody-Ang2-Tie2 receptor complex, thereby activating the Tie2 receptor was not known. Thus, the invention proposes a humanization and/or affinity maturation of an antibody capable of inhibiting angiogenesis by Ang2 and reducing vascular permeability by providing an antibody which inhibits Ang2 and at the same time activates the Tie2 receptor to accelerate its downstream signaling. Also, the humanized and/or affinity-matured antibody proposed in the invention is anticipated to be applicable to diagnose and treat abnormal blood vessel formation-related disorders other than cancer and/or disorders caused by vascular permeability increase. The humanized and/or affinity-matured antibody can be utilized for combination therapy with chemical medicines and other anticancer drugs, and is expected to be employed for antibody fragments, bi- or multi-specific antibodies, protein scaffolds, etc. using Ang2 specific recognition activity.

EXAMPLES

Hereafter, the present invention will be described in detail by examples.

The following examples are intended merely to illustrate the invention and are not construed to restrict the invention.

Example 1. Preparation of a Mouse Anti-Ang2 Antibody, 10D6

1.1. Immunization of a Mouse

A human Ang2 protein (R&D systems; 623-AN-025/CF) was administered to 5-week-old BALB/c mice along with an adjuvant to induce an immune response and then, hybridomas that produce an individual anti-Ang2 antibody were prepared according to the known methods described in the paper written by Schwaber, et al (Schwaber, J and Cohen, E. P., "Human×Mouse Somatic Cell Hybrid Clones Secreting Immunoglobulins of Both Parental Types," Nature, 244 (1973), 444-447).

More specifically, to obtain immunized mice necessary for developing hybridoma cell lines, 100 μg (microgram) of human Ang2 protein (R&D Systems) mixed with the same amount of a complete Freund's adjuvant was administered via an intraperitoneal injection to each of five 4~6-week-old BALB/c mice (Japan SLC, Inc.). After two weeks, the antigen (half the previously injected amount) mixed with an incomplete Freund's adjuvant using the same method as described above was administered to each mouse via an intraperitoneal injection. After one additional week, a final boosting was performed and three days later, blood was collected from the tail of each mouse to obtain serum, which was then diluted at 1/1000 with PBS and subjected to an ELISA to verify that the titer of an antibody recognizing Ang2 was increased. From the results, mice in which a sufficient amount of the antibody was obtained were selected, and a cell fusion process was performed on the selected mice.

Three days before the cell fusion experiment, a mixture of 50 μg of PBS and 100 μg of human Ang2 protein (R&D systems) was administered via an intraperitoneal injection to BALB/c mice (Japan SLC, Inc.), and after each immunized mouse was anesthetized, its spleen located on the left side of the body was extracted. The extracted spleen was ground with a mesh to isolate cells, which were mixed with a culture medium (DMEM, Hyclon) to prepare a spleen cell suspension. The suspension was centrifuged to collect a cell layer. The obtained $1\times10^8$ spleen cells were mixed with $1\times10^7$ myeloma cells (Sp2/0), and the mixture was centrifuged to precipitate the cells. The centrifuged precipitate was slowly dispersed, treated with 1 ml of 45% polyethylene glycol (PEG 1500) contained in a culture medium (DMEM), and maintained at 37° C. for one minute before adding 1 ml of a culture medium (DMEM). Subsequently, 10 ml of the culture medium (DMEM) was added for 1 minute to the resultant, which was incubated in a water bath at 37° C. for 5 minutes and then re-centrifuged after the total volume was adjusted to 50 ml. The resulting cell precipitate was re-suspended in an isolation medium (HAT medium) at a concentration of $1~2\times10^5$/ml, and the resultant suspension was distributed at 0.1 ml to the each well of a 96-well plate, which was then incubated in a carbon dioxide incubator at 37° C. to prepare the hybridoma cell groups.

1.2. Production and Purification of a Monoclonal Antibody

The above obtained individual antibody producing hybridomas were screened using a typical ELISA format to select hybridomas which produce 95 anti-Ang2 monoclonal antibodies among the hybridomas differentiated from their mother hybridomas, based on their binding potential with Ang2.

More specifically, to select the hybridoma cells that specifically react only to Ang2 protein among the hybridoma cell groups prepared in Example 1.1 above, an ELISA assay method using a human Ang2 protein as an antigen was used for screening.

Human Ang2 protein was added at 100 ng per each well to a microtiter plate to be adhered to the surface of the plate, and unreacted antigens were removed by washing. 50 microliters of the hybridoma cell culture obtained in Example 1 above was added to each well to react for 1 hour and then, the wells were sufficiently washed with phosphate buffered saline-TWEEN 20 (PBST) solution to remove unreacted culture solution. Goat anti-mouse IgG-horseradish peroxidase (goat anti-mouse IgG-HRP) was added thereto, a reaction was allowed to occur at a room temperature for 1 hour and then, washing was sufficiently performed with the TBST solution. Subsequently, substrate solution (OPD) of peroxidase was added to each well to react, and the reaction degree was measured by the absorption at 450 nm using an ELISA reader to repeatedly select hybridoma cell lines that secret antibodies having specifically high binding affinity only to human Ang2 protein. A limiting dilution was performed on the hybridoma cell lines obtained through repetitive selection to obtain final 58 clones of hybridoma cell lines producing monoclonal antibodies.

Each hybridoma obtained above was cultured in DMEM (Dulbeco's Modified Eagle's Medium) and then, the culture solutions were collected and subjected to Protein G-affinity chromatography method to purify anti-Ang2 monoclonal antibodies produced from each hybridoma.

First, the hybridoma cells cultured in 50 ml of culture medium (DMEM) containing 10% (v/v) FBS were centrifuged to obtain a cell precipitate, which was washed at least twice with 20 ml of PBS to remove the FBS. The cell precipitate was re-suspended in 50 ml of the culture medium (DMEM) and then incubated in a carbon dioxide incubator at 37° C. for 3 days. Subsequently, the cell culture was centrifuged to remove the antibody-producing cells, and the culture medium including the secreted antibodies was isolated and then, stored at 4° C. or used directly. Antibodies were purified from 50 to 300 ml of the culture medium using an AKTA purification device (GE Healthcare) equipped with an affinity column (protein G agarose column; Pharmacia, USA). The purified antibodies were stored for subsequent use after replacing the supernatant with PBS using a filter for protein aggregation (Amicon), and used for the following examples.

1.3. Examination of Functions of Monoclonal Antibodies and Selection of Mouse Anti-Ang2 Antibody 10D6

As Ang2 induces a change in vascular endothelial cells by binding to a Tie-2 receptor expressed in the vascular endothelial cells to induce the phosphorylation of the receptor and activate it, a test for analyzing an influence of the anti-Ang2 antibody on Tie2 phosphorylation was conducted using a cell-based assay.

For this, HUVEC (ATCC) cells ($1 \times 10^5$ cells) were cultured in a 100 mm culture dish using EGM-2 (Lonza) media at 37° C. and when they reached 80~90% confluency, the media were replaced with serum-free medium (Lonza) and cultured at 37° C. for 6 to 16 hours. The dish was washed once with PBS and after the replacement with 1 nM sodium orthovanadate (Sigma)-mixed serum free media (Lonza), they were further cultured for 10 min. After washed once again with PBS, the cultured cells were treated with a mixture prepared by mixing the anti-Ang2 antibody (10D6) having various concentrations (600~0.06 nM) with 40 nM of Ang2 protein (R&D systems) and letting them stand for 20 min. and further cultured for 10 min.

The cells were washed using PBS, treated with 400 µl of a lysis buffer (Roche), collected to a tube to be dissolved at 4° C. for 30 min. and then, centrifuged at 13,000 rpm for 15 min. to measure a supernatant using Nanodrop. 1 µg of Tie2 antibody (R&D system) was added to 0.8 mg of a cell lysate, which was then overnight reacted at 4° C. and then subjected to immunoprecipitation by the addition of protein A bead (GE Healthcare) thereto. The thus obtained reactant was centrifuged at 13,000 rpm for 15 min. to obtain a pellet, which was washed two to three times with a lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto Nitrocellulose membrane (Invitrogen).

To examine the presence of the phosphorylation of Tie2, the membranes were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min, then blocked again and identified using an anti-Tie2 antibody (Santa cruz). An antibody, which shows more intensive ability to induce a phosphorylation of Tie2 receptor when it is added together with Ang2 at the concentration of 60 nM, compared to the case treated with Ang2 only, was selected and named as 10D6.

The hybridoma producing 10D6 was deposited in the Korean Cell Line Bank located at Yongon-dong, Chongno-gu, Seoul, South Korea, as of Apr. 23, 2013 and received accession number KCLRF-BP-00295.

1.4. Analysis of Binding Affinity of Mouse Antibody 10D6 to Ang2

The binding affinity of the above antibody to human Ang2 protein was measured by an surface plasmon resonance (SPR) method using a BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). 6 µg/ml of a recombinant hAng2 (C-His, R&D Systems) protein was flowed onto the chip to be captured at 100 to 200 RU levels. The antibody obtained in Example 2 above was diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. With regard to hAng2, such experiments were conducted, and the results are as shown in the following Table 4.

TABLE 4

| antibody | hAng2 (Kd) |
|---|---|
| SAIT-ANG2-AB-m10D6 | 8.0 nM |

1.5. ELISA Assay for Identifying Formation of 10D6-Ang2-Tie2 Complex

As it was confirmed that 10D6 anti-Ang2 antibody activates Tie2 signaling without inhibiting Ang2-Tie2 binding, an ELISA was conducted to see whether a complex between the antibody and Ang2:Tie2 receptor is formed.

A 96-well MaxiSorp™ flat-bottom plate (Nunc) was coated with 4 µg/ml of Tie2-Fc (R&D systems) or BSA (Sigma). Then, the plate was washed five times with 0.05% (v/v) Tween-20-containing PBS (Phosphate Buffer Saline) and blocked with 1% (v/v) BSA (Bovine serum albumin; Sigma)-containing PBS at a room temperature for 2 hours. 0.25 µg/ml of Ang2 and 2 µg/ml of 10D6 antibody were added to each well of the plate, which was allowed to react at a room temperature for 2 hours and then washed five times with PBST. After that, an anti-mouse IgG antibody (Sigma) conjugated with HRP diluted in 1% (v/v) BSA-containing PBS at a ratio of 1:5,000 (v/v) was added in an amount of 100 µl to each well to react at a room temperature for 1 hour and then, the plate was washed five times with PBST. Lastly, 100 µl (microliter) of TMB substrate (Cell Signaling) was added to each well of the plate to induce color development for 3 min. and then, the reaction was ceased by the addition of 100 µl of Stop solution (Cell Signaling) and OD450 values were measured on a plate reader (Molecular Devices).

Figure 6:
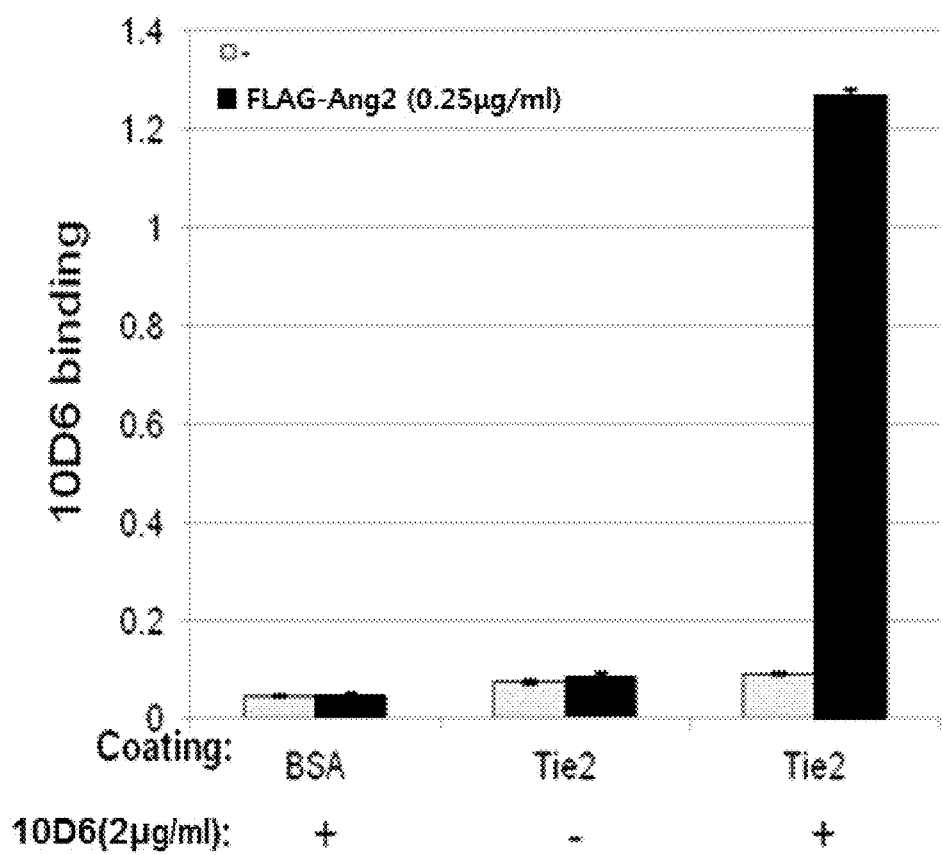
FIG. 6 is a graph of the ELISA results showing the formation of a complex by the binding of an anti-Ang2 antibody with Ang2 and Tie2.
Figure 7:
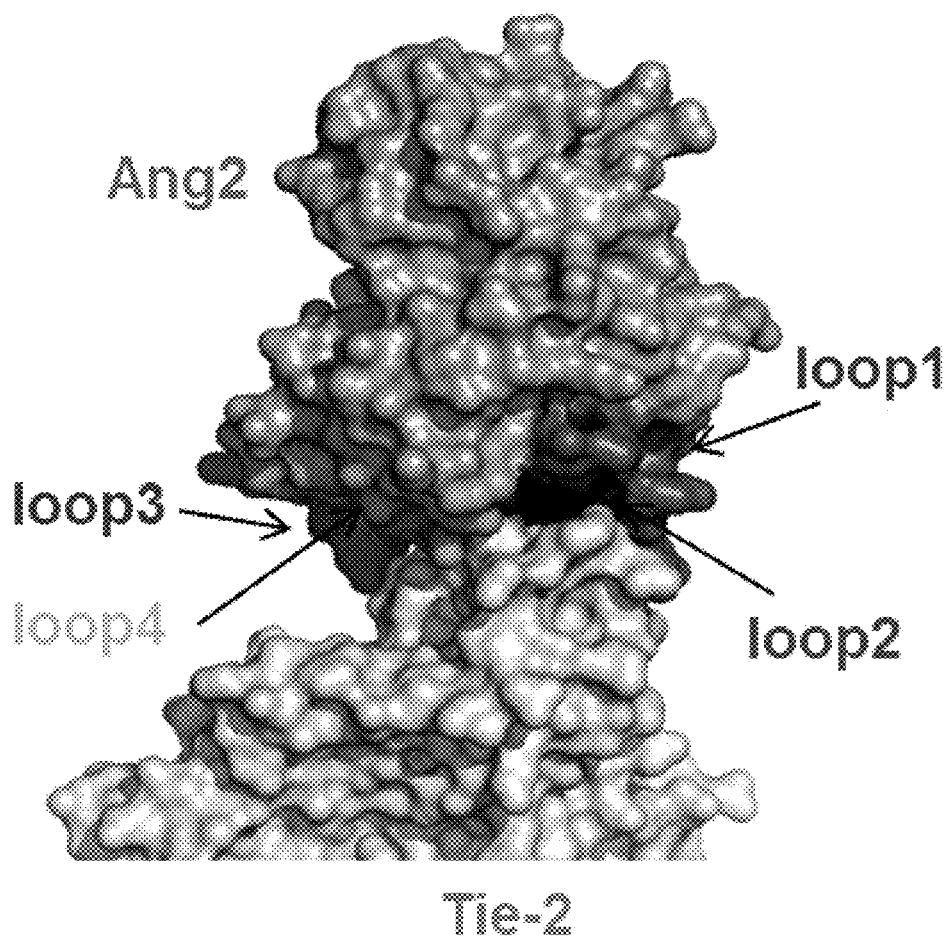
FIG. 7 is a three-dimensional structure of the complex of Ang2 and Tie2, showing the positions of loops 1-4.

The thus obtained results are shown in FIG. 6. As seen in FIG. 6, it was confirmed that 10D6 antibody formed a complex by binding to Ang2 which was bound to Tie2.

1.6. Competition ELISA Assay of Mouse Antibody 10D6 to Ang2-Tie2 Binding

Ang2-Tie2 binding competition ELISA was conducted using the antibody binding to Ang2 prepared in Example 1.3 above.

More specifically, MaxiSorp™ flat-bottom plate (Nunc) of 96-well was coated with hTie2-Fc (R&D Systems) which is a protein bound with 4 µg (microgram)/ml of Fc of human IgG1. After that, the plate was washed five times with 0.05% (v/v) Tween-20-containing PBS (phosphate buffer saline) and then blocked with 1% (v/v) BSA (bovine serum albumin; Sigma)-containing PBS at a room temperature for 2 hour.

For Ang2:Tie2 competition ELISA, each anti-Ang2 antibody obtained in Example 2 was placed at various concentrations of 400 nM to 0.001 nM into each well coated with the hTie-2/Fc fusion protein along with 1% (v/v) BSA and 400 ng/ml of a FLAG-tagged hAng2 and then, the plate was allowed to react at a room temperature for 2 hours and washed five times with PBST. After that, an anti-FLAG antibody (Sigma) conjugated with HRP diluted in 1% (v/v) BSA-containing PBS at a ratio of 1:5,000 (v/v) was added in an amount of 100 µl (microliter) to each well to react at a room temperature for 1 hour and then, the plate was washed five times with PBST. Lastly, 100 µl (microliter) of TMB substrate (Cell Signaling) was added to each well of the plate to induce color development for 3 min. and then, the reaction was ceased by the addition of 100 µl of Stop solution (Cell Signaling) and OD450 values were measured on a plate reader (Molecular Devices).

For comparison, the same test was carried out using 4H10 which is an anti-Ang2 antibody inhibiting Ang2-Tie2 binding. The 4H10 is an antibody having the following heavy chain variable region and light chain variable region.

```
Heavy chain variable region (SEQ ID NO: 12):
EVQLLESGGGLVQPGGSLRLSCAASGFTFSSYDMSWVRQAPGKGLEWVS

LISPDSSSIYYADSVKGRFTISRDNSKNTLYLQMNSLRAEDTAVYYCAKD

LISFWRGGFDYWGQGTLVTVSS

Light chain variable region (SEQ ID NO: 13)
QSVLTQPPSASGTPGQRVTISCSGSSSNIGSNYVNWYQQLPGTAPKLLI

YADSNRPSGVPDRFSGSKSGTSASLAISGLRSEDEADYYCGSWDYSLSG

YVFGGGTKLTVLG
```

An inhibitory degree (%) against Ang2-Tie2 binding is shown in FIG. 1. As seen in FIG. 1, unlike 4H10 which is an anti-Ang2 antibody inhibiting Ang2-Tie2 binding, antibody 10D6 did not inhibit binding between Ang2-Tie2 receptor.

Example 2: Gene Cloning of Mouse Antibody 10D6

A whole RNA was obtained using RNeasy mini kit (Qiagen) from the antibody-producing hybridoma ($2 \times 10^6$ cells) obtained from Example 1.3 above. Then, by using this as a template, only the gene sequence of the heavy chain and light chain variable regions of the monoclonal antibody to be produced in the hybridoma was amplified using a OneStep RT-PCR kit (Qiagen), a Mouse Ig-Primer Set (Novagen), and a thermocycler (GeneAmp PCR System 9700, Applied Biosystem) under the following conditions: 5 min. at 94° C.; [30 min. at 50° C., 15 min. at 95° C.], [1 min. at 94° C., 1 min. at 50° C., 2 min. at 72° C.]×35 cycles; 6 min. at 72° C.; cooling to 4° C.

The PCR products obtained from each reaction were subjected to a direct DNA sequencing to obtain the amino acid sequences of the CDR, heavy chain variable regions and light chain variable regions of the antibody, and nucleotide sequences encoding them, and the obtained results are set forth in the following Tables 5 to 8.

TABLE 5

| | Amino acid sequence of heavy chain CDR | | |
|---|---|---|---|
| Antibody | CDRH1-KABAT | CDRH2-KABAT | CDRH3-KABAT |
| SAIT-ANG2-AB-m10D6 | SDYAWN (SEQ ID NO: 1) | YINYSGNTDYNPSLKS (SEQ ID NO: 2) | GNFEGAMDY (SEQ ID NO: 3) |

TABLE 6

| | Amino acid sequence of light chain CDR | | |
|---|---|---|---|
| Antibody | CDRL1-KABAT | CDRL2-KABAT | CDRL3-KABAT |
| SAIT-ANG2-AB-m10D6 | KASQSVSNDVA (SEQ ID NO: 4) | YASNRYP (SEQ ID NO: 5) | QQDYSSPWT (SEQ ID NO: 6) |

TABLE 7

| Antibody | Sequence of heavy chain variable region |
|---|---|
| SAIT-ANG2-AB-m10D6 | DVQLQESGPDLVKPSQSLSLTCTVTGYSITSDYAWNWIRQ FPGNKLEWMGYINYSGNTDYNPSLKSRSSITRDTSKNQFFL QLNSVTTGDTATYYCARGNFEGAMDYWGQGTSVTVS S(SEQ ID NO: 7) |

TABLE 7-continued

Antibody Sequence of heavy chain variable region

GATGTGCAGCTTCAGGAGTCGGGACCTGACCTGGTGAAACC
TTCTCAGTCTCTGTCCCTCACCTGCACTGTCACTGGCTACTC
AATCACCAGTGATTATGCCTGGAACTGGATCCGGCAGTTTCC
AGGAAACAAACTGGAGTGGATGGGCTACATAAACTACAGTGG
TAACACTGACTACAACCCATCTCTCAAAAGTCGAAGCTCTAT
CACTCGAGACACATCCAAGAACCAGTTCTTCCTGCAGTTGAA
TTCTGTGACTACTGGGGACACAGCCACATATTACTGTGCAAG
AGGTAACTTCGAAGGTGCTATGGACTACTGGGGTCAAGGAA
CCTCAGTCACCGTCTCCTCA(SEQ ID NO: 8)

TABLE 8

Antibody Sequence of light chain variable region

SAIT-      SIVMTQTPKFLLVSAGDRVTITCKASQSVSNDVAWYQQKPGQ
ANG2-      SPKLLIYYASNRYPGVPDRFTGSGYGTDFTFTISTVQAEDLA
AB-m10D6   VYFCQQDYSSPWTFGGGTKLEIK(SEQ ID NO: 9)

agtattgtgatgacccagactcccaaattcctgcttgtatc
agcaggagacaggttaccataacctgcaaggccagt
cagagtgtgagtaatgatgtagcttggtaccaacaga
agccagggcagtctcctaaactgctgatatactatgc
atccaatcgctacctggagtccctgatcgcttcactgg
cagtggatatgggacggatttcactttcaccatcagcac
tgtgcaggctgaagacctggcagtttatttctgtcagca
ggattatagctctccgtggacgttcggtggaggcacca
agctggaaatcaaa(SEQ ID NO: 10)

(In above Tables 6 and 7, underlined bold letters are CDR1, CDR2, and CDR3 in sequence)

Based on the sequence information obtained above, single chain DNAs encoding the heavy chain variable region and the light chain variable region, respectively, were prepared, and cloned into vectors comprising a human kappa constant region coding gene and a CH1 region coding gene of human IgG1, respectively. In particular, a DNA fragment having the heavy chain variable region coding nucleotide sequence (SEQ ID NO: 8) was cloned into a vector of pOptiVEC™-TOPO TA Cloning Kit comprised in OptiCHO™ Antibody Express Kit (Cat no. 12762-019; Invitrogen), and a DNA fragment having the light chain variable region coding nucleotide sequence (SEQ ID NO: 10) was cloned into a vector of pcDNA™3.3-TOPO TA Cloning Kit (Cat no. 8300-01), using EcoRI (NEB, R0101S) and XhoI (NEB, R0146S), to construct a vector comprising the heavy chain variable region and a vector comprising the light chain variable region for expressing a chimeric antibody.

Example 3: Preparation of an scFv of Mouse Antibody 10D6

A gene for producing an scFv fragment using the heavy chain variable region and the light chain variable region of mouse antibody 10D6 was designed. The heavy chain variable region (amino acid sequence: SEQ ID NO: 7; coding nucleotide sequence: SEQ ID NO: 8) and the light chain variable region (amino acid sequence: SEQ ID NO: 9; coding nucleotide sequence: SEQ ID NO: 10) were linked to form 'VH-linker-VL' construct, and the linker is designed to have the amino acid sequence of 'GGGGSGGGGSGGGGS (SEQ ID NO: 76)'. The amino acid sequence of the designed 'VH-linker-VL' (scFv of 10D6) is represented in SEQ ID NO: 80 and the coding nucleotide sequence thereof is represented in SEQ ID NO: 81.

Example 4: Preparation of Gene Library for Affinity Maturation 4.1. Selection of Target CDR and Preparation of Primers To perform affinity maturation, six complementary determining regions (CDRs) were defined from the prepared mouse antibody 10D6 according to the 'Kabat numbering' rule. The CDRs are summarized in Table 9:

TABLE 9

| CDR | Amino acid sequence |
|---|---|
| CDR-H1 | SDYAWN(SEQ ID NO: 1) |
| CDR-H2 | YINYSGNTDYNPSLKS(SEQ ID NO: 2) |
| CDR-H3 | GNFEGAMDY(SEQ ID NO: 3) |
| CDR-L1 | KASQSVSNDVA(SEQ ID NO: 4) |
| CDR-L2 | YASNRYP(SEQ ID NO: 5) |
| CDR-L3 | QQDYSSPWT(SEQ ID NO: 6) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of 10D6 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

4.2. Construction of Gene Library of scFv of 10D6 Antibody

Figure 3:
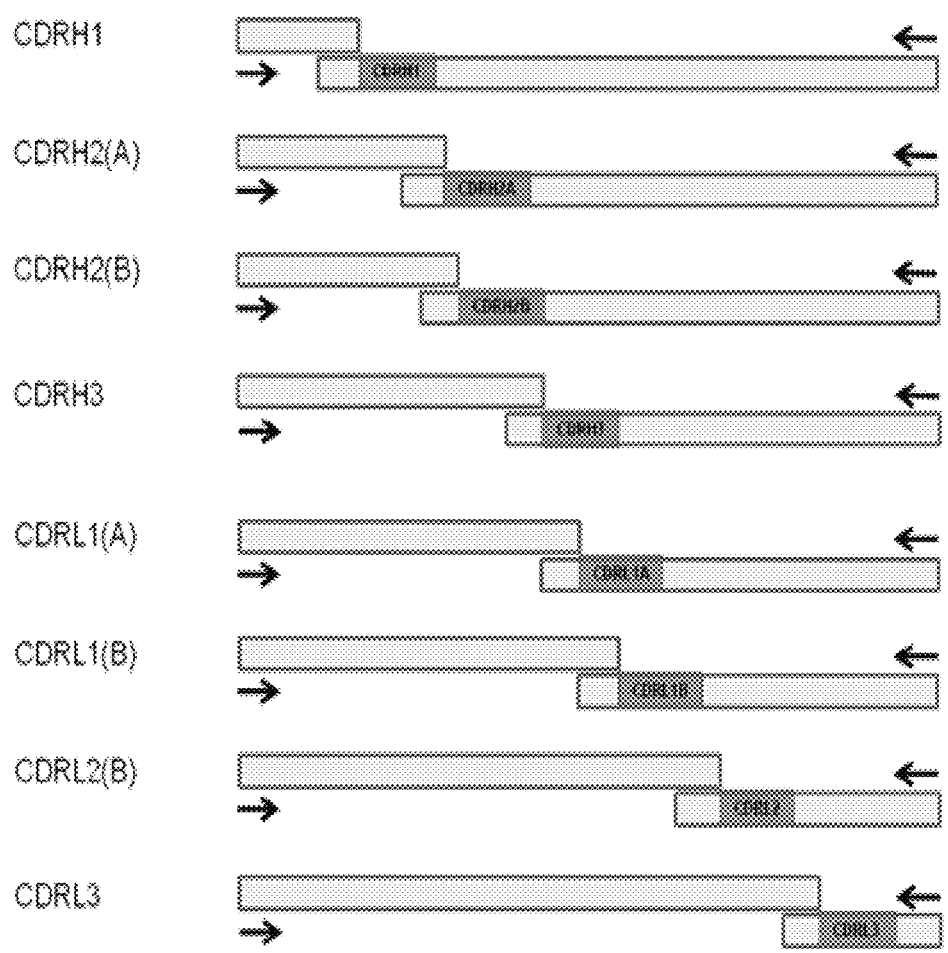
FIG. 3 is a schematic view of a process of overlap extension PCR for obtaining scFv library genes of 10D6 mutants where a desired CDR is mutated in one embodiment.

The construction of antibody gene libraries through the introduction of random sequences was carried out using the primers synthesized in the same manner as in Example 4.1. Two PCR products were obtained using a polynucleotide covering the 10D6 scFv (SEQ ID NO: 81) as a template (see FIG. 3), and were subjected to overlap extension PCR to give scFv library genes for 10D6 antibodies in which only desired CDRs were mutated. $10^7$~$10^8$ libraries targeting each of the six CDRs prepared from the scFv library genes were constructed.

The affinity for Ang2 of each library was compared to that of the wild-type. Most libraries were lower in affinity for Ang2, compared to the wild-type. However, in some mutants, the affinity for Ang2 was retained.

Example 5: Selection of Antibody with Improved Affinity from Libraries

Among the scFv libraries provided in Example 4, the scFv fragments showing upper 1.0 percent of affinity to Ang-2 were selected, and this process was repeated four times. The nucleotide sequence of each of the selected scFv was analyzed. The obtained nucleotide sequences are summarized in Table 10, and were converted into IgG forms (a heavy chain constant region: constant region of human IgG1, a light chain constant region: constant region of human KAPPA Chain). Five antibodies which were respectively produced from clones VH-6.6, VH-6.7, VL-(6.11), VL-(6.17), and VL-HU1 (6.22) were used in the subsequent experiments.

TABLE 10

| clones | Library constructed | CDR sequence |
|---|---|---|
| VH-6.6 | CDR-H2 | KISYSGKTDYNPSLKS (SEQ ID NO: 14) |
| VH-6.7 | CDR-H2 | KINYAGNTDYNPSLKS (SEQ ID NO: 15) |
| VL-(6.11) | CDR-L1 | KASQSVSNDVH (SEQ ID NO: 16) |
| VL-(6.17) | CDR-L3 | QHDYSSPFT (SEQ ID NO: 19) |
| VL-(6.22) | CDR-L1 + CDR-L3 | KASQSVSNDVH (SEQ ID NO: 16) + QHDYSSPFT (SEQ ID NO: 19) |

Example 6: Preparation of Humanized Antibody 10D6-HU1, 10D6-HU2, 10D6-HU3, and 10D6-HU5, from Mouse Antibody 10D6

6.1. Heavy Chain Humanization

To design three domains 10D6-HU1 Heavy, 10D6-HU2-heavy, and 10D6-HU5-heavy, human germline genes which share the highest identity/homology with the VH gene of the mouse antibody 10D6 purified were analyzed through an Ig BLAST (http://www.ncbi.nlm.nih.gov/igblast/). The analysis results revealed that IGHV4-b*01 (DP-67; accession number: Z12367) has an identity/identity/homology of 72% at the amino acid level. CDR-H1 (SEQ ID NO: 1), CDR-H2 (SEQ ID NO: 2), and CDR-H3 (SEQ ID NO: 3) of the mouse antibody 10D6 were defined according to Kabat numbering. A design was made to introduce the CDR of the mouse antibody 10D6 into the framework of IGHV4-b*01 (named as 10D6-HU1; SEQ ID NO: 77; QVQLQES-GPGLVKPSETLSLTCAVSGYSISSDYAWNWIRQPPGK-GLEWIGYINYSGNTD YNPSLKSRVTISVDTSKNQF-SLKLSSVTAADTAVYYCARGNFEGAMDYWGQGTLV TVS S). Hereupon, a back mutation to the amino acid sequence of the mouse 10D6 were conducted at positions 30 (S→T), to establish antibody 10D6-HU5 (SEQ ID NO: 56). Then, 10D6-HU5 was further mutated at positions 48 (I→M), 67 (V→S), and 71 (V→R), to establish 10D6-HU2 (SEQ ID NO: 78; QVQLQESGPGLVKPSETLSLTCAVS-GYSITSDYAWNWIRQPPGKGLEWMGYINYSGNT DYNPSLKSRSTISRDTSKNQFSLKLSSVTAADTAVYY-CARGNFEGAMDYWGQGTLVTV SS).

For use in designing 10D6-HU3-heavy, human antibody frameworks were analyzed by a BLAST search. The result revealed that the Herceptin backbone, which known to show very low immunogenicity of about 0.1% level among the pre-existing humanized antibodies, is very similar in framework and sequence to the mouse antibody 10D6. CDR-H1, CDR-H2, and CDR-H3 of the mouse antibody 10D6 were defined according to Kabat numbering and introduced into the Herceptin backbone to construct H4-heavy (SEQ ID NO: 42), wherein back mutations were conducted at positions 27 (F-Y), 28 (N→S), 30 (K→T), 48 (V→M), 49 (A→G), 67 (F→S), 71 (A→R), 78 (A→F), and 93 (S→A), to establish 10D6-HU3 (SEQ ID NO: 79; EVQLVESGGGLVQPGGSL-RLSCAASGYSITSDYAWNWVRQAPGKGLEWMGYI-NYSGN TDYNPSLKSRSTISRDTSKNTFYLQMNSL-RAEDTAVYYCARGNFEGAMDYWGQGTLVT VSS).

6.2. Light Chain Humanization

To design a H1-light, human germline genes which share the highest identity/homology with the VL gene of the mouse antibody 10D6 were analyzed through an Ig BLAST (NCBI, Bethesday, Md.: available online at <<nebi.nlm.nih.gov/igblast/>>). The analysis results revealed IGKV1-39*01 (O12; accession number: X59315) has an identity/identity/homology of 66% at the amino acid level. CDR-L1 (SEQ ID NO: 4), CDR-L2 (SEQ ID NO: 5), and CDR-L3 (SEQ ID NO: 6) of the mouse antibody 10D6 were defined according to Kabat numbering. A design was made to introduce the CDR of the mouse antibody 10D6 into the framework of IGKV1-39*01.

Thereafter, DNA fragments of heavy chains (10D6-VHHU1, 10D6-VHHU2, 10D6-VHHU3, and 10D6-VHHU5) were respectively cloned into a vector of pOptiVEC™-TOPO TA Cloning Kit enclosed in an OptiCHO™ Antibody Express Kit (Cat no. 12762-019, Invitrogen) using EcoRI (NEB, R0101S) and nheI (NEB, R0131), and a DNA fragment of a light chain (10D6-VLHU1 (SEQ ID NO: 57), coding sequence: SEQ ID NO: 69) was cloned into a vector of pcDNA™3.3-TOPO TA Cloning Kit using EcoRI (NEB, R0101S) and XhoI (NEB, R0146S), to construct recombinant vectors for expressing a humanized antibody.

The constructed vectors were amplified using a Qiagen Maxiprep kit (Cat No. 12662), and the vectors including the heavy chain and the vector including the light chain were added to 293T cells (2.5×10$^7$) at a ratio of about 4:1 (about 80 µg:20 µg) with 360 µl of 2 M CaCl$_2$ and were transfected. Next, the mixture was cultured in a DMEM medium with 10% (w/v) FBS at 37° C. in 5% (v/v) CO$_2$ conditions for 5 hours, and then cultured in a DMEM medium without FBS at 37° C. in 5% (v/v) CO$_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final humanized antibodies 10D6-HU1, 10D6-HU2, 10D6-HU3, and 10D6-HU5 were purified.

Example 7: Incorporation of the Selected CDRs into Humanized Antibody and Transformation to IgG The selected CDRs were incorporated into the heavy chain and the light chain of the humanized antibodies. Polynucleotides encoding the heavy chain of the antibodies were synthesized by Bioneer, Inc. so as to consist of 'EcoRI-signal sequence-VH-NheI-CH-XhoI' (SEQ ID NOs: 64-68). Polynucleotides encoding the light chain of the antibodies were synthesized by Bioneer, Inc. so as to consist of 'EcoRI-signal sequence-VL-BsiWI-CL-XhoI' (SEQ ID NOs: 69-71). The polynucleotides (SEQ ID NOs: 64-68) encoding the heavy chain were respectively cloned into a vector of pOptiVEC™-TOPO TA Cloning Kit included in OptiCHO™ Antibody Express Kit (Cat no. 12762-019; Invitrogen), and the polynucleotides (SEQ ID NOs: 69-71) encoding the light chain were respectively cloned into a vector of pcDNA™3.3-TOPOTA Cloning Kit (Cat no. 8300-01), using EcoRI (NEB, R0101S) and XhoI (NEB, R0146S), to establish vectors for expressing affinity matured antibodies.

The constructed vectors were amplified using a Qiagen Maxiprep kit (Cat No. 12662), and the vectors including the heavy chain and the vector including the light chain were added to 293T cells (2.5×10$^7$) at a ratio of about 4:1 (about 80 µg:20 µg) with 360 µl of 2 M CaCl$_2$ and were transfected. Next, the mixture was cultured in a DMEM medium with 10% (w/v) FBS at 37° C. in 5% (v/v) CO$_2$ conditions for 5 hours, and then cultured in a DMEM medium without FBS at 37° C. in 5% (v/v) CO$_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final affinity-matured antibodies h10D6-Opti-1, h10D6-Opti-2, h10D6-Opti-3, and h10D6-Opti-4 were purified.

TABLE 11

| Clone | Antibody sequence (VH) | Antibody sequence (VL) |
|---|---|---|
| h10D6-OPTI-1 | >HU2-6.6<br>QVQLQESGPGLVKPSETLSLTCAVSGYS ITSDYAWNWIRQPPGKGLEWMGKISYS GKTDYNPSLKSRSTISRDTSKNQFSLKL SSVTAADTAVYYCARGNFEGAMDYW GQGTLVTVSS(SEQ ID NO: 52)<br><br>(coding nucleotide sequence)<br>CAGGTGCAACTGCAGGAGTCAGGCCC CGGCCTGGTAAAACCTTCTGAAACGCT CTCACTTACCTGTGCCGTTAGTGGATA CTCTATCACTTCCGACTACGCTTGGAA TTGGATTCGGCAGCCTCCAGGCAAAG GGCTGGAATGGATGGGAAAGATTTCC TATTCCGGTAAGACTGACTACAATCCC AGTCTGAAGAGCAGGTCAACAATCTC CAGAGACACCAGCAAGAATCAGTTTT CCCTGAAATTGTCCTCGGTGACAGCAG CGGATACCGCAGTGTATTATTGCGCCC GCGGTAACTTCGAGGGAGCTATGGAT TACTGGGGCAGGGTACTCTCGTCACT GTGAGCAGC(SEQ ID NO: 64) | >HU1<br>DIQMTQSPSSLSASVGDRVTITCKASQSV SNDVAWYQQKPGKAPKLLIYYASNRYP GVPSRFSGSGSGTDFTLTISSLQPEDFATY YCQQDYSSPWTFGQGTKLEIK(SEQ ID NO: 57)<br><br>(coding nucleotide sequence)<br>GACATCCAGATGACCCAGTCTCCATCC TCCCTGTCTGCATCTGTAGGAGACAGA GTCACCATCACTTGCAAGGCCAGTCAG AGTGTGAGTAATGATGTAGCTTGGTAT CAGCAGAAACCAGGGAAAGCCCCTAA GCTCCTGATCTATTATGCATCCAATCGC TACCCTGGGGTCCCATCAAGGTTCAGT GGCAGTGGATCTGGGACAGATTTCACT CTCACCATCAGCAGTCTGCAACCTGAA GATTTTGCAACTTACTACTGTCAGCAG GATTATAGCTCTCCGTGGACGTTCGGT GGAGGCACCAAGGTGGAAATCAAA(SEQ ID NO: 69) |
| h10D6-OPTI-2 | >HU2-6.7<br>QVQLQESGPGLVKPSETLSLTCAVSGYS ITSDYAWNWIRQPPGKGLEWMGKINY AGNTDYNPSLKSRSTISRDTSKNQFSLK LSSVTAADTAVYYCARGNFEGAMDYW GQGTLVTVSS(SEQ ID NO: 53)<br><br>(coding nucleotide sequence)<br>CAGGTGCAACTGCAGGAGTCAGGCCC CGGCCTGGTAAAACCTTCTGAAACGCT CTCACTTACCTGTGCCGTTAGTGGATA CTCTATCACTTCCGACTACGCTTGGAA TTGGATTCGGCAGCCTCCAGGCAAAG GGCTGGAATGG ATGGGAAAGATTAACTATGCCGGTAA CACTGACTACAATCCCAGTCTGAAGA GCAGGTCAACAATCTCCAGAGACACC AGCAAGAATCAGTTTTCCCTGAAATTG TCCTCGGTGACAGCAGCGGATACCGC AGTGTATTATTGCGCCCGCGGTAACTT CGAGGGAGCTATGGATTACTGG GGGCAGGGTACTCTCGTCACTGTGAG CAGC(SEQ ID NO: 65) | >HU1<br>DIQMTQSPSSLSASVGDRVTITCKASQSV SNDVAWYQQKPGKAPKLLIYYASNRYP GVPSRFSGSGSGTDFTLTISSLQPEDFATY YCQQDYSSPWTFGQGTKLEIK(SEQ ID NO: 57)<br><br>(coding nucleotide sequence)<br>GACATCCAGATGACCCAGTCTCCATCC TCCCTGTCTGCATCTGTAGGAGACAGA GTCACCATCACTTGCAAGGCCAGTCAG AGTGTGAGTAATGATGTAGCTTGGTAT CAGCAGAAACCAGGGAAAGCCCCTAA GCTCCTGATCTATTATGCATCCAATCGC TACCCTGGGGTCCCATCAAGGTTCAGT GGCAGTGGATCTGGGACAGATTTCACT CTCACCATCAGCAGTCTGCAACCTGAA GATTTTGCAACTTACTACTGTCAGCAG GATTATAGCTCTCCGTGGACGTTCGGT GGAGGCACCAAGGTGGAAATCAAA(SEQ ID NO: 69) |
| h10D6-OPTI-43 | >HU2-6.6<br>QVQLQESGPGLVKPSETLSLTCAVSGYS ITSDYAWNWIRQPPGKGLEWMGKISYS GKTDYNPSLKSRSTISRDTSKNQFSLKL SSVTAADTAVYYCARGNFEGAMDYW GQGTLVTVSS(SEQ ID NO: 52)<br><br>(coding nucleotide sequence)<br>CAGGTGCAACTGCAGGAGTCAGGCCC CGGCCTGGTAAAACCTTCTGAAACGCT CTCACTTACCTGTGCCGTTAGTGGATA CTCTATCACTTCCGACTACGCTTGGAA TTGGATTCGGCAGCCTCCAGGCAAAG GGCTGGAATGG ATGGGAAAGATTTCCTATTCCGGTAAG ACTGACTACAATCCCAGTCTGAAGAG CAGGTCAACAATCTCCAGAGACACCA GCAAGAATCAGTTTTCCCTGAAATTGT CCTCGGTGACAGCAGCGGATACCGCA GTGTATTATTGCGCCCGCGGTAACTTC GAGGGAGCTATGGATTACTGG GGGCAGGGTACTCTCGTCACTGTGAG CAGC(SEQ ID NO: 64) | >HU1-6.11<br>DIQMTQSPSSLSASVGDRVTITCKASQSV SNDVHWYQQKPGKAPKLLIYYASNRYP GVPSRFSGSGSGTDFTLTISSLQPEDFATY YCQQDYSSPWTFGQGTKLEIK(SEQ ID NO: 58)<br><br>(coding nucleotide sequence)<br>GACATCCAGATGACCCAGTCTCCATCC TCCCTGTCTGCATCTGTAGGAGACAGA GTCACCATCACTTGCAAGGCCAGTCAG AGTGTGAGTAATGATGTACATTGGTAT CAGCAGAAACCAGGGAAAGCCCCTAA GCTCCTGATCTATTATGCATCCAATCGC TACCCTGGGGTCCCATCAAGGTTCAGT GGCAGTGGATCTGGGACAGATTTCACT CTCACCATCAGCAGTCTGCAACCTGAA GATTTTGCAACTTACTACTGTCAGCAG GATTATAGCTCTCCGTGGACGTTCGGT GGAGGCACCAAGGTGGAAATCAAA(SEQ ID NO: 70) |

TABLE 11-continued

| Clone | Antibody sequence (VH) | Antibody sequence (VL) |
| --- | --- | --- |
| h10D6-OPTI-55 | >HU2-6.7<br>QVQLQESGPGLVKPSETLSLTCAVSGYS<br>ITSDYAWNWIRQPPGKGLEWMGKINY<br>AGNTDYNPSLKSRSTISRDTSKNQFSLK<br>LSSVTAADTAVYYCARGNFEGAMDYW<br>GQGTLVTVSS(SEQ ID NO: 53)<br><br>(coding nucleotide sequence)<br>CAGGTGCAACTGCAGGAGTCAGGCCC<br>CGGCCTGGTAAAACCTTCTGAAACGCT<br>CTCACTTACCTGTGCCGTTAGTGGATA<br>CTCTATCACTTCCGACTACGCTTGGAA<br>TTGGATTCGGCAGCCTCCAGGCAAAG<br>GGCTGGAATGG<br>ATGGGAAAGATTAACTATGCCGGTAA<br>CACTGACTACAATCCCAGTCTGAAGA<br>GCAGGTCAACAATCTCCAGAGACACC<br>AGCAAGAATCAGTTTTCCCTGAAATTG<br>TCCTCGGTGACAGCAGCGGATACCGC<br>AGTGTATTATTGCGCCCGCGGTAACTT<br>CGAGGGAGCTATGGATTACTGG<br>GGGCAGGGTACTCTCGTCACTGTGAG<br>CAGC(SEQ ID NO: 65) | HU1-6.11<br>DIQMTQSPSSLSASVGDRVTITCKASQSV<br>SNDVHWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 58)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 70) |
| h10D6-OPTI-3 | >HU3-6.6<br>EVQLVE SGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54)<br><br>(coding nucleotide sequence)<br>GAGGTTCAGCTGGTCGAAAGCGGTGG<br>GGGACTCGTGCAGCCAGGCGGTTCTCT<br>TAGATTATGCATGTGCCGCATCCGGGTA<br>CTCCATCACCTCTGATTATGCATGGAA<br>CTGGGTCAGACAAGCCCCCGGAAAGG<br>GCCTGGAGTGGATGGGGAAGATCTCC<br>TATTCAGGGAAGACAGATTATAATCCT<br>TCGCTGAAAAGCAGATCAACAATTAG<br>TAGAGACACTTCTAAAAATACTTTTTA<br>CCTCCAGATGAACAGTCTGCGCGCCG<br>AAGACACCGCCGTGTACTACTGCGCT<br>AGGGGAAATTTCGAGGGAGCTATGGA<br>CTATTGGGGCCAGGGCACGTTGGTAA<br>CCGTGAGCAGC(SEQ ID NO: 66) | >HU1<br>DIQMTQSPSSLSASVGDRVTITCKASQSV<br>SNDVAWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 57)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTAGCTTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 69) |
| h10D6-OPTI-4 | >HU3-6.7<br>EVQLVESGGGLVQPGGSLRLSCAASGY<br>SITSDYAWNWVRQAPGKGLEWMGKIN<br>YAGNTDYNPSLKSRSTISRDTSKNTFYL<br>QMNSLRAEDTAVYYCARGNFEGAMD<br>YWGQGTLVTVSS(SEQ ID NO: 55)<br><br>(coding nucleotide sequence)<br>GAGGTTCAACTGGTAGAGTCCGGGGG<br>CGGCCTGGTCCAGCCAGGAGGAAGCC<br>TGCGGCTCTCTTGTGCCGCCAGCGGGT<br>ATAGTATCACTTCAGATTATGCCTGGA<br>ATTGGGTCCGCCAGGCCCCCGGGAAG<br>GGCTTAGAGTGGATGGGTAAAATTAA<br>TTACGCAGGCAACACCGACTATAATC<br>CTTCACTGAAATCTAGATCCACCATCT<br>CTAGAGATACAAGTAAGAACACCTTT<br>TACTTGCAGATGAATAGCCTCAGGGCT<br>GAAGACACTGCTGTGTACTACTGCGCG<br>AAGAGGAAACTTCGAAGGAGCGATGG<br>ATTATTGGGGCCAGGGTACGCTTGTGA<br>CAGTGTCCTCT(SEQ ID NO: 67) | >HU1<br>DIQMTQSPSSLSASVGDRVTITCKASQSV<br>SNDVAWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 57)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTAGCTTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 69) |

TABLE 11-continued

| Clone | Antibody sequence (VH) | Antibody sequence (VL) |
|---|---|---|
| h10D6-OPTI-16 | >HU3-6.6<br>EVQLVESGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54)<br><br>(coding nucleotide sequence)<br>GAGGTTCAGCTGGTCGAAAGCGGTGG<br>GGGACTCGTGCAGCCAGGCGGTTCTCT<br>TAGATTATCATGTGCCGCATCCGGGTA<br>CTCCATCACCTCTGATTATGCATGGAA<br>CTGGGTCAGACAAGCCCCCGGAAAGG<br>GCCTGGAGTGGATGGGGAAGATCTCC<br>TATTCAGGGAAGACAGATTATAATCCT<br>TCGCTGAAAAGCAGATCAACAATTAG<br>TAGAGACACTTCTAAAAATACTTTTTA<br>CCTCCAGATGAACAGTCTGCGCGCCG<br>AAGACACCGCCGTGTACTACTGCGCT<br>AGGGGAAATTTCGAGGGAGCTATGGA<br>CTATTGGGGCCAGGGCACGTTGGTAA<br>CCGTGAGCAGC(SEQ ID NO: 66) | >HU1-6.11<br>DIQMTQSPSSLSASVGDRVTITCKASQSV<br>SNDVHWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 58)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 70) |
| h10D6-OPTI-17 | >HU3-6.7<br>EVQLVESGGGLVQPGGSLRLSCAASGY<br>SITSDYAWNWVRQAPGKGLEWMGKIN<br>YAGNTDYNPSLKSRSTISRDTSKNTFYL<br>QMNSLRAEDTAVYYCARGNFEGAMD<br>YWGQGTLVTVSS(SEQ ID NO: 55)<br><br>(coding nucleotide sequence)<br>GAGGTTCAACTGGTAGAGTCCGGGGG<br>CGGCCTGGTCCAGCCAGGAGGAAGCC<br>TGCGGCTCTCTTGTGCCGCCAGCGGGT<br>ATAGTATCACTTCAGATTATGCCTGGA<br>ATTGGGTCCGCCAGGCCCCCGGGAAG<br>GGCTTAGAGTGGATGGGTAAAATTAA<br>TTACGCAGGCAACACCGACTATAATC<br>CTTCACTGAAATCTAGATCCACCATCT<br>CTAGAGATACAAGTAAGAACACCTTT<br>TACTTGCAGATGAATAGCCTCAGGGCT<br>GAAGACACTGCTGTGTACTACTGCGCG<br>AAGAGGAAACTTCGAAGGAGCGATGG<br>ATTATTGGGGCCAGGGTACGCTTGTGA<br>CAGTGTCCTCT(SEQ ID NO: 67) | >HU1-6.11<br>DIQMTQSPSSLSASVGDRVTITCKASQSV<br>SNDVHWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 58)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 70) |
| h10D6-OPTI-42 | >HU5<br>QVQLQESGPGLVKPSETLSLTCAVSGYS<br>ITSDYAWNWIRQPPGKGLEWIGYINYS<br>GNTDYNPSLKSRVTISVDTSKNQFSLKL<br>SSVTAADTAVYYCARGNFEGAMDYW<br>GQGTLVTVSS(SEQ ID NO: 56)<br><br>(coding nucleotide sequence)<br>CAGGTGCAGCTGCAGGAGTCGGGCCC<br>AGGACTGGTGAAGCCTTCGGAGACCC<br>TGTCCCTCACCTGCGCTGTCTCTGGTT<br>ACTCCATCACCAGTGATTATGCCTGGA<br>ACTGGATCCGGCAGCCCCCAGGGAAG<br>GGGCTGGAGTGGATTGGGTACATAAA<br>CTACAGTGGTAACACTGACTACAACC<br>CATCTCTCAAAAGTCGAGTCACCATAT<br>CAGTAGACACGTCCAAGAACCAGTTC<br>TCCCTGAAGCTGAGCTCTGTGACCGCC<br>GCAGACACGGCCGTGTATTACTGTGC<br>GAGAGGTAACTTCGAAGGTGCTATGG<br>ACTACTGGGGTCAAGGAACGCTTGTG<br>ACAGTGTCCTCT(SEQ ID NO: 68) | >HU1-22<br>DIQMTQSPSSLSASVGDRVTITCKASQSV<br>SNDVHWYQQKPGKAPKLLIYYASNRYP<br>GVPSRFSGSGSGTDFTLTISSLQPEDFATY<br>YCQHDYSSPFTFGQGTKLEIK(SEQ ID<br>NO: 59)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAT<br>GATTATAGCTCTCCGTTCACGTTCGGTG<br>GAGGCACCAAGGTGGAAATCAAA(SEQ<br>ID NO: 71) |

(In Table 11, the bold letters are CDR1, CDR2, and CDR3 in sequence)

Example 8: Analysis of Binding Affinity of Selected Antibodies

The binding affinity (KD values) of the antibodies to human Ang2 protein was measured by an SPR method using a BIAcore T100 (GE Healthcare). 25 μg/ml anti-His antibody was immobilized on a CM5 sensor chip (GE healthcare) using a pH 5.0 acetate solution and an amine coupling kit (GE Healthcare). 6 μg/ml of a recombinant hAng2 (C-His, R&D Systems) protein was flowed onto the chip to be captured at 100 to 200 RU levels. The antibodies obtained in the above examples were diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. The KD values were calculated from the values of $k_{on}$, $k_{off}$, and the results are as shown in the following Table 12.

TABLE 12

| Antibody | kon (1/Ms) | koff (1/s) | KD (nM) |
| --- | --- | --- | --- |
| m10D6 | $2.410 \times 10^4$ | $1.932 \times 10^{-4}$ | 8 |
| 10D6-HU1 | $3.082 \times 10^4$ | 0.002599 | 84 |
| 10D6-HU2 | $7.298 \times 10^4$ | 0.003464 | 47 |
| 10D6-HU3 | $4.503 \times 10^4$ | 0.001938 | 43 |
| 10D6-HU5 | $4.856 \times 10^4$ | 0.003115 | 64 |
| h10D6-OPTI-1 | $4.737 \times 10^5$ | $3.209 \times 10^{-4}$ | 0.68 |
| h10D6-OPTI-2 | $4.237 \times 10^5$ | $1.488 \times 10^{-4}$ | 0.34 |
| h10D6-OPTI-43 | $1.531 \times 10^6$ | $5.760 \times 10^{-4}$ | 0.38 |
| h10D6-OPTI-55 | $6.210 \times 10^5$ | $8.489 \times 10^{-5}$ | 0.14 |
| h10D6-OPTI-3 | $6.239 \times 10^5$ | $3.070 \times 10^{-4}$ | 0.49 |
| h10D6-OPTI-4 | $7.357 \times 10^5$ | $2.460 \times 10^{-4}$ | 0.33 |
| h10D6-OPTI-16 | $4.794 \times 10^5$ | $4.434 \times 10^{-4}$ | 0.92 |
| h10D6-OPTI-17 | $4.600 \times 10^5$ | $3.503 \times 10^{-4}$ | 0.76 |
| h10D6-OPTI-42 | $3.358 \times 10^5$ | $2.862 \times 10^{-4}$ | 0.85 |

As shown in Table 12, the affinity to Ang2 of the mouse antibody 10D6 is about 8 nM, the affinities to Ang2 of the 5 affinity-matured and humanized antibodies are from about 0.14 nM to about 0.92 nM. The results indicate that the affinity to Ang2 can be improved at least about 5 times up to about 37 times in the affinity-matured antibodies in an IgG form transformed from a scFv form.

Example 9: Analysis of In Vitro Biological Property of the Selected Affinity-Matured Antibodies—Akt Phosphorylation To examine whether the humanized and/or affinity-matured 10D6 antibodies can induce activation of downstream signaling as well as Tie2 receptor, the levels of Akt phosphorylation in HUVEC (ATCC) cells treated with Ang2 and each of the antibodies (see Table 11) of Example 7 were measured and compared to that of the case treated with Ang2 only. HUVEC (ATCC) cells ($2 \times 10^4$ cells) were cultured in 96 well plate using EGM-2 medium (Lonza) at 37° C., and when they reached 80~90% confluency, the media were replaced with serum-free medium (Lonza) and cultured at 37° C. for 6 hours. The cultured cells were treated with a mixture prepared by mixing 6 nM or 1.2 nM of each of the anti-Ang2 antibodies of Example 7 with 4 nM of Ang2 protein (R&D systems) and letting them stand for 20 min. and further cultured for 30 min.

The phosphorylation of Akt which participates in downstream signaling of Tie2 receptor was examined using PathScan® Phospho-Akt Chemiluminescent Sandwich ELISA Kit (Cell signaling, #7134). The cells were washed using PBS, treated with 30 μl of a lysis buffer (Roche), to be subjected to cell lysis at 4° C. for 30 minutes. Then, 30 μl of diluent buffer (Cell signaling) was added to each well and sufficiently mixed with pipet, and 50 μl of the diluted product was collected and transferred to a phosphor-Akt Ab coated microwell, to react at room temperature for 2 hours. After 2 hours, the well was washed with 1× washing buffer (Cell signaling) four times, and treated with 50 μl of Akt1 detection antibody solution (Cell signaling), to react at room temperature for one hour. As the same process, the well was washed, and reacted with 50 μl of HRP-conjugated secondary antibody (Cell signaling) at room temperature for 30 minutes. As the same process, the well was washed, and treated with 50 μl of a mixture solution of luminol/enhancer solution (GE healthcare) and stable peroxide buffer (GE healthcare) at the ratio of 1:1 (v/v). Then the plate was placed in a luminometer (Envision 2104 plate reader, Perkin Elmer), to measure a relative light unit (RLU).

Figure 2:
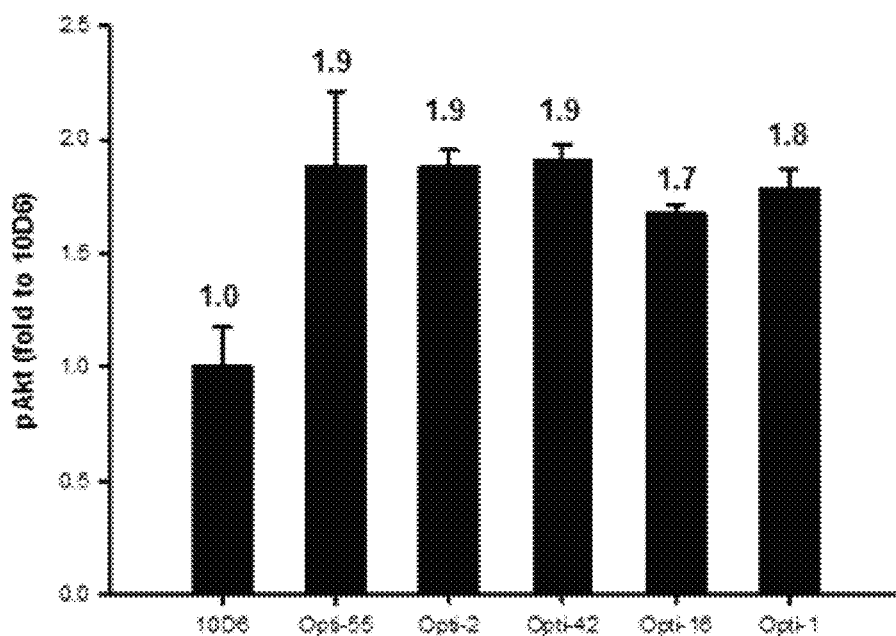
FIG. 2 is a series of graphs showing the phosphorylation level of Akt that participated in downstream signaling of Tie2 receptor, by humanized and affinity-matured anti-Ang2 antibodies as compared to a control.
Figure 2:
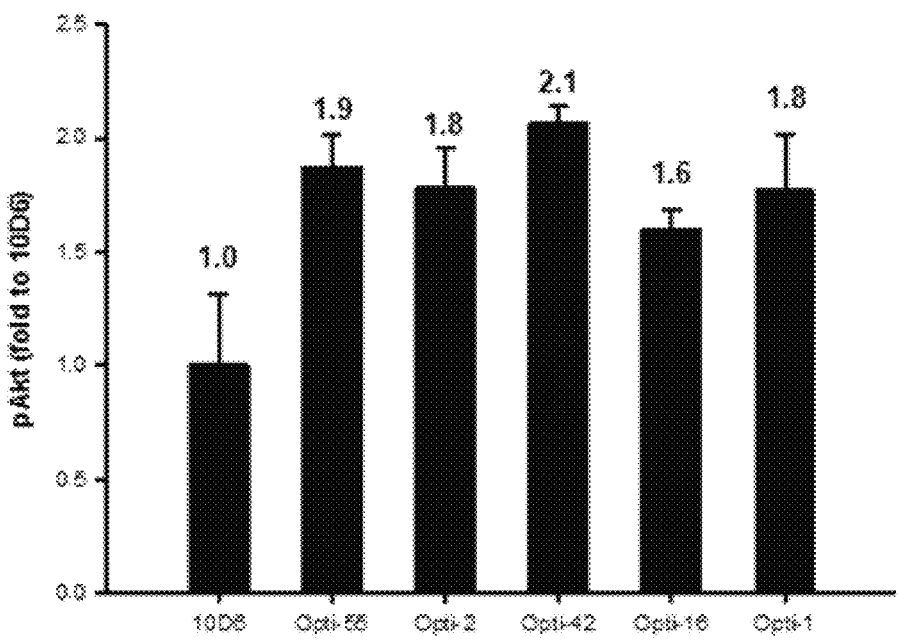

The obtained results are shown in FIG. 2. As seen in FIG. 2, the humanized and/or affinity-matured antibodies of Example 7 induce the downstream signaling more intensively compared to mouse antibody 10D6.

Example 10: Synthesis of a Polynucleotide for Preparing an scFv of Humanized Antibody of 10D6 (Opti-1)

The gene for preparing scFv of a humanized 10D6 antibody was designed using the heavy chain variable region and the light chain variable region of humanized 10D6 antibody Opti-1. The heavy chain variable region (amino acid sequence: Hu2 6.6 (SEQ ID NO: 52); coding nucleotide sequence: SEQ ID NO: 64), and the light chain variable region (amino acid sequence: SEQ ID NO: Hu1 (SEQ ID NO: 57); coding nucleotide sequence: SEQ ID NO: SEQ ID NO: 69) were linked to form a 'VH-linker-VL' construct, and the linker was designed so as to have the amino acid sequence of 'GGGGSGGGGSGGGGS(SEQ ID NO: 76)'. The polynucleotide (SEQ ID NO: 83) encoding the designed scFv ('VH-linker-VL; SEQ ID NO: 82) of antibody 10D6 opti-1 was synthesized by Bioneer, Inc.

Example 11: Preparation of Gene Library for the Secondary Affinity Maturation 11.1. Selection of Target CDR and Preparation of Primers To perform affinity maturation of antibody 10D6 opti-1, three complementary determining regions (CDRs) were defined from the prepared antibody 10D6 opti-1 according to the 'Kabat numbering' rule. The CDRs are summarized in Table 13:

TABLE 13

| CDR | amino acid sequence |
| --- | --- |
| CDR-L1 | KASQSVSNDVA (SEQ ID NO: 4) |
| CDR-L2 | YASNRYP (SEQ ID NO: 5) |
| CDR-L3 | QQDYSSPWT (SEQ ID NO: 6) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of 10D6 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

11.2. Construction of Gene Library of scFv of 10D6 Opti-1 Antibody

Figure 4:
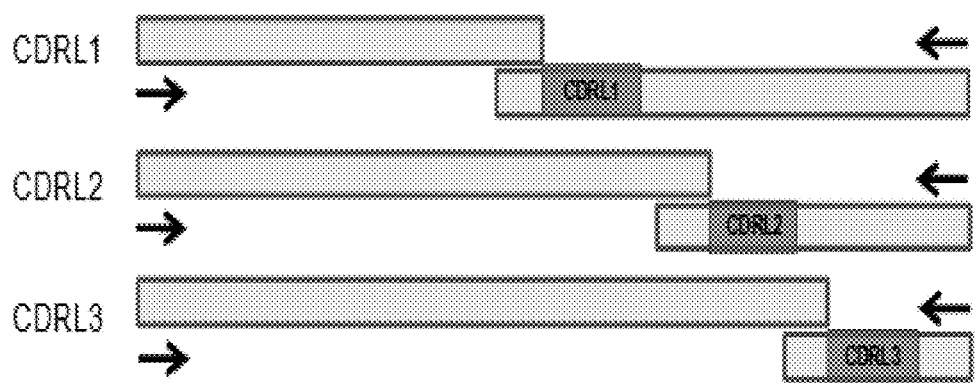
FIG. 4 is a schematic view of a process of overlap extension PCR for obtaining scFv library genes of 10D6 mutants where a desired CDR is mutated in another embodiment.

The construction of antibody gene libraries through the introduction of random sequences was carried out using the primers synthesized in the same manner as in Example 11.1. Two PCR products were obtained using a polynucleotide covering the 10D6 opti-1 scFv (SEQ ID NO: 83) as a template (see FIG. 4), and were subjected to overlap extension PCR to give scFv library genes for 10D6 antibodies in which only desired CDRs were mutated. $10^7$~$10^8$ libraries targeting each of the six CDRs prepared from the scFv library genes were constructed.

The affinity for Ang2 of each library was compared to that of the wild-type. Most libraries were lower in affinity for Ang2, compared to the wild-type. However, in some mutants, the affinity for Ang2 was retained.

Example 12: Selection of Antibody with Improved Affinity from Libraries

Among the scFv libraries provided in Example 11, the scFv fragments showing upper 1.0 percent of affinity to Ang-2 were selected, and this process was repeated four times. The nucleotide sequence of each of the selected scFv was analyzed. The obtained nucleotide sequences are summarized in Table 14, and were converted into IgG forms (a heavy chain constant region: constant region of human IgG1, a light chain constant region: constant region of human KAPPA Chain). Four antibodies which were respectively produced from clones 10D6_VL-Hu1-2.1, 10D6_VL-Hu1-2.4, 10D6_VL-Hu1-2.7, 10D6_VL-Hu1-2.8 were used in the subsequent experiments.

TABLE 14

| Clones | Library constructed | CDR sequence |
|---|---|---|
| 10D6_VL-Hu1-2.1 | CDR-L1 | KASQFVSTDVH (SEQ ID NO: 17) |
| 10D6_VL-Hu1-2.4 | CDR-L2 | YASIPYP (SEQ ID NO: 18) |
| 10D6_VL-Hu1-2.7 | CDR-L1 + L2 | KASQSVSNDVH (SEQ ID NO: 16) + YASIPYP (SEQ ID NO: 18) |

TABLE 14-continued

| Clones | Library constructed | CDR sequence |
|---|---|---|
| 10D6_VL-Hu1-2.8 | CDR-L1 + L2 | KASQFVSTDVH (SEQ ID NO: XX) + YASIPYP (SEQ ID NO: 18) |

Example 13: Incorporation of the Selected CDRs into Humanized Antibody and Transformation to IgG The selected CDRs were incorporated into the heavy chain and the light chain of the humanized antibodies. The heavy chain was derived from the antibody cloned with Hu2-6.6 or Hu3-6.6. Polynucleotides encoding the light chain of the antibodies were synthesized by Bioneer, Inc. so as to consist of 'EcoRI-signal sequence-VL-BsiWI-CL-XhoI' (see Table 15). The polynucleotides encoding the heavy chain were respectively cloned into a vector of pOptiVEC™-TOPO TA Cloning Kit included in OptiCHO™ Antibody Express Kit (Cat no. 12762-019; Invitrogen), and the polynucleotides encoding the light chain were respectively cloned into a vector of pcDNA™3.3-TOPOTA Cloning Kit (Cat no. 8300-01), using EcoRI (NEB, R0101S) and XhoI (NEB, R0146S), to establish vectors for expressing affinity matured antibodies.

The constructed vectors were amplified using a Qiagen Maxiprep kit (Cat No. 12662), and the vectors including heavy chain and the vector including the light chain were added to 293T cells ($2.5 \times 10^7$) at a ratio of about 4:1 (about 80 μg:20 μg) with 360 μl of 2 M $CaCl_2$ and were transfected. Next, the mixture was cultured in a DMEM medium with 10% (w/v) FBS at 37° C. in 5% (v/v) $CO_2$ conditions for 5 hours, and then cultured in a DMEM medium without FBS at 37° C. in 5% (v/v) $CO_2$ conditions for 48 hours.

The cultured cells were centrifuged, and 100 ml of each supernatant was purified using AKTA Prime (GE healthcare). Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was replaced with a PBS buffer, and thus final affinity-matured antibodies (hereinafter, named as h10D6-Opti-63, h10D6-Opti-64, h10D6-Opti-65, h10D6-Opti-66, h10D6-Opti-67, h10D6-Opti-71, h10D6-Opti-68, h10D6-Opti-70, h10D6-Opti-72, and h10D6-Opti-73) were purified.

TABLE 15

| Clone | Antibody sequence (VH) | Antibody sequence (VL) |
|---|---|---|
| h10D6-OPTI-63 | >HU2-6.6<br>QVQLQESGPGLVKPSETLSLTCAVSGYS<br>ITSDYAWNWIRQPPGKGLEWMGKISYS<br>GKTDYNPSLKSRSTISRDTSKNQFSLKL<br>SSVTAADTAVYYCARGNFEGAMDYW<br>GQGTLVTVSS (SEQ ID NO: 52)<br><br>(coding nucleotide sequence)<br>CAGGTGCAACTGCAGGAGTCAGGCCC<br>CGGCCTGGTAAAACCTTCTGAAACGC<br>TCTCACTTACCTGTGCCGTTAGTGGAT<br>ACTCTATCACTTCCGACTACGCTTGGA<br>ATTGGATTCGGCAGCCTCCAGGCAAA<br>GGGCTGGAATGG<br>ATGGGAAAGATTTCCTATTCCGGTAA<br>GACTGACTACAATCCCAGTCTGAAGA<br>GCAGGTCAACAATCTCCAGAGACACC<br>AGCAAGAATCAGTTTTCCCTGAAATT<br>GTCCTCGGTGACAGCAGCGGATACCG | >10D6_VL-Hu1-2.1<br>DIQMTQSPSSLSASVGDRVTITCKASQFV<br>STDVHWYQQKPGKAPKLLIYYASNRYP<br>GVPSRFSGSGSGTDFTLTISSLQPEDFATY<br>YCQQDYSSPWTFGQGTKLEIK (SEQ ID NO: 60)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>TTCGTGAGTACTGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT |

TABLE 15-continued

| Clone | Antibody sequence (VH) | Antibody sequence (VL) |
|---|---|---|
| | CAGTGTATTATTGCGCCCGCGGTAAC TTCGAGGGAGCTATGGATTACTGG GGGCAGGGTACTCTCGTCACTGTGAG CAGC(SEQ ID NO: 64) | GGAGGCACCAAGGTGGAAATCAAA(SEQ ID NO: 72) |
| h10D6-OPTI-64 | >HU2-6.6 QVQLQESGPGLVKPSETLSLTCAVSGYS ITSDYAWNWIRQPPGKGLEWMGKISYS GKTDYNPSLKSRSTISRDTSKNQFSLKL SSVTAADTAVYYCARGNFEGAMDYW GQGTLVTVSS(SEQ ID NO: 52) | DIQMTQSPSSLSASVGDRVTITCKASQSV SNDVAWYQQKPGKAPKLLIYYASNRYP GVPSRFSGSGSGTDFTLTISSLQPEDFATY YCGQDYASPWTFGQGTKLEIK(SEQ ID NO: 87) |
| | (coding nucleotide sequence) CAGGTGCAACTGCAGGAGTCAGGCCC CGGCCTGGTAAAACCTTCTGAAACGC TCTCACTTACCTGTGCCGTTAGTGGAT ACTCTATCACTTCCGACTACGCTTGGA ATTGGATTCGGCAGCCTCCAGGCAAA GGGCTGGAATGG ATGGGAAAGATTTCCTATTCCGGTAA GACTGACTACAATCCCAGTCTGAAGA GCAGGTCAACAATCTCCAGAGACACC AGCAAGAATCAGTTTTCCCTGAAATT GTCCTCGGTGACAGCAGCGGATACCG CAGTGTATTATTGCGCCCGCGGTAAC TTCGAGGGAGCTATGGATTACTGG GGGCAGGGTACTCTCGTCACTGTGAG CAGC(SEQ ID NO: 64) | (coding nucleotide sequence) GACATCCAGATGACCCAGTCTCCATCC TCCCTGTCTGCATCTGTAGGAGACAGA GTCACCATCACTTGCAAGGCCAGTCAG AGTGTGAGTAATGATGTAGCT TGGTATCAGCAGAAACCAGGGAAAGC CCCTAAGCTCCTGATCTATTATGCATCC AACCGATACCCTGGGGTCCCATCAAGG TTCAGTGGCAGTGGATCTGGGACAGAT TTCACTCTCACCATCAGCAGTCTGCAA CCTGAAGATTTTGCAACTTACTACTGT GGACAGGATTATGCCTCTCCGTGGACG TTCGGTGGAGGCACCAAGGTGGAAATC AAA(SEQ ID NO: 88) |
| h10D6-OPTI-65 | >HU2-6.6 QVQLQESGPGLVKPSETLSLTCAVSGYS ITSDYAWNWIRQPPGKGLEWMGKISYS GKTDYNPSLKSRSTISRDTSKNQFSLKL SSVTAADTAVYYCARGNFEGAMDYW GQGTLVTVSS(SEQ ID NO: 52) | >10D6_VL-Hu1-2.4 DIQMTQSPSSLSASVGDRVTITCKASQSV SNDVAWYQQKPGKAPKLLIYYASIPYPG VPSRFSGSGSGTDFTLTISSLQPEDFATYY CQQDYSSPWTFGQGTKLEIK(SEQ ID NO: 61) |
| | (coding nucleotide sequence) CAGGTGCAACTGCAGGAGTCAGGCCC CGGCCTGGTAAAACCTTCTGAAACGC TCTCACTTACCTGTGCCGTTAGTGGAT ACTCTATCACTTCCGACTACGCTTGGA ATTGGATTCGGCAGCCTCCAGGCAAA GGGCTGGAATGG ATGGGAAAGATTTCCTATTCCGGTAA GACTGACTACAATCCCAGTCTGAAGA GCAGGTCAACAATCTCCAGAGACACC AGCAAGAATCAGTTTTCCCTGAAATT GTCCTCGGTGACAGCAGCGGATACCG CAGTGTATTATTGCGCCCGCGGTAAC TTCGAGGGAGCTATGGATTACTGG GGGCAGGGTACTCTCGTCACTGTGAG CAGC(SEQ ID NO: 64) | (coding nucleotide sequence) GACATCCAGATGACCCAGTCTCCATCC TCCCTGTCTGCATCTGTAGGAGACAGA GTCACCATCACTTGCAAGGCCAGTCAG AGTGTGAGTAATGATGTAGCTTGGTAT CAGCAGAAACCAGGGAAAGCCCCTAA GCTCCTGATCTATTATGCATCCATCCCA TACCCTGGGGTCCCATCAAGGTTCAGT GGCAGTGGATCTGGGACAGATTTCACT CTCACCATCAGCAGTCTGCAACCTGAA GATTTTGCAACTTACTACTGTCAGCAG GATTATAGCTCTCCGTGGACGTTCGGT GGAGGCACCAAGGTGGAAATCAAA(SEQ ID NO: 73) |
| h10D6-OPTI-66 | >HU2-6.6 QVQLQESGPGLVKPSETLSLTCAVSGYS ITSDYAWNWIRQPPGKGLEWMGKISYS GKTDYNPSLKSRSTISRDTSKNQFSLKL SSVTAADTAVYYCARGNFEGAMDYW GQGTLVTVSS(SEQ ID NO: 52) | DIQMTQSPSSLSASVGDRVTITCKASQSV SNDVHWYQQKPGKAPKLLIYYASNRYP GVPSRFSGSGSGTDFTLTISSLQPEDFATY YCGQDYSAPWTFGQGTKLEIK(SEQ ID NO: 89) |
| | (coding nucleotide sequence) CAGGTGCAACTGCAGGAGTCAGGCCC CGGCCTGGTAAAACCTTCTGAAACGC TCTCACTTACCTGTGCCGTTAGTGGAT ACTCTATCACTTCCGACTACGCTTGGA ATTGGATTCGGCAGCCTCCAGGCAAA GGGCTGGAATGG ATGGGAAAGATTTCCTATTCCGGTAA GACTGACTACAATCCCAGTCTGAAGA GCAGGTCAACAATCTCCAGAGACACC AGCAAGAATCAGTTTTCCCTGAAATT GTCCTCGGTGACAGCAGCGGATACCG CAGTGTATTATTGCGCCCGCGGTAAC TTCGAGGGAGCTATGGATTACTGG GGGCAGGGTACTCTCGTCACTGTGAG CAGC(SEQ ID NO: 64) | (coding nucleotide sequence) GACATCCAGATGACCCAGTCTCCATCC TCCCTGTCTGCATCTGTAGGAGACAGA GTCACCATCACTTGCAAGGCCAGTCAG AGTGTGAGTAATGATGTACAC TGGTATCAGCAGAAACCAGGGAAAGC CCCTAAGCTCCTGATCTATTATGCATCC AACCGATACCCTGGGGTCCCATCAAGG TTCAGTGGCAGTGGATCTGGGACAGAT TTCACTCTCACCATCAGCAGTCTGCAA CCTGAAGATTTTGCAACTTACTACTGT GGACAGGATTATTCTGCCCCGTGGACG TTCGGTGGAGGCACCAAGGTGGAAATC AAA(SEQ ID NO: 90) |

TABLE 15-continued

| Clone | Antibody sequence (VH) | Antibody sequence (VL) |
|---|---|---|
| h10D6-OPTI-67 | >HU2-6.6<br>QVQLQESGPGLVKPSETLSLTCAVSGYS<br>ITSDYAWNWIRQPPGKGLEWMGKISYS<br>GKTDYNPSLKSRSTISRDTSKNQFSLKL<br>SSVTAADTAVYYCARGNFEGAMDYW<br>GQGTLVTVSS(SEQ ID NO: 52)<br><br>(coding nucleotide sequence)<br>CAGGTGCAACTGCAGGAGTCAGGCCC<br>CGGCCTGGTAAAACCTTCTGAAACGC<br>TCTCACTTACCTGTGCCGTTAGTGGAT<br>ACTCTATCACTTCCGACTACGCTTGGA<br>ATTGGATTCGGCAGCCTCCAGGCAAA<br>GGGCTGGAATGG<br>ATGGGAAAGATTTCCTATTCCGGTAA<br>GACTGACTACAATCCCAGTCTGAAGA<br>GCAGGTCAACAATCTCCAGAGACACC<br>AGCAAGAATCAGTTTTCCCTGAAATT<br>GTCCTCGGTGACAGCAGCGGATACCG<br>CAGTGTATTATTGCGCCCGCGGTAAC<br>TTCGAGGGAGCTATGGATTACTGG<br>GGGCAGGGTACTCTCGTCACTGTGAG<br>CAGC(SEQ ID NO: 64) | >10D6_VL-Hu1-2.7<br>DIQMTQSPSSLSASVGDRVTITCKASQSV<br>SNDVHWYQQKPGKAPKLLIYYASIPYPG<br>VPSRFSGSGSGTDFTLTISSLQPEDFATYY<br>CQQDYSSPWTFGQGTKLEIK(SEQ ID<br>NO: 62)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCATCCCA<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 74) |
| h10D6-OPTI-71 | >HU2-6.6<br>QVQLQESGPGLVKPSETLSLTCAVSGYS<br>ITSDYAWNWIRQPPGKGLEWMGKISYS<br>GKTDYNPSLKSRSTISRDTSKNQFSLKL<br>SSVTAADTAVYYCARGNFEGAMDYW<br>GQGTLVTVSS(SEQ ID NO: 52)<br><br>(coding nucleotide sequence)<br>CAGGTGCAACTGCAGGAGTCAGGCCC<br>CGGCCTGGTAAAACCTTCTGAAACGC<br>TCTCACTTACCTGTGCCGTTAGTGGAT<br>ACTCTATCACTTCCGACTACGCTTGGA<br>ATTGGATTCGGCAGCCTCCAGGCAAA<br>GGGCTGGAATGG<br>ATGGGAAAGATTTCCTATTCCGGTAA<br>GACTGACTACAATCCCAGTCTGAAGA<br>GCAGGTCAACAATCTCCAGAGACACC<br>AGCAAGAATCAGTTTTCCCTGAAATT<br>GTCCTCGGTGACAGCAGCGGATACCG<br>CAGTGTATTATTGCGCCCGCGGTAAC<br>TTCGAGGGAGCTATGGATTACTGG<br>GGGCAGGGTACTCTCGTCACTGTGAG<br>CAGC(SEQ ID NO: 64) | 10D6_VL-Hu1-2.8<br>DIQMTQSPSSLSASVGDRVTITCKASQFV<br>STDVHWYQQKPGKAPKLLIYYASIPYPG<br>VPSRFSGSGSGTDFTLTISSLQPEDFATYY<br>CQQDYSSPWTFGQGTKLEIK(SEQ ID<br>NO: 63)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>TTCGTGAGTACTGATGTACATTGGTAT<br>CAGCAGAAACCAGGGAAAGCCCCTAA<br>GCTCCTGATCTATTATGCATCCATCCCA<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 75) |
| h10D6-OPTI-68 | >HU3-6.6<br>EVQLVESGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54)<br><br>(coding nucleotide sequence)<br>GAGGTTCAGCTGGTCGAAAGCGGTGG<br>GGGACTCGTGCAGCCAGGCGGTTCTC<br>TTAGATTATCATGTGCCGCATCCGGGT<br>ACTCCATCACCTCTGATTATGCATGGA<br>ACTGGGTCAGACAAGCCCCCGGAAAG<br>GGCTGGAGTGGATGGGGAAGATCTC<br>CTATTCAGGGAAGACAGATTATAATC<br>CTTCGCTGAAAAGCAGATCAACAATT<br>AGTAGAGACACTTCTAAAAATACTTT<br>TTACCTCCAGATGAACAGTCTGCGCG<br>CCGAAGACACCGCCGTGTACTACTGC<br>GCTAGGGGAAATTTCGAGGGAGCTAT<br>GGACTATTGGGGCCAGGGCACGTTGG<br>TAACCGTGAGCAGC(SEQ ID NO: 66) | >10D6_VL-Hu1-2.1<br>DIQMTQSPSSLSASVGDRVTITCKASQFV<br>STDVHWYQQKPGKAPKLLIYYASNRYP<br>GVPSRFSGSGSGTDFTLTISSLQPEDFATY<br>YCQQDYSSPWTFGQGTKLEIK(SEQ ID<br>NO: 60)<br><br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>TTCGTGAGTACTGATGTACATTGGTAT<br>CAGCAGAAACCAGGGAAAGCCCCTAA<br>GCTCCTGATCTATTATGCATCCAATCGC<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 72) |
| h10D6-OPTI-70 | >HU3-6.6<br>EVQLVESGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54) | >10D6_VL-Hu1-2.4<br>DIQMTQSPSSLSASVGDRVTITCKASQSV<br>SNDVAWYQQKPGKAPKLLIYYASIPYPG<br>VPSRFSGSGSGTDFTLTISSLQPEDFATYY<br>CQQDYSSPWTFGQGTKLEIK(SEQ ID<br>NO: 61) |

TABLE 15-continued

| Clone | Antibody sequence (VH) | Antibody sequence (VL) |
|---|---|---|
| | (coding nucleotide sequence)<br>GAGGTTCAGCTGGTCGAAAGCGGTGG<br>GGGACTCGTGCAGCCAGGCGGTTCTC<br>TTAGATTATCATGTGCCGCATCCGGGT<br>ACTCCATCACCTCTGATTATGCATGGA<br>ACTGGGTCAGACAAGCCCCCGGAAAG<br>GGCCTGGAGTGGATGGGAAGATCTC<br>CTATTCAGGGAAGACAGATTATAATC<br>CTTCGCTGAAAAGCAGATCAACAATT<br>AGTAGAGACACTTCTAAAAATACTTT<br>TTACCTCCAGATGAACAGTCTGCGCG<br>CCGAAGACACCGCCGTGTACTACTGC<br>GCTAGGGGAAATTTCGAGGGAGCTAT<br>GGACTATTGGGGCCAGGGCACGTTGG<br>TAACCGTGAGCAGC(SEQ ID NO: 66) | (coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTAGCTTGGTAT<br>CAGCAGAAACCAGGGAAAGCCCCTAA<br>GCTCCTGATCTATTATGCATCCATCCCA<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 73) |
| h10D6-OPTI-72 | >HU3-6.6<br>EVQLVESGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54) | >10D6_VL-Hu1-2.7<br>DIQMTQSPSSLSASVGDRVTITCKASQSV<br>SNDVHWYQQKPGKAPKLLIYYASIPYPG<br>VPSRFSGSGSGTDFTLTISSLQPEDFATYY<br>CQQDYSSPWTFGQGTKLEIK(SEQ ID<br>NO: 62) |
| | (coding nucleotide sequence)<br>GAGGTTCAGCTGGTCGAAAGCGGTGG<br>GGGACTCGTGCAGCCAGGCGGTTCTC<br>TTAGATTATCATGTGCCGCATCCGGGT<br>ACTCCATCACCTCTGATTATGCATGGA<br>ACTGGGTCAGACAAGCCCCCGGAAAG<br>GGCCTGGAGTGGATGGGAAGATCTC<br>CTATTCAGGGAAGACAGATTATAATC<br>CTTCGCTGAAAAGCAGATCAACAATT<br>AGTAGAGACACTTCTAAAAATACTTT<br>TTACCTCCAGATGAACAGTCTGCGCG<br>CCGAAGACACCGCCGTGTACTACTGC<br>GCTAGGGGAAATTTCGAGGGAGCTAT<br>GGACTATTGGGGCCAGGGCACGTTGG<br>TAACCGTGAGCAGC(SEQ ID NO: 66) | (coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>AGTGTGAGTAATGATGTACATTGGTAT<br>CAGCAGAAACCAGGGAAAGCCCCTAA<br>GCTCCTGATCTATTATGCATCCATCCCA<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 74) |
| h10D6-OPTI-73 | >HU3-6.6<br>EVQLVESGGGLVQPGGSLRLSCAASGY<br>SITSDYAWNWVRQAPGKGLEWMGKIS<br>YSGKTDYNPSLKSRSTISRDTSKNTFYL<br>QMNSLRAEDTAVYYCARGNFEGAMD<br>YWGQGTLVTVSS(SEQ ID NO: 54)<br>(coding nucleotide sequence)<br>GAGGTTCAGCTGGTCGAAAGCGGTGG<br>GGGACTCGTGCAGCCAGGCGGTTCTC<br>TTAGATTATCATGTGCCGCATCCGGGT<br>ACTCCATCACCTCTGATTATGCATGGA<br>ACTGGGTCAGACAAGCCCCCGGAAAG<br>GGCCTGGAGTGGATGGGAAGATCTC<br>CTATTCAGGGAAGACAGATTATAATC<br>CTTCGCTGAAAAGCAGATCAACAATT<br>AGTAGAGACACTTCTAAAAATACTTT<br>TTACCTCCAGATGAACAGTCTGCGCG<br>CCGAAGACACCGCCGTGTACTACTGC<br>GCTAGGGGAAATTTCGAGGGAGCTAT<br>GGACTATTGGGGCCAGGGCACGTTGG<br>TAACCGTGAGCAGC(SEQ ID NO: 66) | 10D6_VL-Hu1-2.8<br>DIQMTQSPSSLSASVGDRVTITCKASQFV<br>STDVHWYQQKPGKAPKLLIYYASIPYPG<br>VPSRFSGSGSGTDFTLTISSLQPEDFATYY<br>CQQDYSSPWTFGQGTKLEIK(SEQ ID<br>NO: 63)<br>(coding nucleotide sequence)<br>GACATCCAGATGACCCAGTCTCCATCC<br>TCCCTGTCTGCATCTGTAGGAGACAGA<br>GTCACCATCACTTGCAAGGCCAGTCAG<br>TTCGTGAGTACTGATGTACATTGGTAT<br>CAGCAGAAACCAGGGAAAGCCCCTAA<br>GCTCCTGATCTATTATGCATCCATCCCA<br>TACCCTGGGGTCCCATCAAGGTTCAGT<br>GGCAGTGGATCTGGGACAGATTTCACT<br>CTCACCATCAGCAGTCTGCAACCTGAA<br>GATTTTGCAACTTACTACTGTCAGCAG<br>GATTATAGCTCTCCGTGGACGTTCGGT<br>GGAGGCACCAAGGTGGAAATCAAA(SEQ<br>ID NO: 75) |

(In Table 15, the bold letters are CDR1, CDR2 and CDR3 in sequence)

Example 14: Analysis of Binding Affinity of Selected Antibodies

The binding affinity (KD values) of the antibodies to human Ang2 protein was measured by an SPR method using a BIAcore T100 (GE Healthcare). 25 μg/ml anti-His antibody was immobilized on a CM5 sensor chip (GE healthcare) using a pH 5.0 acetate solution and an amine coupling kit (GE Healthcare). 6 μg/ml of a recombinant hAng2 (C-His, R&D Systems) protein was flowed onto the chip to be captured at 100 to 200 RU levels. The antibodies obtained in the above examples were diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. The KD values were calculated from the values of $k_{on}$, $k_{off}$, and the results are as shown in the following Table 16.

TABLE 16

| Antibody | kon (1/Ms) | koff (1/s) | KD (M) |
|---|---|---|---|
| h10D6-OPTI-63 | $2.676 \times 10^6$ | $7.421 \times 10^{-5}$ | $2.773 \times 10^{-11}$ |
| h10D6-OPTI-65 | $4.960 \times 16^5$ | $2.250 \times 10^{-5}$ | $4.536 \times 10^{-12}$ |
| h10D6-OPTI-67 | $2.080 \times 16^6$ | $2.684 \times 10^{-7}$ | $1.291 \times 10^{-13}$ |
| h10D6-OPTI-68 | $5.355 \times 10^5$ | $1.696 \times 10^{-4}$ | $3.168 \times 10^{-10}$ |
| h10D6-OPTI-70 | $2.650 \times 10^5$ | $1.159 \times 10^{-4}$ | $4.374 \times 10^{-10}$ |

As shown in Table 16, all the affinity-matured and humanized antibodies show high affinity to Ang2 from about 0.000129 nM to about 0.43 nM.

Example 15: Analysis of In Vitro Biological Property of the Selected Affinity-Matured Antibodies—Akt Phosphorylation To examine whether the humanized and/or affinity-matured 10D6 antibodies can induce activation of downstream signaling as well as Tie2 receptor, the levels of Akt phosphorylation in HUVEC (ATCC) cells treated with Ang2 and each of the antibodies (see Table 15) of Example 13 were measured and compared to that of the case treated with Ang2 only. HUVEC (ATCC) cells ($2 \times 10^4$ cells) were cultured in 96 well plate using EGM-2 medium (Lonza) at 37° C., and when they reached 80~90% confluency, the media were replaced with serum-free medium (Lonza) and cultured at 37° C. for 6 hours. The cultured cells were treated with a mixture prepared by mixing 6 nM, 1.2 nM, or 0.24 nM of each of the anti-Ang2 antibodies of Example 13 with 4 nM of Ang2 protein (R&D systems) and letting them stand for 20 min. and further cultured for 30 min.

The phosphorylation of Akt which participates in downstream signaling of Tie2 receptor was examined using PATHSCAN® Phospho-Akt Chemiluminescent Sandwich ELISA Kit (Cell signaling, #7134). The cells were washed using PBS, treated with 30 μl of a lysis buffer (Roche), to be subjected to cell lysis at 4° C. for 30 minutes. Then, 30 μl of diluent buffer (Cell signaling) was added to each well and sufficiently mixed with pipet, and 50 μl of the diluted product was collected and transferred to a phosphor-Akt Ab coated microwell, to react at room temperature for 2 hours. After 2 hours, the well was washed with 1x washing buffer (Cell signaling) four times, and treated with 50 μl of Akt1 detection antibody solution (Cell signaling), to react at room temperature for one hour. As the same process, the well was washed, and reacted with 50 μl of HRP-conjugated secondary antibody (Cell signaling) at room temperature for 30 minutes. As the same process, the well was washed, and treated with 50 μl of a mixture solution of luminol/enhancer solution (GE healthcare) and stable peroxide buffer (GE healthcare) at the ratio of 1:1 (v/v). Then the plate was placed in a luminometer (Envision 2104 plate reader, Perkin Elmer), to measure a relative light unit (RLU).

Figure 5:
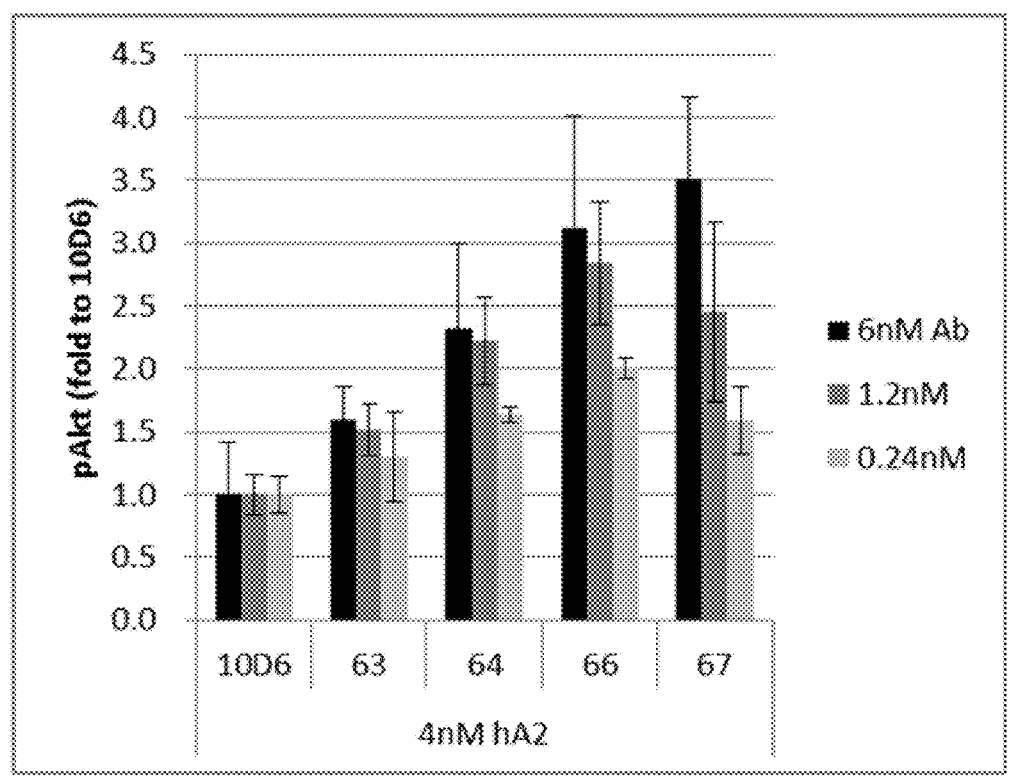
FIG. 5 is a graph showing the phosphorylation level of Akt that participated in downstream signaling of Tie2 receptor, by humanized and affinity-matured anti-Ang2 antibodies as compared to a control.

The obtained results are shown in FIG. 5. As seen in FIG. 5, the humanized and/or affinity-matured antibodies pf Example 13 induce the downstream signaling more intensively compared to mouse antibody 10D6.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-Ang2 antibody or an antigen-binding fragment thereof that binds to Ang2 and binds to Tie2 receptor via Ang2, comprising:
   a heavy chain variable region comprising a polypeptide (CDR-H1) comprising SEQ ID NO: 1, a polypeptide (CDR-H2) comprising SEQ ID NO: 20, and a polypeptide (CDR-H3) comprising SEQ ID NO: 3; and
   a light chain variable region comprising a polypeptide (CDR-L1) comprising SEQ ID NO: 21, a polypeptide (CDR-L2) comprising SEQ ID NO: 22, and a polypeptide (CDR-L3) comprising SEQ ID NO: 23;
   or comprising:
   a heavy chain variable region comprising a polypeptide (CDR-H1) comprising SEQ ID NO: 1, a polypeptide (CDR-H2) comprising SEQ ID NO: 14, and a polypeptide (CDR-H3) comprising SEQ ID NO: 3; and
   a light chain variable region comprising a polypeptide (CDR-L1) comprising SEQ ID NO: 4, a polypeptide (CDR-L2) comprising SEQ ID NO: 5, and a polypeptide (CDR-L3) comprising SEQ ID NO: 91;
   or comprising:
   a heavy chain variable region comprising a polypeptide (CDR-H1) comprising SEQ ID NO: 1, a polypeptide (CDR-H2) comprising SEQ ID NO: 14, and a polypeptide (CDR-H3) comprising SEQ ID NO: 3; and
a light chain variable region comprising a polypeptide (CDR-L1) comprising SEQ ID NO: 16, a polypeptide (CDR-L2) comprising SEQ ID NO: 5, and a polypeptide (CDR-L3) comprising SEQ ID NO: 92;
with the proviso that the anti-Ang2 antibody or an antigen-binding fragment thereof does not comprise all of a polypeptide (CDR-H1) comprising SEQ ID NO: 1, a polypeptide (CDR-H2) comprising SEQ ID NO: 2, a polypeptide (CDR-H3) comprising SEQ ID NO: 3, a polypeptide (CDR-L1) comprising SEQ ID NO: 4, a polypeptide (CDR-L2) comprising SEQ ID NO: 5, and a polypeptide (CDR-L3) comprising SEQ ID NO: 6;
and wherein SEQ ID NOs: 21, 22, 23, and 24 are as follows:

$X_1IX_3YX_5GX_7TDYNPSLKS$ (SEQ ID NO: 20), wherein:
$X_1$ is Y or K;
$X_3$ is N or S;
$X_5$ is S or A; and
$X_7$ is N or K;

$KASQX_5VSX_8DVX_{11}$ (SEQ ID NO: 21), wherein:
$X_5$ is S or F;
$X_8$ is N or T; and
$X_{11}$ is A or H;

$YASX_4X_5YP$ (SEQ ID NO: 22), wherein:
$X_4$ is N or I; and
$X_5$ is R or P;

$QX_2DYSSPX_8T$ (SEQ ID NO: 23); wherein:
$X_2$ is Q or H; and
$X_8$ is W or F.

2. The anti-Ang2 antibody or an antigen-binding fragment thereof of claim 1, comprising:
a heavy chain variable region comprising a polypeptide (CDR-H1) comprising SEQ ID NO: 1, a polypeptide (CDR-H2) comprising an amino acid sequence selected from the group consisting of SEQ ID NOs: 2, 14, and 15, and a polypeptide (CDR-H3) comprising SEQ ID NO: 3; and
a light chain variable region comprising a polypeptide (CDR-L1) comprising an amino acid sequence selected from the group consisting of SEQ ID NOs: 4, 16, and 17, a polypeptide (CDR-L2) comprising SEQ ID NO: 5 or 18, and a polypeptide (CDR-L3) comprising SEQ ID NO: 6, or 19;
with the proviso that the anti-Ang2 antibody or an antigen-binding fragment thereof does not comprise all of a polypeptide (CDR-H1) comprising SEQ ID NO: 1, a polypeptide (CDR-H2) comprising SEQ ID NO: 2, a polypeptide (CDR-H3) comprising SEQ ID NO: 3, a polypeptide (CDR-L1) comprising SEQ ID NO: 4, a polypeptide (CDR-L2) comprising SEQ ID NO: 5, and a polypeptide (CDR-L3) comprising SEQ ID NO: 6 at the same time.

3. The anti-Ang2 antibody or an antigen-binding fragment thereof of claim 1, comprising:
a heavy chain variable region comprising one of SEQ ID NOs: 52 to 56, and
a light chain variable region comprising one of SEQ ID NOs: 57 to 63.

4. The anti-Ang2 antibody or an antigen-binding fragment thereof of claim 1, wherein the anti-Ang2 antibody or antigen binding fragment is an scFv, (scFv)2, scFv-Fc, Fab, Fab' or F(ab')2 antigen binding antibody fragment.

5. A pharmaceutical composition comprising the anti-Ang2 antibody or an antigen-binding fragment thereof of claim 1, and a carrier.

6. The anti-Ang2 antibody of claim 1, wherein the anti-Ang2 antibody is a humanized antibody, an affinity-matured antibody, or a combination thereof.

7. The anti-Ang2 antibody or an antigen-binding fragment thereof of claim 1, comprising:
a heavy chain variable region comprising SEQ ID NO: 52, and
a light chain variable region comprising SEQ ID NO: 87 or 89.

8. A method of preparing an anti-Ang2 antibody of claim 1, the method comprising expressing a polynucleotide encoding the anti-Ang2 antibody of claim 1 in a cell.

* * * * *